United States Patent
Little et al.

(10) Patent No.: US 11,492,644 B2
(45) Date of Patent: Nov. 8, 2022

(54) GENETICALLY INDUCED NEPHRON PROGENITORS

(71) Applicants: MURDOCH CHILDRENS RESEARCH INSTITUTE, Victoria (AU); VANDERBILT UNIVERSITY, Nashville, TN (US); THE UNITED STATES GOVERNMENT AS REPRESENTED BY THE DEPARTMENT OF VETERANS AFFAIRS, Washington, DC (US)

(72) Inventors: Melissa Little, Victoria (AU); Jessica Vanslambrouck, Victoria (AU); Lauren Woodard, Nashville, TN (US); Matthew Wilson, Nashville, TN (US)

(73) Assignees: MURDOCH CHILDRENS RESEARCH INSTITUTE, Victoria (AU); VANDERBILT UNIVERSITY, Nashville, TN (US); THE UNITED STATES GOVERNMENT AS REPRESENTED BY THE DEPARTMENT OE VETERANS AFFAIRS, Washington, DC (US)

( * ) Notice: Subject to any disclaimer, the term of this patent is extended or adjusted under 35 U.S.C. 154(b) by 255 days.

(21) Appl. No.: 16/616,229

(22) PCT Filed: May 24, 2018

(86) PCT No.: PCT/AU2018/050502
§ 371 (c)(1),
(2) Date: Nov. 22, 2019

(87) PCT Pub. No.: WO2018/213886
PCT Pub. Date: Nov. 29, 2018

(65) Prior Publication Data
US 2020/0157572 A1 May 21, 2020

Related U.S. Application Data

(60) Provisional application No. 62/510,314, filed on May 24, 2017.

(51) Int. Cl.
*C12N 15/90* (2006.01)
*C12N 5/071* (2010.01)
*C12N 15/85* (2006.01)

(52) U.S. Cl.
CPC ........... *C12N 15/90* (2013.01); *C12N 5/0686* (2013.01); *C12N 15/85* (2013.01); *C12N 2510/00* (2013.01)

(58) Field of Classification Search
CPC ... C12N 15/90; C12N 5/0686; C12N 2510/00
See application file for complete search history.

(56) References Cited

U.S. PATENT DOCUMENTS

| | | |
|---|---|---|
| 2012/0116568 A1 | 5/2012 | Murphy et al. |
| 2013/0164339 A1 | 6/2013 | Murphy et al. |
| 2014/0012407 A1 | 1/2014 | Murphy et al. |

FOREIGN PATENT DOCUMENTS

| | | |
|---|---|---|
| WO | 2014/197934 | 12/2014 |
| WO | 2016/094948 | 6/2016 |

OTHER PUBLICATIONS

Al-Awqati, Q. and Oliver, J. A. (2002). Stem cells in the kidney. Kidney Int, 61, 387-95.
Altschul, Stephen F., et al. "Gapped BLAST and PSI-BLAST: a new generation of protein database search programs." Nucleic acids research 25.17 (1997): 3389-3402.
Barak, H., Huh, S. H., Chen, S., Jeanpierre, C., Martinovic, J., Parisot, M., Bole-Feysot, C., Nitschke, P., Salomon, R., Antignac, C., et al. (2012). FGF9 and FGF20 maintain the sternness of nephron progenitors in mice and man. Dev Cell, 22, 1191-207.
Barasch, J., Yang, J., Ware, C. B., Taga, T., Yoshida, K., Erdjument-Bromage, H., Tempst, P., Parravicini, E., Malach, S., Aranoff, T., et al. (1999). Mesenchymal to epithelial conversion in rat metanephros is induced by LIF. Cell, 99, 377-86.
Bolger, A. M., Lohse, M. and Usadel, B. (2014). Trimmomatic: a flexible trimmer for Illumina sequence data. Bioinformatics, 30, 2114-20.
Briggs, J. A., Sun, J., Shepherd, J., Ovchinnikov, D. A., Chung, T. L., Nayler, S. P., Kao, L. P., Morrow, C. A., Thakar, N. Y., Soo, S. Y., et al. (2013). Integration-free induced pluripotent stem cells model genetic and neural developmental features of down syndrome etiology. Stem Cells, 31, 467-78.
Brown, A. C., Muthukrishnan, S. D. and Oxburgh, L. (2015). A synthetic niche for nephron progenitor cells. Dev Cell, 34, 229-41.
Brown, A. C., Muthukrishnan, S. D., Guay, J. A., Adams, D. C., Schafer, D. A., Fetting, J. L. and Oxburgh, L. (2013). Role for compartmentalization in nephron progenitor differentiation. Proc Natl Acad Sci U S A, 110, 4640-5.
Buganim, Y., Itskovich, E., Hu, Y. C., Cheng, A. W., Ganz, K., Sarkar, S., Fu, D., Welstead, G. G., Page, D. C. and Jaenisch, R. (2012). Direct reprogramming of fibroblasts into embryonic Sertoli-like cells by defined factors. Cell Stem Cell, 11, 373-86.
Chen, R., Amoui, M., Zhang, Z. and Mardon, G. (1997). Dachshund and eyes absent proteins form a complex and function synergistically to induce ectopic eye development in *Drosophila*. Cell, 91, 893-903.

(Continued)

*Primary Examiner* — Valarie E Bertoglio
(74) *Attorney, Agent, or Firm* — Meunier Carlin & Curfman LLC

(57) ABSTRACT

Expression of exogenous SNAI2, EYA1 and SIX1 genes in a cell, tissue or organ not normally having nephron progenitor activity, induces or re-programs that cell to have or subsequently develop nephron progenitor activity. Nephron progenitors induced 5 by expression of SNAI2, EYA1 and SIX1 may be used for the production of nephron cells and tissues that are useful in treatment of kidney disorders, kidney regeneration, kidney transplantation, bioprinting and nephrotoxocity testing.

3 Claims, 15 Drawing Sheets

Specification includes a Sequence Listing.

(56) References Cited

OTHER PUBLICATIONS

Da Sacco, S., Thornton, M. E., Petrosyan, A., Lavarreda-Pearce, M., Sedrakyan, S., Grubbs, B. H., De Filippo, R. E. and Perin, L. (2016). Direct Isolation and Characterization of Human Nephron Progenitors. Stem Cells Transl Med, 6, 419-433.

Davies, J. A., Unbekandt, M., Ineson, J., Lusis, M. and Little, M. H. (2012). Dissociation of embryonic kidney followed by re-aggregation as a method for chimeric analysis. Methods Mol Biol, 886, 135-46.

Dobin, A., Davis, C. A., Schlesinger, F., Drenkow, J., Zaleski, C., Jha, S., Batut, P., Chaisson, M. and Gingeras, T. R. (2013). STAR: ultrafast universal RNA-seq aligner. Bioinformatics, 29, 15-21.

Doherty, J. E., Huye, L. E., Yusa, K., Zhou, L., Craig, N. L. and Wilson, M. H. (2012). Hyperactive piggyBac gene transfer in human cells and in vivo. Hum Gene Ther, 23, 311-20.

Edgar, R., Domrachev, M. and Lash, A. E. (2002). Gene Expression Omnibus: NCBI gene expression and hybridization array data repository. Nucleic Acids Res, 30, 207-10.

Elick, T. A., Bauser, C. A. and Fraser, M. J. (1996). Excision of the piggyBac transposable element in vitro is a precise event that is enhanced by the expression of its encoded transposase. Genetica, 98, 33-41.

Gentleman, R. C., Carey, V. J., Bates, D. M., Bolstad, B., Dettling, M., Dudoit, S., Ellis, B., Gautier, L., Ge, Y., Gentry, J., et al. (2004). Bioconductor: open software development for computational biology and bioinformatics. Genome Biol, 5, R80.

Han, D. W., Tapia, N., Hermann, A., Hemmer, K., Hoing, S., Arauzo-Bravo, M. J., Zaehres, H., Wu, G., Frank, S., Moritz, S., et al. (2012). Direct reprogramming of fibroblasts into neural stem cells by defined factors. Cell Stem Cell, 10, 465-72.

Harari-Steinberg, O., Metsuyanim, S., Omer, D., Gnatek, Y., Gershon, R., Pri-Chen, S., Ozdemir, D. D., Lerenthal, Y., Noiman, T., Ben-Hur, H., et al. (2013). Identification of human nephron progenitors capable of generation of kidney structures and functional repair of chronic renal disease. EMBO Mol Med, 5, 1556-68.

Hartman, H. A., Lai, H. L. and Patterson, L. T. (2007). Cessation of renal morphogenesis in mice. Dev Biol, 310, 379-87.

Hendry, C. E. and Little, M. H. (2012). Reprogramming the kidney: a novel approach for regeneration. Kidney Int, 82, 138-46.

Hendry, C. E., Vanslambrouck, J. M., Ineson, J., Suhaimi, N., Takasato, M., Rae, F. and Little, M. H. (2013). Direct transcriptional reprogramming of adult cells to embryonic nephron progenitors. J Am Soc Nephrol, 24, 1424-34.

Hendry, Caroline E., et al. "Direct transcriptional reprogramming of adult cells to embryonic nephron progenitors." Journal of the American Society of Nephrology 24.9 (2013): 1424-1434.

Huang, P., He, Z., Ji, S., Sun, H., Xiang, D., Liu, C., Hu, Y., Wang, X. and Hui, L. (2011). Induction of functional hepatocyte-like cells from mouse fibroblasts by defined factors. Nature, 475, 386-9.

Huangfu, D., Maehr, R., Guo, W., Eijkelenboom, A., Snitow, M., Chen, A. E. and Melton, D. A. (2008). Induction of pluripotent stem cells by defined factors is greatly improved by small-molecule compounds. Nat Biotechnol, 26, 795-7.

Ieda, M., Fu, J. D., Delgado-Olguin, P., Vedantham, V., Hayashi, Y., Bruneau, B. G. and Srivastava, D. (2010). Direct reprogramming of fibroblasts into functional cardiomyocytes by defined factors. Cell, 142, 375-86.

Imberti, B., Tomasoni, S., Ciampi, O., Pezzotta, A., Derosas, M., Xinaris, C., Rizzo, P., Papadimou, E., Novelli, R., Benigni, A., et al. (2015). Renal progenitors derived from human iPSCs engraft and restore function in a mouse model of acute kidney injury. Sci Rep, 5, 8826.

Jha, V., Garcia-Garcia, G., Iseki, K., Li, Z., Naicker, S., Plattner, B., Saran, R., Wang, A. Y. and Yang, C. W. (2013). Chronic kidney disease: global dimension and perspectives. Lancet, 382, 260-72.

Jones, S. G., Ito, T. and Phillips, A. O. (2003). Regulation of proximal tubular epithelial cell CD44-mediated binding and internalisation of hyaluronan. Int J Biochem Cell Biol, 35, 1361-77.

Kahlig, K. M., Saridey, S. K., Kaja, A., Daniels, M. A., George, A. L., Jr. and Wilson, M. H. (2010). Multiplexed transposon-mediated stable gene transfer in human cells. Proc Natl Acad Sci U S A, 107, 1343-8.

Kaminski, M. M., Tosic, J., Kresbach, C., Engel, H., Klockenbusch, J., Muller, A. L., Pichler, R., Grahammer, F., Kretz, O., Huber, T. B., et al. (2016). Direct reprogramming of fibroblasts into renal tubular epithelial cells by defined transcription factors. Nat Cell Biol, 18, 1269-1280.

Karner, C. M., Das, A., Ma, Z., Self, M., Chen, C., Lum, L., Oliver, G. and Carroll, T. J. (2011). Canonical Wnt9b signaling balances progenitor cell expansion and differentiation during kidney development. Development, 138, 1247-57.

Kobayashi, A., Valerius, M. T., Mugford, J. W., Carroll, T. J., Self, M., Oliver, G. and Mcmahon, A. P. (2008). Six2 defines and regulates a multipotent self-renewing nephron progenitor population throughout mammalian kidney development. Cell Stem Cell, 3, 169-81.

Lam, A. Q., Freedman, B. S., Morizane, R., Lerou, P. H., Valerius, M. T. and Bonventre, J. V. (2014). Rapid and efficient differentiation of human pluripotent stem cells into intermediate mesoderm that forms tubules expressing kidney proximal tubular markers. J Am Soc Nephrol, 25, 1211-25.

Law, C. W., Chen, Y., Shi, W. and Smyth, G. K. (2014). voom: Precision weights unlock linear model analysis tools for RNA-seq read counts. Genome Biol, 15, R29.

Li, J., Ariunbold, U., Suhaimi, N., Sunn, N., Guo, J., Mcmahon, J. A., Mcmahon, A. P. and Little, M. (2015). Collecting duct-derived cells display mesenchymal stem cell properties and retain selective in vitro and in vivo epithelial capacity. J Am Soc Nephrol, 26, 81-94.

Li, M. A., Turner, D. J., Ning, Z., Yusa, K., Liang, Q., Eckert, S., Rad, L., Fitzgerald, T. W., Craig, N. L. and Bradley, A. (2011). Mobilization of giant piggyBac transposons in the mouse genome. Nucleic Acids Res, 39, e148.

Li, X., Oghi, K. A., Zhang, J., Krones, A., Bush, K. T., Glass, C. K., Nigam, S. K., Aggarwal, A. K., Maas, R., Rose, D. W., et al. (2003). Eya protein phosphatase activity regulates Six1-Dach-Eya transcriptional effects in mammalian organogenesis. Nature, 426, 247-54.

Li, Z., Araoka, T., Wu, J., Liao, H. K., Li, M., Lazo, M., Zhou, B., Sui, Y., Wu, M. Z., Tamura, I., et al. (2016). 3D Culture Supports Long-Term Expansion of Mouse and Human Nephrogenic Progenitors. Cell Stem Cell, 19, 516-529.

Liao, Y., Smyth, G. K. and Shi, W. (2014). featureCounts: an efficient general purpose program for assigning sequence reads to genomic features. Bioinformatics, 30, 923-30.

Little, M. H., et al. "Transcriptional reprogramming and directed diffenrentiation of pluripotent stem cells: Alternative options for regenerating kidney." Journal of Gene Medicine 17.8-9 (2015): 182-183.

Lusis, M., Li, J., Ineson, J., Christensen, M. E., Rice, A. and Little, M. H. (2010). Isolation of clonogenic, long-term self renewing embryonic renal stem cells. Stem Cell Res, 5, 23-39.

Marro, S., Pang, Z. P., Yang, N., Tsai, M. C., Qu, K., Chang, H. Y., Sudhof, T. C. and Wernig, M. (2011). Direct lineage conversion of terminally differentiated hepatocytes to functional neurons. Cell Stem Cell, 9, 374-82.

Marschner, J. A., Schafer, H., Holderied, A. and Anders, H. J. (2016). Optimizing Mouse Surgery with Online Rectal Temperature Monitoring and Preoperative Heat Supply. Effects on Post-Ischemic Acute Kidney Injury. PLoS One, 11, e0149489.

Mcmahon, A. P., Aronow, B. J., Davidson, D. R., Davies, J. A., Gaido, K. W., Grimmond, S., Lessard, J. L., Little, M. H., Potter, S. S., Wilder, E. L., et al. (2008). GUDMAP: the genitourinary developmental molecular anatomy project. J Am Soc Nephrol, 19, 667-71.

Morizane, R. and Bonventre, J. V. (2017). Generation of nephron progenitor cells and kidney organoids from human pluripotent stem cells. Nat Protoc, 12, 195-207.

Morizane, R., Lam, A. Q., Freedman, B. S., Kishi, S., Valerius, M. T. and Bonventre, J. V. (2015). Nephron organoids derived from human pluripotent stem cells model kidney development and injury. Nat Biotechnol, 33, 1193-200.

(56) References Cited

OTHER PUBLICATIONS

O'brien, L. L., Guo, Q., Lee, Y., Tran, T., Benazet, J. D., Whitney, P. H., Valouev, A. and Mcmahon, A. P. (2016). Differential regulation of mouse and human nephron progenitors by the Six family of transcriptional regulators. Development, 143, 595-608.

Ohto, H., Kamada, S., Tago, K., Tominaga, S. I., Ozaki, H., Sato, S. and Kawakami, K. (1999). Cooperation of six and eya in activation of their target genes through nuclear translocation of Eya. Mol Cell Biol, 19, 6815-24.

Oliveira Arcolino, F., Tort Piella, A., Papadimitriou, E., Bussolati, B., Antonie, D. J., Murray, P., Van Den Heuvel, L. and Levtchenko, E. (2015). Human Urine as a Noninvasive Source of Kidney Cells. Stem Cells Int, 2015, 362562.

Oxburgh, Leif, et al. "(Re) Building a kidney." Journal of the American Society of Nephrology 28.5 (2017): 1370-1378.

Park, J. S., Ma, W., O'brien, L. L., Chung, E., Guo, J. J., Cheng, J. G., Valerius, M. T., Mcmahon, J. A., Wong, W. H. and Mcmahon, A. P. (2012). Six2 and Wnt regulate self-renewal and commitment of nephron progenitors through shared gene regulatory networks. Dev Cell, 23, 637-51.

Pignoni, F., Hu, B., Zavitz, K. H., Xiao, J., Garrity, P. A. and Zipursky, S. L. (1997). The eye-specification proteins So and Eya form a complex and regulate multiple steps in *Drosophila* eye development. Cell, 91, 881-91.

Plisov, S. Y., Yoshino, K., Dove, L. F., Higinbotham, K. G., Rubin, J. S. and Perantoni, A. O. (2001). TGF beta 2, LIF and FGF2 cooperate to induce nephrogenesis. Development, 128, 1045-57.

Pode-Shakked, N., Gershon, R., Tam, G., Omer, D., Gnatek, Y., Kanter, I., Oriel, S., Katz, G., Harari-Steinberg, O., Kalisky, T., et al. (2017). Evidence of In Vitro Preservation of Human Nephrogenesis at the Single-Cell Level. Stem Cell Reports, 9, 279-291.

Ritchie, M. E., Phipson, B., Wu, D., Hu, Y., Law, C. W., Shi, W. and Smyth, G. K. (2015). limma powers differential expression analyses for RNA-sequencing and microarray studies. Nucleic Acids Res, 43, e47.

Robinson, M. D. and Oshiack, A. (2010). A scaling normalization method for differential expression analysis of RNA-seq data. Genome Biol, 11, R25.

Rumballe, B. A., Georgas, K. M., Combes, A. N., Ju, A. L., Gilbert, T. and Little, M. H. (2011). Nephron formation adopts a novel spatial topology at cessation of nephrogenesis. Dev Biol, 360, 110-22.

Saridey, S. K., Liu, L., Doherty, J. E., Kaja, A., Galvan, D. L., Fletcher, B. S. and Wilson, M. H. (2009). PiggyBac transposon-based inducible gene expression in vivo after somatic cell gene transfer. Mol Ther, 17, 2115-20.

Savagner, P., Yamada, K. M. and Thiery, J. P. (1997). The zinc-finger protein slug causes desmosome dissociation, an initial and necessary step for growth factor-induced epithelial-mesenchymal transition. J Cell Biol, 137, 1403-19.

Saxen, L. and Sariola, H. (1987). Early organogenesis of the kidney. Pediatr Nephrol, 1, 385-92.

Self, M., Lagutin, O. V., Bowling, B., Hendrix, J., Cai, Y., Dressler, G. R. and Oliver, G. (2006). Six2 is required for suppression of nephrogenesis and progenitor renewal in the developing kidney. EMBO J, 25, 5214-28.

Song, Jeremy J., et al. "Regeneration and experimental orthotopic transplantation of a bioengineered kidney." Nature medicine 19.5 (2013): 646.

Taguchi, A., Kaku, Y., Ohmori, T., Sharmin, S., Ogawa, M., Sasaki, H. and Nishinakamura, R. (2014). Redefining the in vivo origin of metanephric nephron progenitors enables generation of complex kidney structures from pluripotent stem cells. Cell Stem Cell, 14, 53-67.

Takasato, M., Er, P. X., Becroft, M., Vanslambrouck, J. M., Stanley, E. G., Elefanty, A. G. and Little, M. H. (2014). Directing human embryonic stem cell differentiation towards a renal lineage generates a self-organizing kidney. Nat Cell Biol, 16, 118-26.

Takasato, M., Er, P. X., Chiu, H. S. and Little, M. H. (2016). Generation of kidney organoids from human pluripotent stem cells. Nat Protoc, 11, 1681-92.

Takasato, Minoru, Jessica M. Vanslambrouck, and Melissa H. Little. "Reprogramming somatic cells to a kidney fate." In Seminars in nephrology, vol. 34, No. 4, pp. 462-480. WB Saunders, 2014.

Tanigawa, S., Sharma, N., Hall, M. D., Nishinakamura, R. and Perantoni, A. O. (2015). Preferential Propagation of Competent SIX2+ Nephronic Progenitors by LIF/ROCKi Treatment of the Metanephric Mesenchyme. Stem Cell Reports, 5, 435-47.

Tanigawa, S., Taguchi, A., Sharma, N., Perantoni, A. O. and Nishinakamura, R. (2016). Selective In Vitro Propagation of Nephron Progenitors Derived from Embryos and Pluripotent Stem Cells. Cell Rep, 15, 801-813.

Vanslambrouck, Jessica M., and Melissa H. Little. Direct transcriptional reprogramming to nephron progenitors. Current opinion in genetics & development 34 (2015): 10-16.

Vanslambrouk, J.M. et al. The Generation of a Transposon-Mediated System for Direct Transriptional REprogamming to Nephron Progenitors. The Journal of Gene Medicine, 2015, vol. 17, Abstract from Poster and Short Oral Presentation 8, pp. 210-211.

Walz, A. L., Ooms, A., Gadd, S., Gerhard, D. S., Smith, M. A., Guidry Auvil, J. M., Meerzaman, D., Chen, Q. R., Hsu, C. H., Yan, C., et al. (2015). Recurrent DGCR8, DROSHA, and SIX homeodomain mutations in favorable histology Wilms tumors. Cancer Cell, 27, 286-97.

Weber, S., Taylor, J. C., Winyard, P., Baker, K. F., Sullivan-Brown, J., Schild, R., Knuppel, T., Zurowska, A. M., Caldas-Alfonso, A., Litwin, M., et al. (2008). SIX2 and BMP4 mutations associate with anomalous kidney development. J Am Soc Nephrol, 19, 891-903.

Wegert, J., Ishaque, N., Vardapour, R., Georg, C., Gu, Z., Bieg, M., Ziegler, B., Bausenwein, S., Nourkami, N., Ludwig, N., et al. (2015). Mutations in the SIX1/2 pathway and the DROSHA/DGCR8 miRNA microprocessor complex underlie high-risk blastemal type Wilms tumors. Cancer Cell, 27, 298-311.

Woltjen, K., Michael, I. P., Mohseni, P., Desai, R., Mileikovsky, M., Hamalainen, R., Cowling, R., Wang, W., Liu, P., Gertsenstein, M., et al. (2009). piggyBac transposition reprograms fibroblasts to induced pluripotent stem cells. Nature, 458, 766-70.

Woodard, L. E. and Wilson, M. H. (2015). piggyBac-ing models and new therapeutic strategies. Trends Biotechnol, 33, 525-33.

Woodard, L. E., Cheng, J., Welch, R. C., Williams, F. M., Luo, W., Gewin, L. S. and Wilson, M. H. (2017). Kidney-specific transposon-mediated gene transfer in vivo. Sci Rep, 7, 44904.

Woodard, L. E., Li, X., Malani, N., Kaja, A., Hice, R. H., Atkinson, P. W., Bushman, F. D., Craig, N. L. and Wilson, M. H. (2012). Comparative analysis of the recently discovered hAT transposon TcBuster in human cells. PLoS One, 7, e42666.

Xu, J. and Xu, P. X. (2015). Eya-six are necessary for survival of nephrogenic cord progenitors and inducing nephric duct development before ureteric bud formation. Dev Dyn, 244, 866-73.

Xu, P. X., Zheng, W., Huang, L., Maire, P., Laclef, C. and Silvius, D. (2003). Six1 is required for the early organogenesis of mammalian kidney. Development, 130, 3085-94.

Yusa, K., Zhou, L., Li, M. A., Bradley, A. and Craig, N. L. (2011). A hyperactive piggyBac transposase for mammalian applications. Proc Natl Acad Sci U S A, 108, 1531-6.

Zhou, T., Benda, C., Dunzinger, S., Huang, Y., Ho, J. C., Yang, J., Wang, Y., Zhang, Y., Zhuang, Q., Li, Y., et al. (2012). Generation of human induced pluripotent stem cells from urine samples. Nat Protoc, 7, 2080-9.

International Search Report and Written Opinion dated Aug. 7, 2018, from International Application No. PCT/AU2018/050502, 9 pages.

A

B

GENETICALLY INDUCED NEPHRON PROGENITORS

FIELD

THIS INVENTION relates to renal progenitor cells. More particularly this invention relates to the expression of a selected set of genes that induce renal progenitor activity in cells that do not normally have renal progenitor activity.

BACKGROUND

Chronic kidney disease (CKD) is a complex disease of increasing incidence globally (Jha et al., 2013). The rising financial strain of this disease on healthcare systems worldwide, coupled with inadequate treatment options and a steady decline in suitable donor organs, highlights the need for novel treatment options. Progress in this field has been hindered by the complex cellular structure of the mature human kidney, consisting of at least 26 different cells types (Al-Awqati et al., 2002) that not only make up the one millions functional filtration units of the renal parenchyma, the nephrons, but also the stromal and vascular components of the organ. During mammalian development, these multiple kidney cell types are derived from two main progenitor pools; the ureteric bud (UB) and the mesenchymal nephron progenitors (NPs). Through a series of reciprocal inductive signals between these populations, the UB branches to form an intricate collecting duct system for drainage of urine, whilst the NPs undergo an epithelial-to-mesenchymal transition (EMT) to form nephrons (reviewed in (Saxen et al., 1987)). Each nephron is segmented from proximal to distal ends with respect to structure and function. This organization allows differential absorption of nutrients and elimination of waste products as the blood filtrate passes from the glomerulus into the proximal tubules, Loop of Henle and distal tubules, before emptying into the collecting duct as urine. Despite the critical role played by the NP population, these cells exist only transiently during mammalian development, with nephrogenesis ceasing near the time of birth following a final burst of nephron formation (Rumballe et al., 2011). The multipotent NP population is not subsequently replenished and no further nephron formation occurs after birth (Hartman et al., 2007). As a result, any reduction in nephrogenesis prior to birth leads to a permanent reduction in nephron number which is known to negatively impact renal function and may lead to CKD later in life. Human NPs are an ideal candidate cell type for kidney regenerative therapies due to their capacity to give rise to all segments of the mammalian nephron. Whilst isolation of putative NPs from human fetal kidneys has been reported (Harari-Steinberg et al., 2013, Da Sacco et al., 2016), this is unlikely to represent a feasible clinical solution given complications around ethics, availability and access. Recently, there has been great interest around the generation of human NPs from pluripotent cell sources using stepwise directed differentiation protocols (Lam et al., 2014, Taguchi et al., 2014, Takasato et al., 2014, Imberti et al., 2015, Morizane et al., 2015, Morizane et al., 2017), including our own studies showing the generation of kidney organoids (Takasato et al., 2014, Takasato et al., 2016). While such protocols generate cells possessing phenotypic characteristics of bona fide human NPs, including a capacity to form segmented nephron structures, they lack evidence for a domain of self-renewing NPs as is required for continued nephrogenesis.

SUMMARY

The present invention is broadly directed to the expression of SIX1, EYA1 and SNAI2 genes in a cell to induce said cell to have nephron progenitor potential, activity and/or a nephron progenitor phenotype. Typically, the cell does not normally have nephron progenitor potential or activity, or has minimal, insubstantial or insufficient nephron progenitor potential or activity.

The present inventors have found that it is possible to efficiently re-program human cells to nephron progenitors (NPs) using three transcription factors (SNAI2, EYA1 and SIX1). The present inventors have also found that re-programmed NPs contribute to the formation of new nephrons in vitro, ex vivo and in vivo, and the nephron epithelium after acute kidney injury.

An aspect of the invention provides an isolated cell having nephron progenitor potential, said isolated cell comprising at least one exogenous nucleic acid that comprises a nucleotide sequence of a SNAI2 gene, an EYA1 gene and a SIX1 gene, or respective fragments thereof, and that are expressible at a level that induces said isolated cell to have nephron progenitor activity.

A related aspect of the invention provides an isolated cell having nephron progenitor activity, said isolated cell comprising at least one exogenous nucleic acid that comprises a nucleotide sequence of a SNAI2 gene, an EYA1 gene and a SIX1 gene, or respective fragments thereof, that are expressed at a level that induces said isolated cell to have nephron progenitor activity.

Another aspect of the invention provides a method of inducing nephron progenitor potential in a cell, tissue or organ said method including the step of administering to said cell, tissue or organ at least one exogenous nucleic acid that comprises a nucleotide sequence of a SNAI2 gene, an EYA1 gene and a SIX1 gene, or respective fragments thereof, and that are expressible at a level that can induce said cell, tissue or organ to have nephron progenitor activity.

A related aspect of the invention provides a method of inducing nephron progenitor activity in a cell, tissue or organ, said method including the step of administering to said cell, tissue or organ at least one exogenous nucleic acid that comprises a nucleotide sequence of a SNAI2 gene, an EYA1 gene and a SIX1 gene, or respective fragments thereof, and that are expressed at a level to induce said cell tissue or organ to have nephron progenitor activity.

The at least one exogenous nucleic acid may be administered to said cell, tissue or organ in vitro or in vivo.

A further aspect of the invention provides a method of producing a nephron, said method including the step of differentiating said nephron from one or more cells having nephron progenitor activity, said one or more cells each comprising at least one exogenous nucleic acid that comprises a nucleotide sequence of a SNAI2 gene, an EYA1 gene and a SIX1 gene, or respective fragments thereof, and are expressed at a level that induces said cell to have nephron progenitor activity.

Differentiating said nephron from one or more cells having nephron progenitor activity may be performed in vitro or in vivo.

Another further aspect of the invention provides a method of producing a renal structure, said method including the step of providing a plurality of cells comprising at least one exogenous nucleic acid that comprises a nucleotide sequence of a SNAI2 gene, an EYA1 gene and a SIX1 gene, or respective fragments thereof, that are expressed at a level to induce said cells to have nephron progenitor activity, and/or producing one or more renal cells or tissues from said cells, to thereby produce the renal structure.

The renal structure may be produced in vitro or in vivo.

Suitably, the SNAI2 gene, the EYA1 gene and the SIX1 gene are not expressed in the one or more renal cells or tissues. The one or more renal cells or tissues obtained from said cell may include nephrons and, optionally, one or more other renal cells or tissues in addition to the nephrons.

A still further aspect of the invention provides a method of treating or preventing a renal disease, disorder or condition in a mammal, said method including the step of administering to the mammal at least one exogenous nucleic acid that comprises a nucleotide sequence of a SNAI2 gene, an EYA1 gene and a SIX1 gene, or respective fragments thereof, that are expressed at a level to induce a cell to have nephron progenitor activity, or a cell comprising said at least one exogenous nucleic acid and/or one or more renal cells or tissues obtained from said cell, to thereby treat or prevent the renal disease, disorder or condition in the mammal.

The one or more renal cells or tissues obtained from said cell may include nephrons and, optionally, one or more other renal cells or tissues in addition to the nephrons.

A still yet further aspect of the invention provides a genetic construct comprising at least one exogenous nucleic acid that comprises a nucleotide sequence of a SNAI2 gene, an EYA1 gene and a SIX1 gene, or respective fragments thereof, that are expressible at a level in a cell that induces said cell to have nephron progenitor activity.

A related aspect of the invention provides a non-human mammal comprising one or a plurality of cells that comprise at least one exogenous nucleic acid that comprises a nucleotide sequence of a SNAI2 gene, an EYA1 gene and a SIX1 gene, or respective fragments thereof, and that are expressible, or are expressed, at a level that induces said cell to have nephron progenitor activity.

Suitably, according to the aforementioned aspects, in the absence of expression of the SNAI2 gene, the EYA1 gene and the SIX1 gene the cell, tissue or organ does not normally have nephron progenitor potential or activity, or has minimal, insubstantial or insufficient nephron progenitor potential or activity.

Suitably, according to the aforementioned aspects the exogenous nucleic acid does not include a nucleotide sequence of a SIX2, HOXA11 and/or an OSR1 gene.

In some embodiments of the aforementioned aspects, the nucleotide sequence of the SNAI2 gene, the EYA1 gene and the SIX1 gene, or respective fragments thereof, are present in the same genetic construct. In these embodiments, there may be stoichiometric expression of each of the genes.

In some embodiments of the aforementioned aspects, the genetic construct is inducible, repressible or otherwise regulatable. In this embodiment, expression of the SNAI2 gene, the EYA1 gene and the SIX1 gene may be controlled. As one example, the construct may be induced to re-program the cells, and subsequently down-regulated to allow differentiation of the re-programmed cells.

In some embodiments of the aforementioned aspects, said at least one exogenous nucleic acid is/are present in a transposon-based genetic construct. Suitably, the transposon-based genetic construct is integrated into the genome of said isolated cell.

Throughout this specification, unless otherwise indicated, "comprise", "comprises" and "comprising" are used inclusively rather than exclusively, so that a stated integer or group of integers may include one or more other non-stated integers or groups of integers.

It will also be appreciated that the indefinite articles "a" and "an" are not to be read as singular indefinite articles or as otherwise excluding more than one or more than a single subject to which the indefinite article refers. For example, "a" protein includes one protein, one or more proteins or a plurality of proteins.

Transposon plasmids contain the piggyBac 3' and 5' terminal repeats (pb3'TR, pb5'TR) flanking the transposon sequence to be integrated permanently into the genome. Abbreviations are as follows: CMV (cytomegalovirus, constitutive viral promoter); rtTA-advanced (advanced reverse tetracycline transactivator protein); SV40 pA (SV40 virus polyadenylation signal); ori (origin of replication); AmpR (ampicillin resistance gene); Tight TRE promoter (tight tetracycline response element promoter); EF-1α promoter (Elongation Factor-1α, constitutive endogenous promoter); HA (N-terminal hemagglutinin tag). White colouring depicts non-transposon portions of the vectors, while black and grey depicts integrating portions of the transposons. Refer to Table 1 for reprogramming factor accession numbers.

Figure 2:
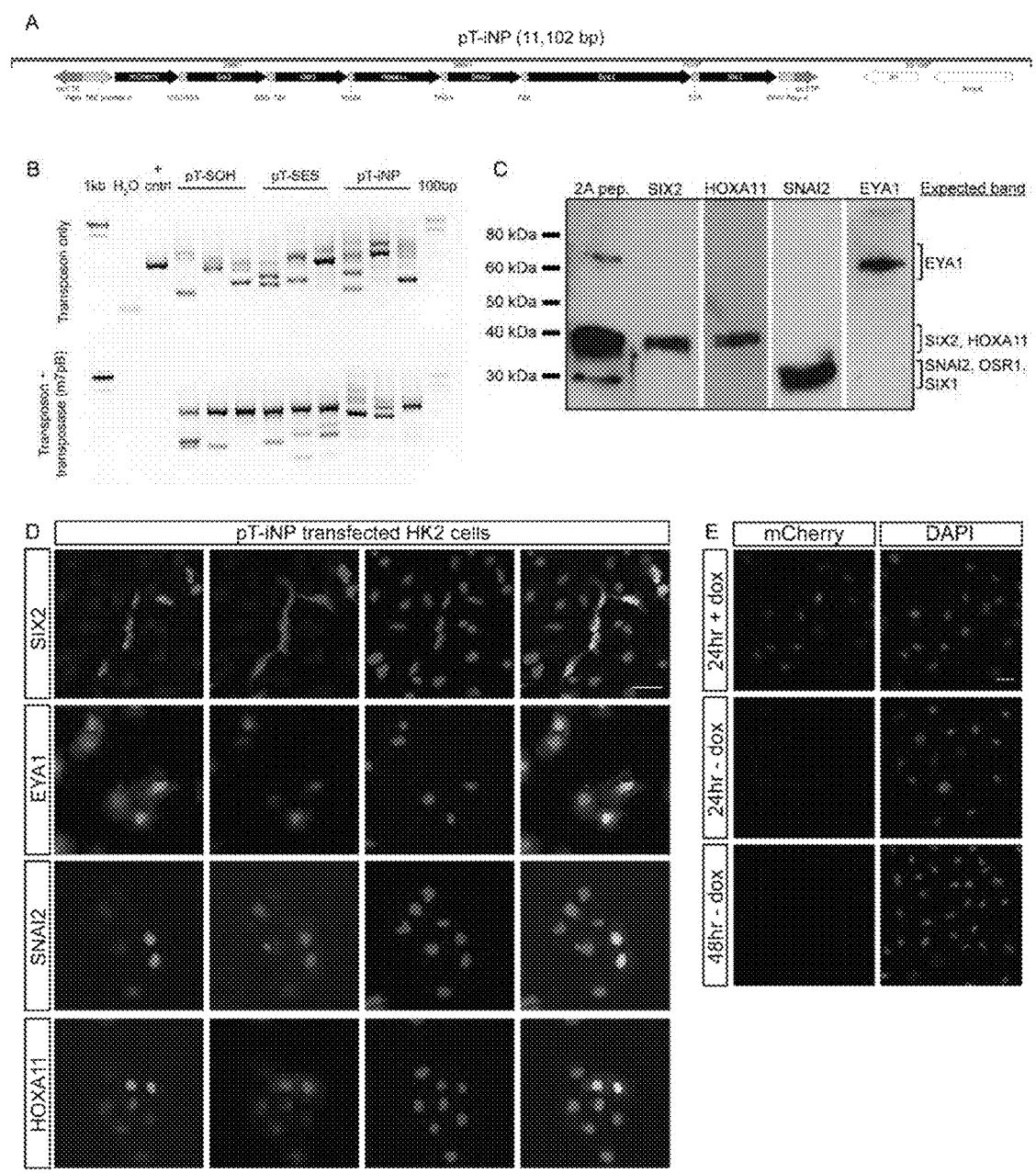

FIG. 2: Validation of Reprogramming Transposon Functionality. Validation of Reprogramming Transposon Functionality.

(A) pT-iNP plasmid map showing the six reprogramming factors (SIX2, OSR1, HOXA11, SNAI2, EYA1 and SIX1 [refer to Table 1 for gene details]) separated by 2A sequences (GSG-T2A, Pm2A, Tm2A, F2A and E2A [refer to Table S2]) and additional features (3' and 5' terminal repeats; pb3'TR and pb5'TR, Tight tetracycline response element promoter; Tight TRE promotor, SV40 virus polyadenylation signal; SV40 poly-A, origin of replication; ori and ampicillin resistance gene; AmpR). (B) Excision PCR assay to detect effective transposon removal from the three reprogramming transposon plasmids (pT-SOH, pT-SES and pT-iNP) by the transposase (pEF-1α-m7pB). HK2 cells transfected with either pT-SOH or pT-SES and pEF-1α-m7pB gave the desired product size in each lane (strong upper band). pT-iNP produced bands of different sizes in the presence of the transposase, indicating poor fidelity of excision of the large six-factor transposon from the plasmid backbone. (C) Western blot assessment of 2A-mediated cleavage in HK2 cells transfected with pT-iNP, demonstrating only the expected band sizes when probed for the residual 2A sequences that remain bound to each protein following cleavage and/or for the reprogramming factor-specific antibodies where available. (D) Immunofluorescence of pT-iNP-transfected HK2 cells demonstrating correct nuclear localization of reprogramming factors (green) in mCherry-expressing cells (red). Scale bar represents 30 μm. (E) Immunofluorescence of pT-iNP-transfected HK2 cells demonstrating mCherry expression (red) after 24 hours of doxycycline exposure and the decline in this expression 24 hours and 48 hours post-doxycycline removal. Scale bar represents 30 μm.

Figure 3:
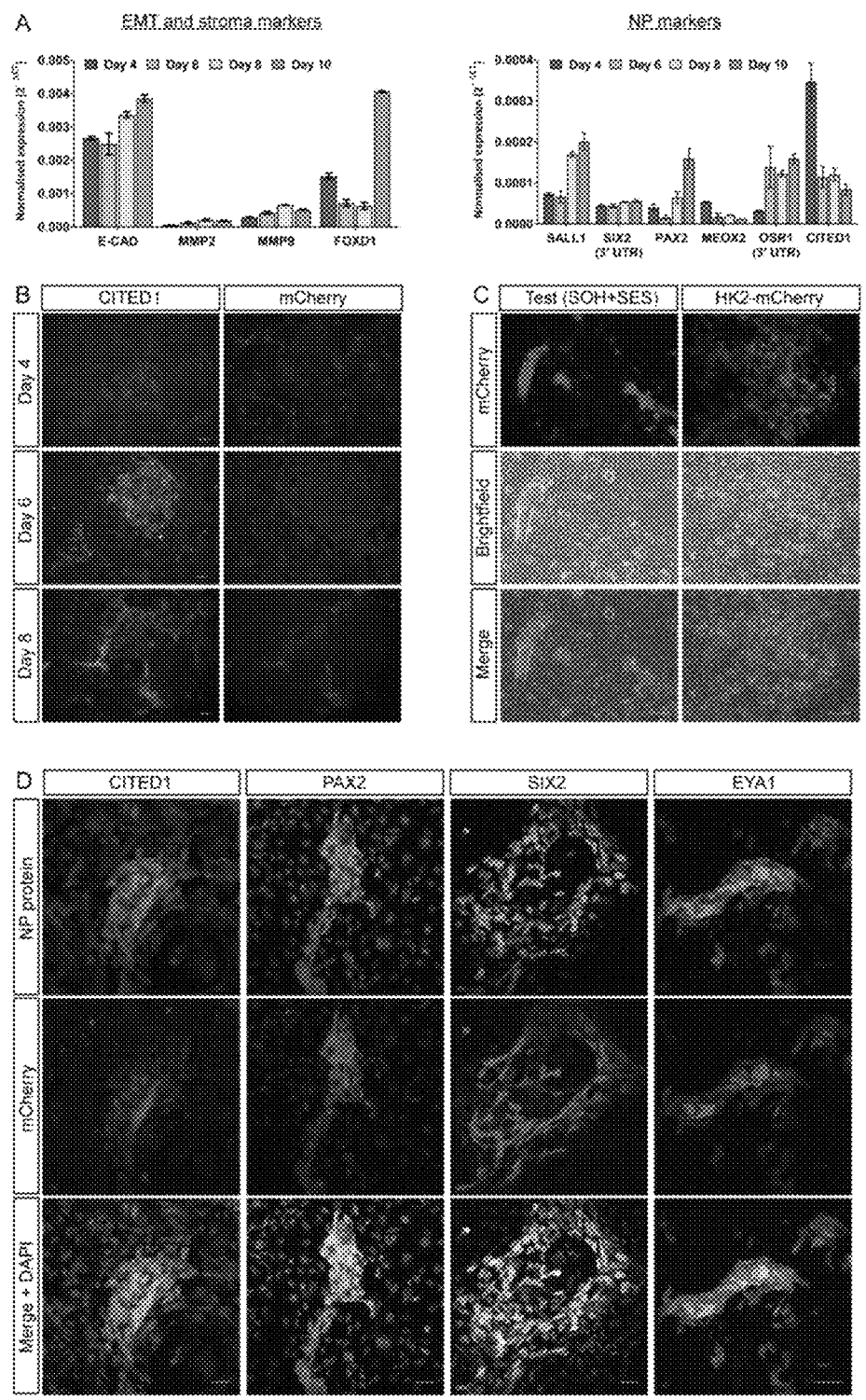

FIG. 3: HK2 Cells Show Evidence of Reprogramming In Vitro when Transfected with the Reprogramming Transposons, pT-SOH and pT-SES.

(A) Quantitative RT-PCR (qRT-PCR) time course analysis of EMT, stoma and NP genes in HK2 cells undergoing reprogramming for 4, 6, 8 and 10 days. Data are presented as mean±SEM. (B) CITED1 immunofluorescence time course analysis of HK2 cells from (A), depicting CITED1 and mCherry expression at days 4, 6 and 8 of reprogramming. Scale bars represent 500 μm. (C) Brightfield and fluorescence images of test (transfected with reprogramming transposons) and control (expressing mCherry only) HK2 cells after 8 days of reprogramming. Scale bars represent 500 μm. (D) Immunofluorescence of NP proteins in reprogramming transposon-transfected cells following 8 days of reprogramming. Scale bars represent 30 μm.

Figure 4:
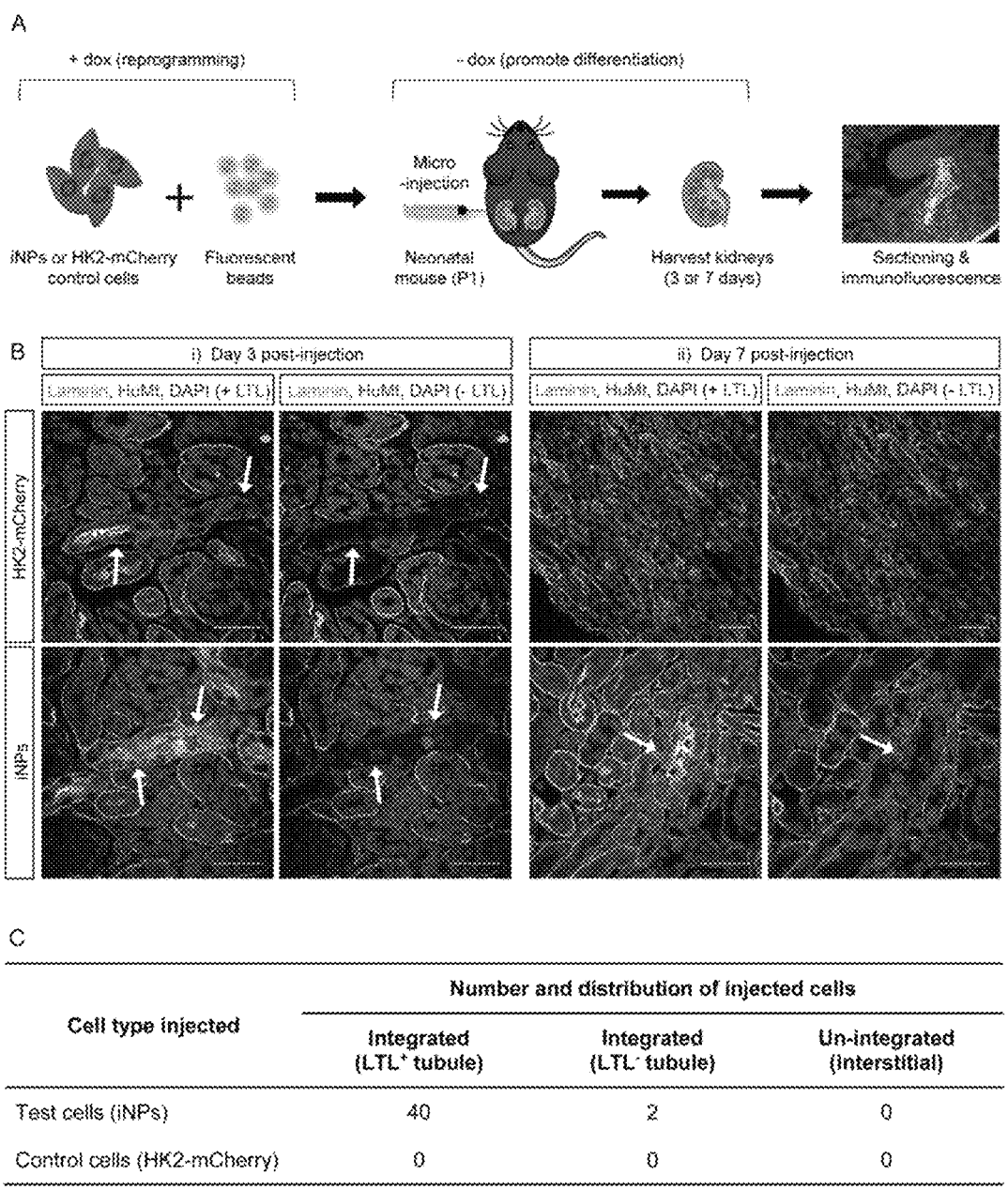
Figure 4:
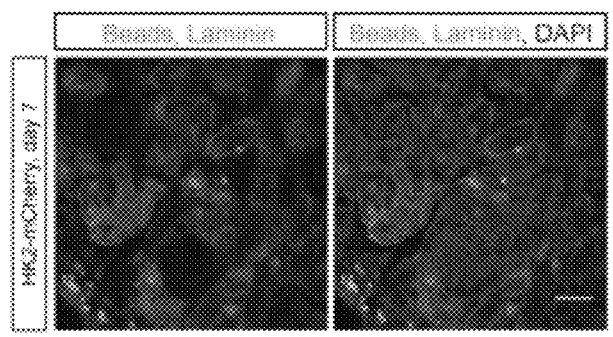

FIG. 4: iNPs Contribute to Nephrons in Mouse Kidney In Vivo.

(A) Schematic of the neonatal injection assay used to determine iNP differentiation capacity. (B) Immunofluorescence of sections through mouse kidneys at 3 and 7 days post-injection with iNPs or control HK2-mCherry cells (stained with HuMt, red). Arrows depict examples of integrated HuMt+ cells or HuMt+ tubules. Scale bars represent 30 μm. (C) Quantification of integration events in kidneys injected with either iNPs or HK2-mCherry control cells and harvested 7 days post-injection. (D) Immunofluorescence analysis and detection of bead auto-fluorescence in neonatal kidneys injected with HK2-mCherry control cells and harvested 7 days post-injection. Scale bars represent 30 μm.

Figure 5:
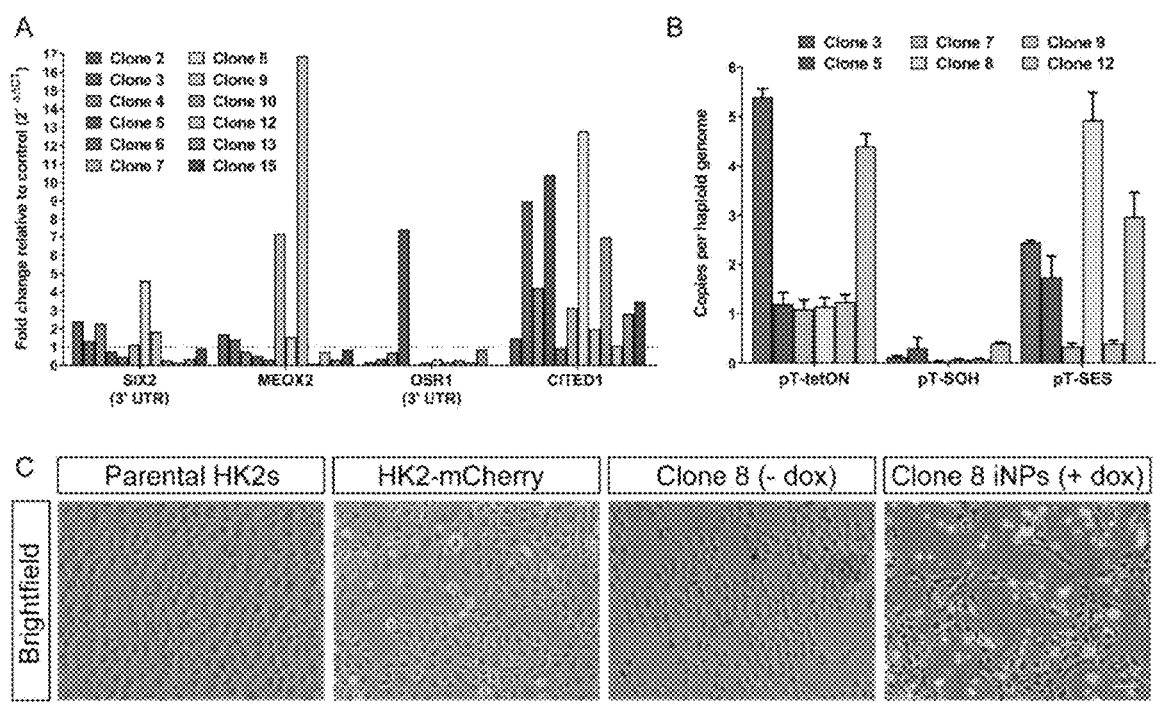

FIG. 5: Reprogramming to iNPs Requires Only Three Factors, SNAI2, EYA1 and SIX1.

(A) qRT-PCR analysis of NP-specific gene expression in 12 clones derived from HK2 cells transfected with pT-SOH and pT-SES following 8 days of doxycycline exposure in HGM. (B) Quantitative PCR (qPCR) analysis of genomic DNA from six clones of interest from (A), showing transposon copy number for the reprogramming (pT-SOH and pT-SES) and tetracycline activator (pT-TetON) transposons. Data are presented as mean±SEM. (C) Brightfield images comparing the morphology of parental HK2 cells with HK2-mCherry control cells, HK2-derived Clone 8 cells prior to doxycycline addition (Clone 8−dox) and the same Clone 8 cells following reprogramming (Clone 8 iNPs+dox). Scale bar represents 100 μm.

Figure 6:
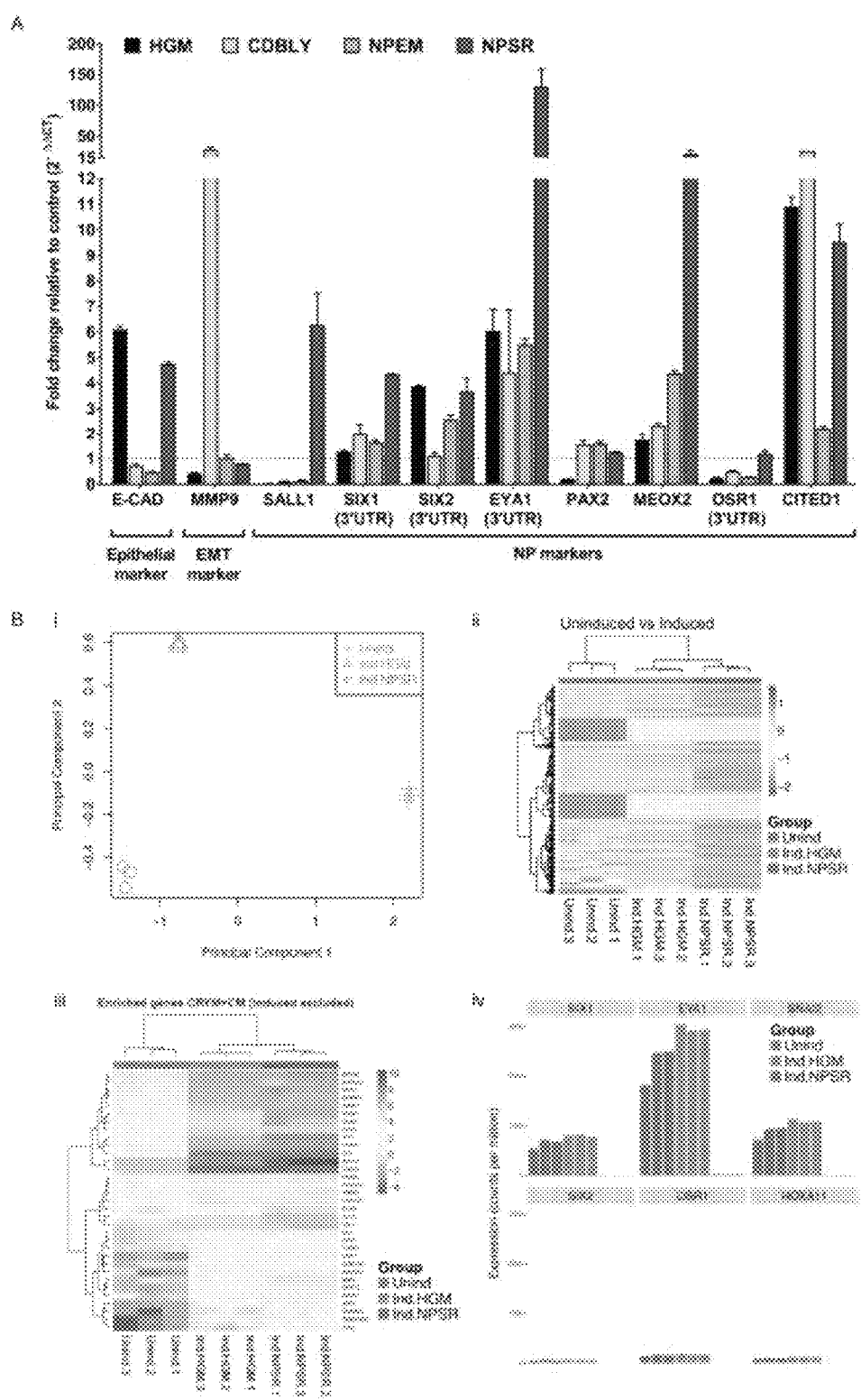

FIG. 6: Reprogramming to iNPs is Supported by NP-Specific Maintenance Media.

(A) qRT-PCR analysis of NP markers in Clone 8-derived iNPs relative to HK2-mCherry control cells in HGM. Data are presented as mean±SEM. (B) qRT-PCR analysis of NP markers in Clone 8-derived iNPs relative to iPSC-derived renal progenitors. Data are presented as mean±SEM. (C) Brightfield images comparing the effects of 3D culture on iNPs cultured in HGM and NPSR, as well as HK2-mCherry control cells cultured in NPSR. Scale bars represent 100 μm. (D) RNA-Seq analyses comparing uninduced Clone 8 control cells (blue) with induced Clone 8 iNPs cultured in HGM (red) and NPSR (green), with n=3 for each condition, showing (i) the principle component analysis of separation between induced and uninduced conditions, (ii) TREAT analysis heatmap showing relative expression levels of genes identified as significantly differentially expressed between the uninduced and induced conditions (log 2 threshold>1, FDR<0.05), with expression row scaled to a mean of 0 and standard deviation of 1, (iii) heatmap of gene expression (log 2 counts per million) for cap mesenchyme/Crym-enriched cap mesenchyme markers, excluding genes present in the reprogramming transposon (SIX1, EYA1 and SNAI2), and (iv) expression levels (counts per million) of the 6 genes in the transposons, SES (SIX1, EYA1 and SNAI2; top row) and SOH (SIX2, OSR1 and HOXA11; bottom row).

Figure 7:
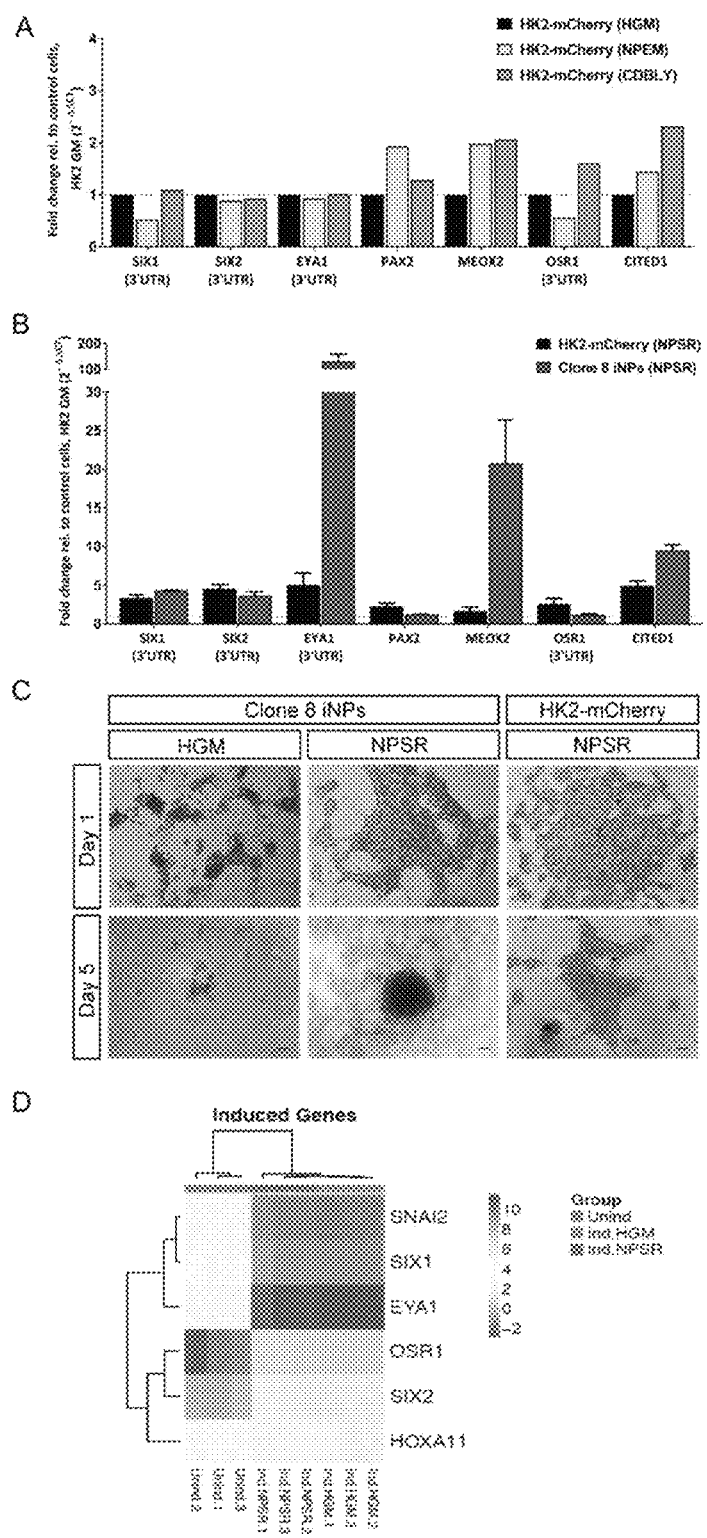

FIG. 7: Poor induction of NP genes in NP media alone without reprogramming transposon integration and improved NP behavioral characteristics of iNP-like cells cultured in NPSR. (A) qRT-PCR analysis of NP gene expression in HK2-mCherry control cells exposed to normal HGM, NPEM and CDBLY. (B) qRT-PCR analysis of NP gene expression in HK2-mCherry control cells and iNP-like cells cultured in NPSR. Data are presented as mean±SEM. (C) Brightfield images comparing the effects of 3D culture on iNP-like cells cultured in HGM and NPSR, as well as HK2-mCherry control cells cultured in NPSR. Scale bars represent 100 μm. (D) Heatmap generated from RNA-Seq analyses of uninduced Clone 8 control cells (blue) and induced Clone 8 iNP-like cells cultured in HGM (red) and NPSR (n=3 for each condition) depicting the expression of genes within the two reprogramming transposons (expression represented as $\log_2$ counts per million).

Figure 8:
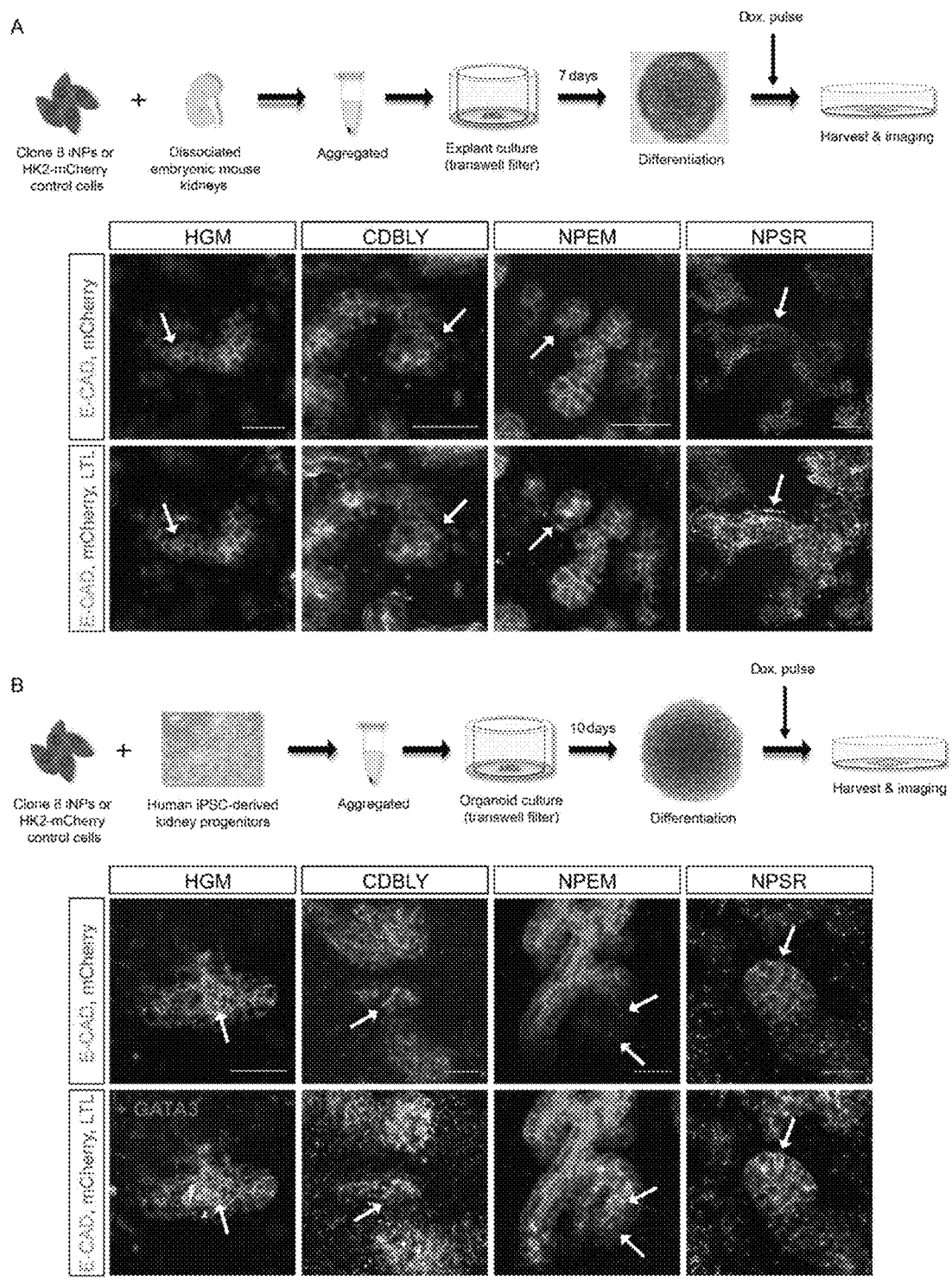

FIG. 8: Clone 8 iNPs Reprogrammed in HGM or NP-Supportive Media Show Evidence of Nephron-Forming Capacity in Mouse and Human Organoids.

(A) Schematic of the embryonic mouse kidney organoid assay and immunofluorescence demonstrating the contribution of Clone 8 iNPs to developing nephrons. Arrows in images depict examples of integrated iNPs (red). (B) Schematic of the human iPSC-derived kidney organoid assay and immunofluorescence demonstrating the contribution of Clone 8 iNPs to developing nephrons. Arrows in images depict examples of integrated iNPs (red). Scale bars in (A) and (B) represent 30 μm.

Figure 9:
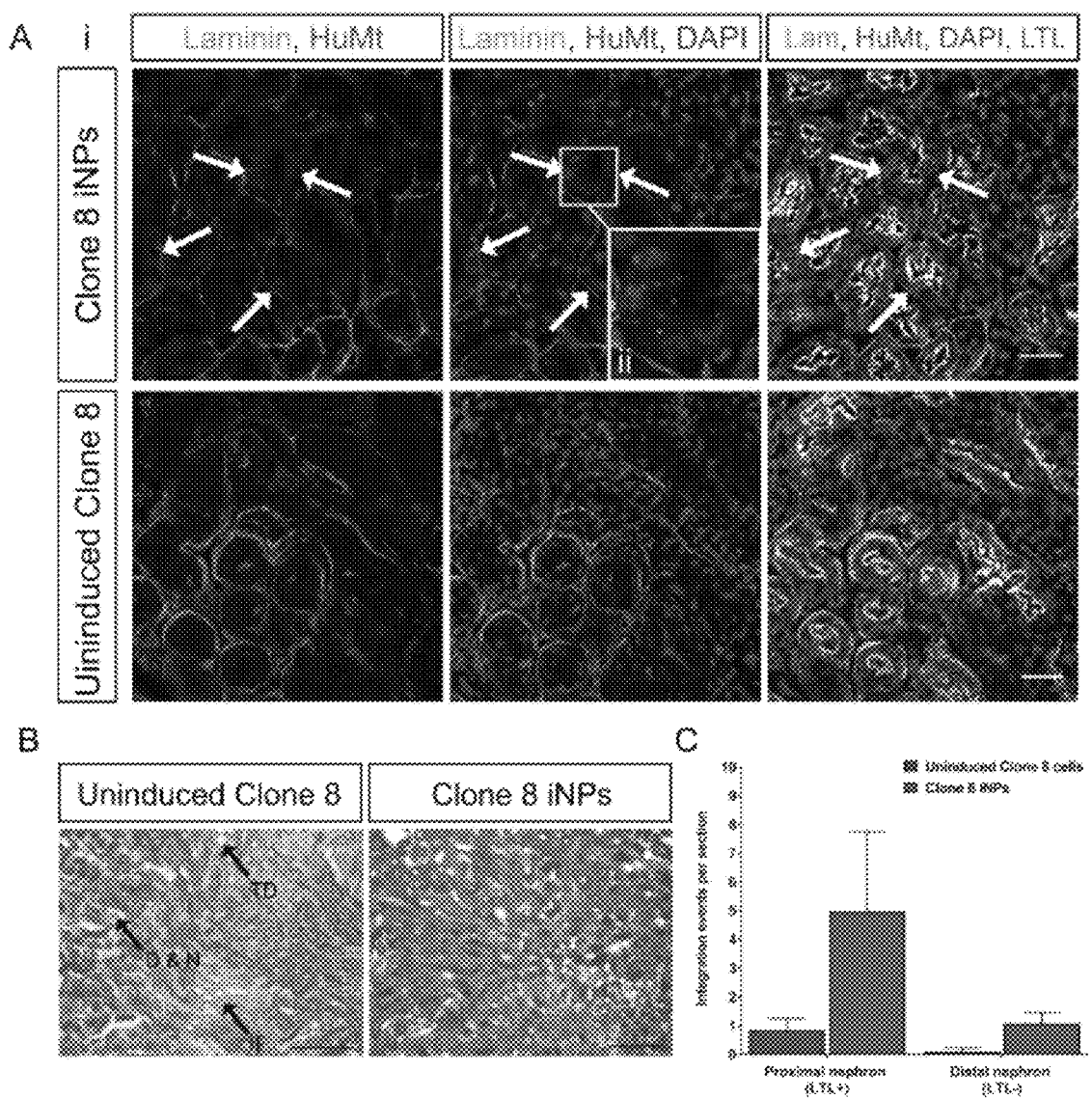

FIG. 9: Clone 8 iNPs Contribute to Adult Mouse Kidney Following Ischemia Reperfusion.

(Ai) Representative immunofluorescence images near injection sites of kidneys (10 days post-IRI and cell injection) injected with either Clone 8 iNPs or uninduced Clone 8 control cells. Arrows depict iNPs examples of iNPs stained with human mitochondrial antigen (HuMt; red) integrated into LTL-positive proximal tubules of the cortex. Scale bars represent 30 μm. (Aii) Inset of Ai (middle image, top row) showing the boxed area of HuMt-positive integrated iNPs at higher magnification. (B) PAS staining of kidneys injected with Clone 8 iNPs or uninduced Clone 8 control cells demonstrating tubule damage near injection sites 10 days post-IRI. Arrows depict examples of tubular damage in the control section (tubular cell detachment; D, necrosis; N, tubular dilation; TD, and interstitial fibrosis; IF). Scale bars represent 200 μm. (C) Quantification of the number of integrated cells (integration events) per section of kidneys injected with Clone 8 iNPs or uninduced Clone 8 control cells. Data are presented as mean±SEM (n=3).

Figure 10:
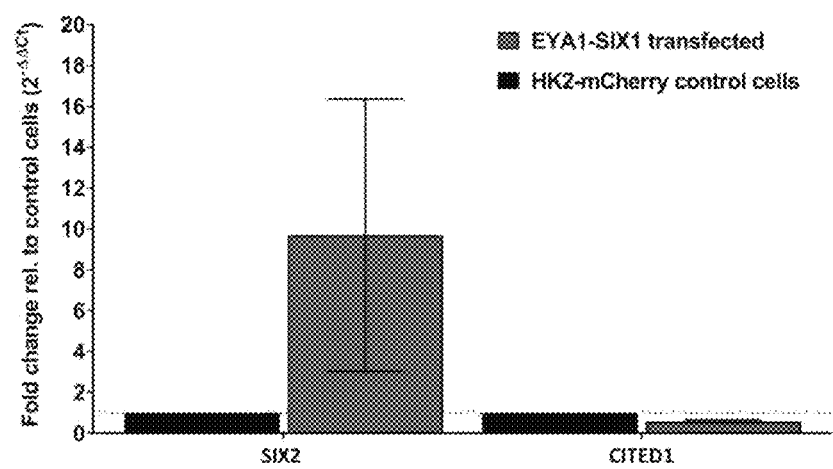

FIG. 10: Transfection with SIX1 and EYA1 Combined does not Induce Expression of CITED1.

qRT-PCR analysis of HK2 cells stably transfected with SIX1 and EYA1 compared to HK2-mCherry control cells showing reduced CITED1 expression and a large variation in SIX2 expression between replicates. Data are presented as mean±SEM.

Figure 11:
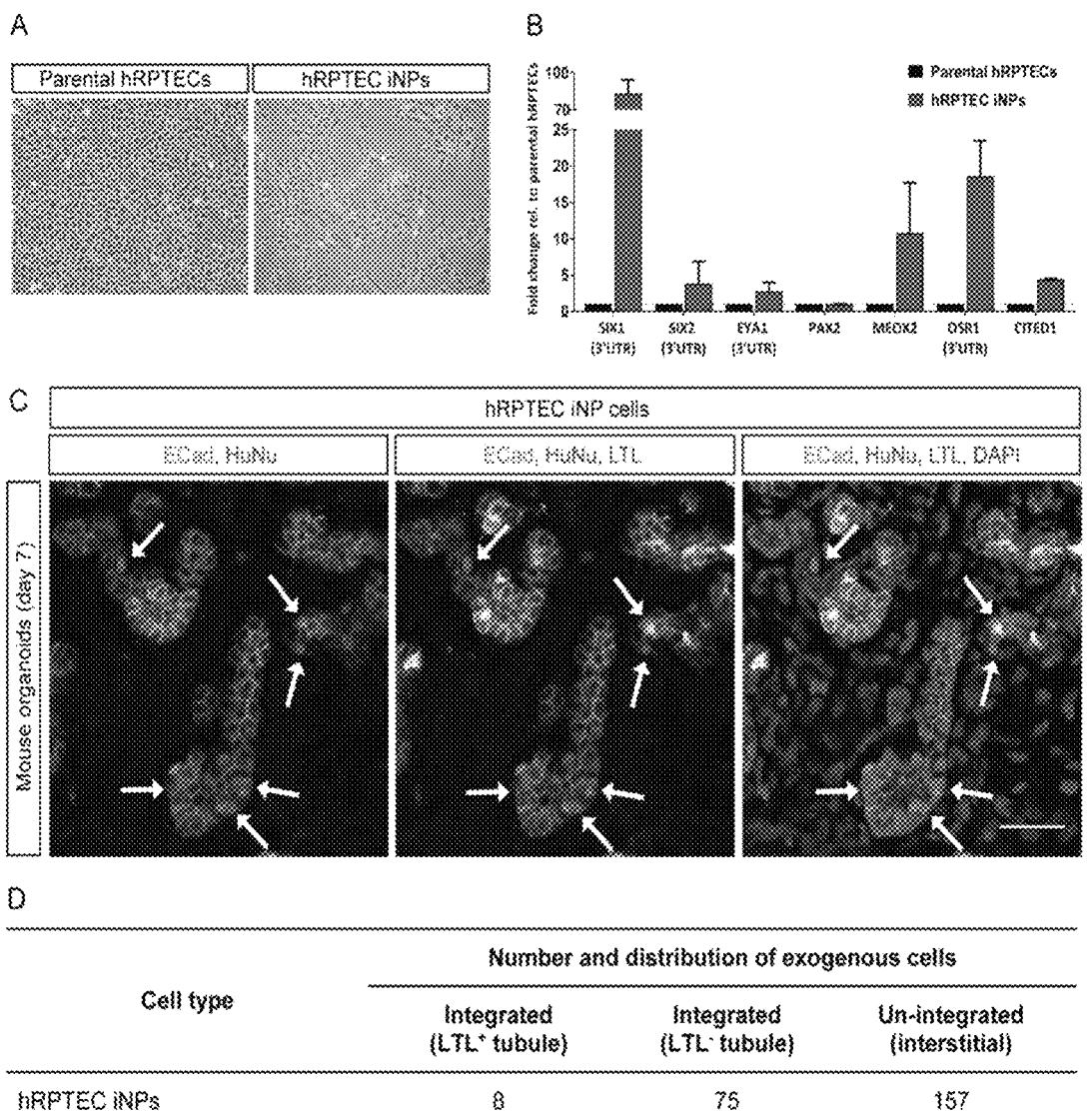

FIG. 11: Refinement of Reprogramming Factors and Conditions Enables the Generation of iNPs from Primary Human Proximal Tubule Cells (hRPTECs).

(A) Brightfield images of parental (untransfected) hRPTECs and hRPTEC iNPs that have undergone transfection with pT-SES, pT-TetON and pEF1-HA-m7pB followed by reprogramming. (B) qRT-PCR analysis of NP gene expression in hRPTEC iNPs relative to parental hRPTECs. Data are presented as mean±SEM. (C) Immunofluorescence of the mouse kidney organoid assay demonstrating the contribution of hRPTEC iNPs to developing nephrons marked by E-Cadherin (ECad; green). Arrows depict examples of integrated hRPTEC iNPs marked by human nuclear antigen (HuNu; red) and DAPI (nuclei; blue). Scale bar represents 30 µm. (D) Quantification of hRPTEC iNP integration events and interstitial cells in the mouse organoid assay from (C).

Figure 12:
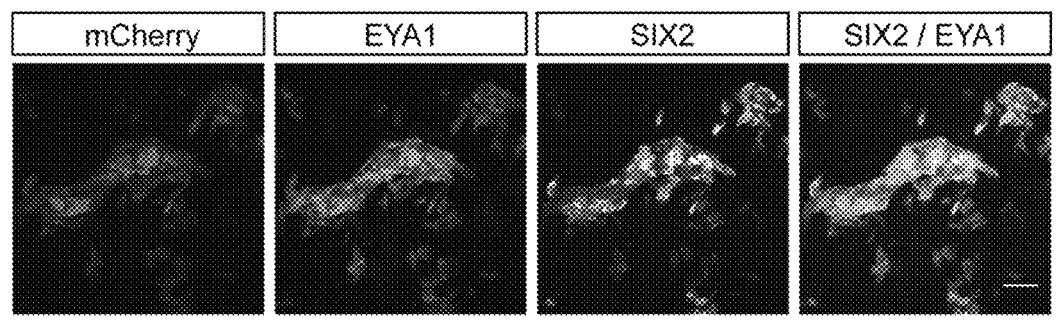
Figure 12:
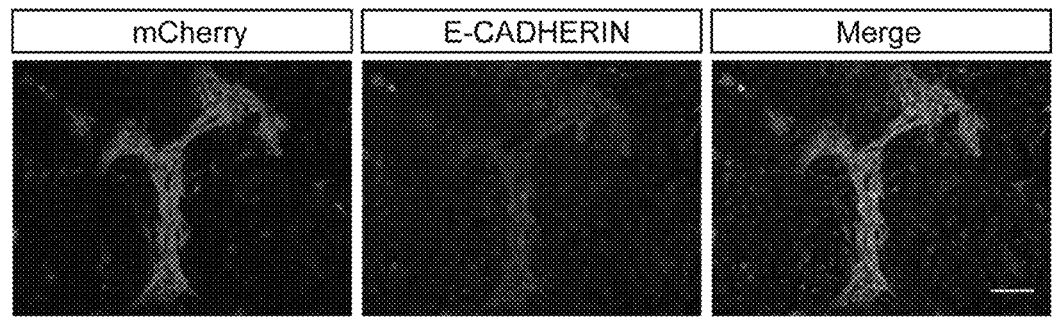

FIG. 12: Co-Localisation of NP Markers and Protein Evidence of EMT in iNPs.

(A) Immunofluorescence demonstrating co-localisation of EYA1 and SIX2 in mCherry-expressing cells following 8 days of reprogramming. Scale bar represents 30 µm. (B) Immunofluorescence demonstrating a lack of epithelial E-CADHERIN expression in mCherry-expressing structures formed by reprogrammed cells following 8 days of reprogramming. Scale bar represents 500 µm.

Figure 13:
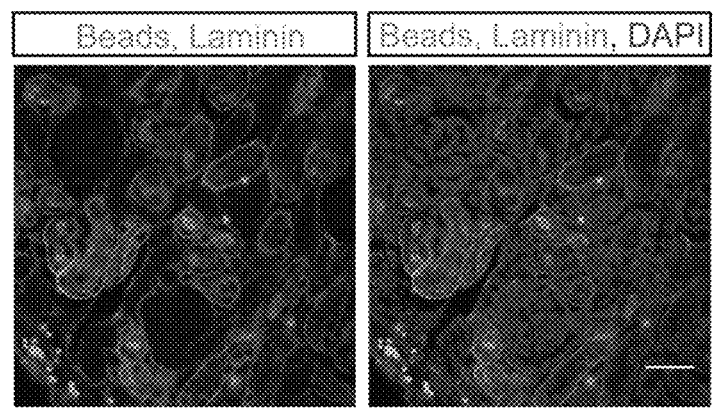

FIG. 13: Bead Distribution Demonstrates Successful Delivery of Control Cells in the Neonatal Injection Assay.

Immunofluorescence analysis and detection of bead autofluorescence in neonatal kidneys injected with HK2-mCherry control cells and harvested 7 days post-injection. Scale bars represent 30 µm.

Figure 14:
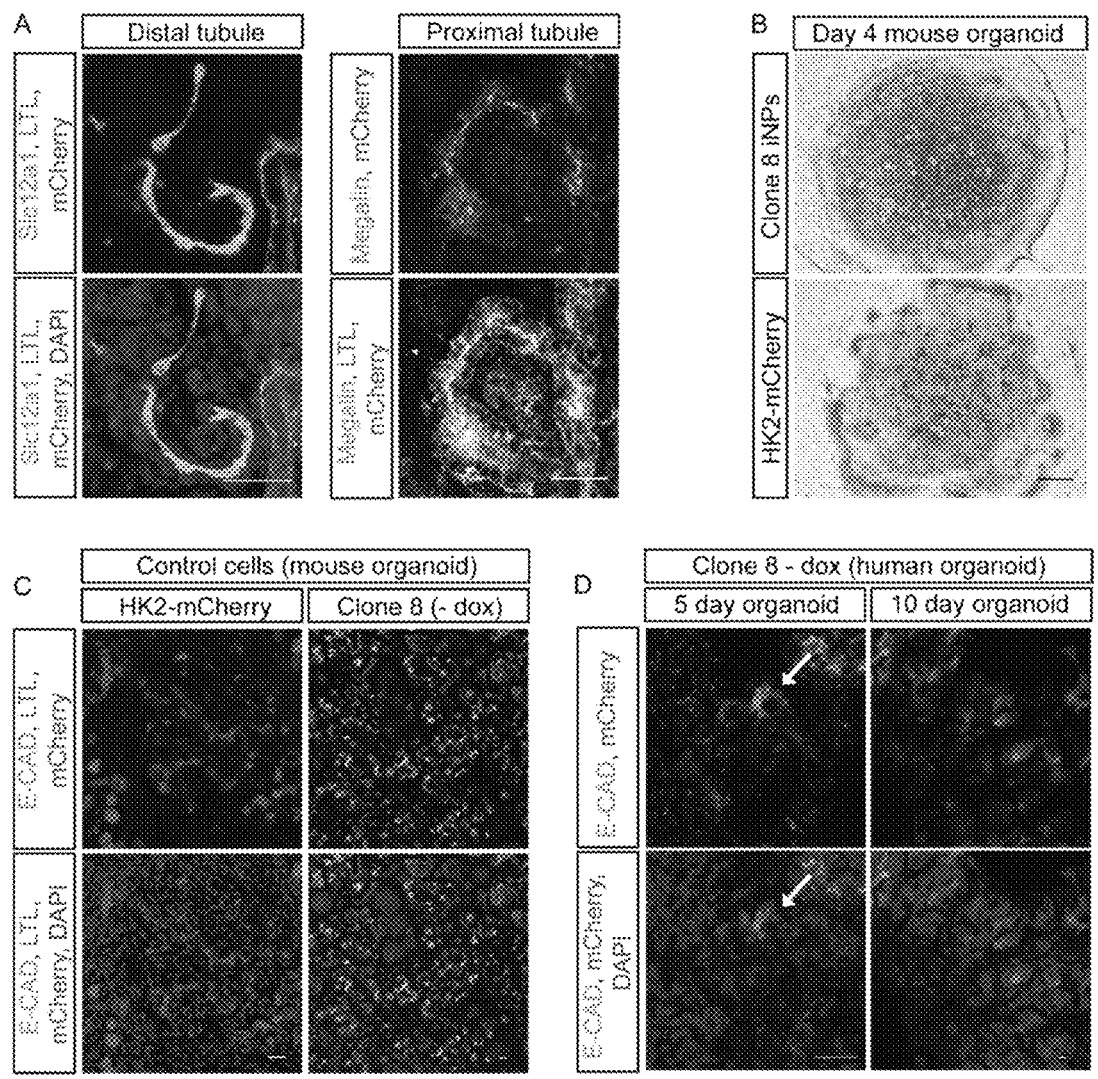

FIG. 14: Expression of Nephron Segment-Specific Proteins by Integrated Clone 8 iNP-Like Cells and Lack of Control Cell Integration in Mouse and Human Organoid Assays.

(A) Immunofluorescence of mouse kidney organoids showing Clone 8 iNP-like cells (red) integrated into distal and proximal tubules and expressing nephron segment-specific proteins of these tubules (distal; Slc12a1 [green, left], proximal; Megalin [green, right]). Scale bars represent 30 µm. (B) Brightfield images of day 4 mouse kidney organoids containing either Clone 8 iNP-like cells or HK2-mCherry control cells depicting disruption of the overall morphology of the HK2-mCherry mouse organoid. Scale bar represents 500 µm. (C) Immunofluorescence of control cells (HK2-mCherry cells and Clone 8 cells cultured without doxycycline addition [Clone 8–dox]) in mouse kidney organoids following a brief doxycycline pulse and harvest at day 7. Control cells are stained with anti-mCherry (red). Scale bars represent 30 µm. (D) Immunofluorescence of Clone 8–dox control cells in human iPSC-derived kidney organoids at days 5 and 10 following a brief doxycycline pulse. Arrow depicts an example of Clone 8–dox cells stained with anti-mCherry (red). Scale bars represent 30 µm. Images in A, B and C show cells that have been cultured in HGM and are representative of the experiment.

Figure 15:
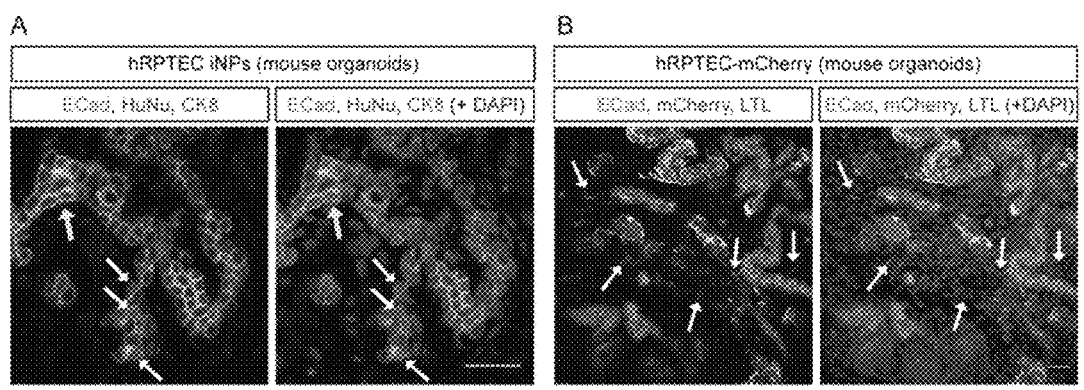

FIG. 15: Primary hRPTEC-Derived iNPs do not Integrate into Collecting Duct and Control Cells Remain Interstitial in Mouse Organoid Assays.

(A) Immunofluorescence of a mouse kidney organoid assay demonstrating a lack of hRPTEC iNPs (red) in Cytokeratin 8-(CK8) expressing collecting duct (grey, indicated by yellow arrows). While arrows depict examples of hRPTEC iNPs integrated into CK8⁻/ECad⁺ (green) segments of developing nephrons. Scale bar represents 30 µm. (B) Immunofluorescence of a mouse kidney organoid assay demonstrating the interstitial localization of hRPTEC-mCherry control cells (marked by mCherry; red) amongst developing nephrons. Arrows depict examples of hRPTEC-mCherry cells. Scale bar represents 30 µm.

Figure 16:
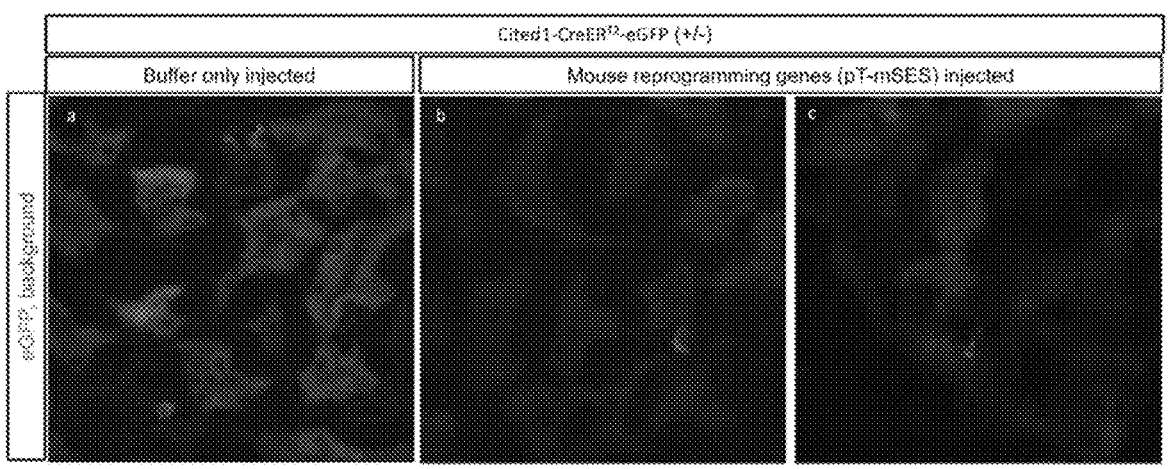

FIG. 16: In Situ Reprogramming to Cited1+ Cells Via Expression of Three Mouse Transcription Factors.

Induction of Cited1 following gene delivery of mouse Six1, Snai2, and Eya1 in vivo. Mice containing the Cited1-CreER$^{T2}$ BAC transgene express eGFP from the Cited1 promoter. Male mice that were transgenic for Cited1-Cre-ER$^{T2}$-eGFP were given renal pelvis hydrodynamic injections of pT-mSES, expressing the three mouse transcription factors Six1, Snai2 and Eya1 from the human elongation factor 1 alpha promoter with the same 2A sequences separating the genes as in the human construct pT-SES. Mice were sacrificed at 72 hours post-injection. After staining for eGFP, cells that were positive in both treated and control mice (a and b) appeared to be interstitial while other cells that are both eGFP-positive and display a more tubule-like morphology (c) were only found in the kidneys of the transposon-injected animals.

DETAILED DESCRIPTION

The invention disclosed herein has arisen, at least in part, from the identification of three (3) key genes, SNAI2, EYA1 and SIX1, which when expressed at a suitable level in a cell not normally having nephron progenitor activity, induces or "re-programs" that cell to have or subsequently develop nephron progenitor activity. In a particular embodiment, the invention provides a transposon-based expression system for inducibly expressing SNAI2, EYA1 and SIX1 genes to achieve direct transcriptional reprogramming of cells to become induced nephron progenitors. Nephron progenitors induced by expression of SNAI2, EYA1 and SIX1 may be used for the production of nephron cells and tissues that are useful in kidney regeneration, kidney transplantation, bio-printing and nephrotoxocity testing, although without limitation thereto.

Aspects of the invention provide an isolated cell having nephron progenitor potential, said isolated cell comprising at least one exogenous nucleic acid that comprises a nucleotide sequence of a SNAI2 gene, an EYA1 gene and a SIX1 gene, or respective fragments thereof, and are expressible at a level that induces said isolated cell to have nephron progenitor activity, or a method of producing same isolated cell having nephron progenitor potential.

Related aspects of the invention provide an isolated cell having nephron progenitor activity, said isolated cell comprising at least one exogenous nucleic acid that comprises a nucleotide sequence of a SNAI2 gene, an EYA1 gene and a SIX1 gene, or respective fragments thereof, and are expressed at a level that induces said isolated cell to have nephron progenitor activity, or a method of producing an isolated cell having nephron progenitor activity.

For the purposes of this invention, by "isolated" is meant material (e.g. a cell or a nucleic acid) that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form. By "enriched" or "purified" is meant isolated material having a higher incidence, representation or frequency in a particular state (e.g an enriched or purified state) compared to a previous state prior to enrichment or purification. In the specific example of an "isolated cell", the isolated cell may be present in, or a cellular component of, a tissue or organ obtained from, or administered to, a mammal.

As generally used herein a "mammal" may be, or include, humans and non-human mammals inclusive of laboratory animals such as mice, rats, hamsters, guinea pigs, performance animals such as horses and camels, livestock such as cattle, sheep and pigs, domestic pets such as cats and dogs, although without limitation thereto.

A "progenitor cell" is a cell which is capable of differentiating along one or a plurality of developmental pathways, with or without self-renewal. Progenitor cells may be pluripotent, multipotent, oligopotent or unipotent. Typically, progenitor cells are unipotent or oligopotent and are capable of at least limited self-renewal.

As used herein "nephron progenitor cells" are progenitor cells that have "nephron progenitor activity" and can differentiate into some or all nephron segments (other than collecting duct) which include nephron epithelia such as connecting segment, distal convoluted tubule (DCT) cells, distal straight tubule (DST) cells, proximal straight tubule (PST) segments 1 and 2 PST cells, podocytes, glomerular endothelial cells, ascending Loop of Henle and/or descending Loop of Henle, although without limitation thereto. Nephron progenitor cells are also capable of self-renewal.

As used herein "induced nephron progenitors" and "induced nephron progenitor cells" (iNPs) are cells which do not normally have nephron progenitor potential or activity, or have minimal, insubstantial or insufficient nephron progenitor potential or activity, but are induced to have nephron progenitor activity as a result of expression of the SNAI2, EYA1 and SIX1 genes disclosed herein.

The terms "differentiate", "differentiating" and "differentiated", relate to progression of a cell from an earlier or initial stage of a developmental pathway to a later or more mature stage of the developmental pathway. It will be appreciated that in this context "differentiated" does not mean or imply that the cell is fully differentiated and has lost pluripotentiality or capacity to further progress along the developmental pathway or along other developmental pathways. Differentiation may be accompanied by cell division.

As will be well understood in the art, the stage or state of differentiation of a cell may be characterized by the expression and/or non-expression of one of a plurality of markers. In this context, by "markers" is meant nucleic acids or proteins that are encoded by the genome of a cell, cell population, lineage, compartment or subset, whose expression or pattern of expression changes throughout development. Nucleic acid marker expression may be detected or measured by any technique known in the art including nucleic acid sequence amplification (e.g. polymerase chain reaction) and nucleic acid hybridization (e.g. microarrays, Northern hybridization, in situ hybridization), although without limitation thereto. Protein marker expression may be detected or measured by any technique known in the art including flow cytometry, immunohistochemistry, immunoblotting, protein arrays, protein profiling (e.g 2D gel electrophoresis), although without limitation thereto.

It will be appreciated that particular aspects of the invention relate to the induction of nephron progenitor activity, or at least nephron progenitor potential, in a cell, or a tissue or organ comprising the cell, by the expression of a SNAI2 gene, an EYA1 gene and a SIX1 gene in the cell, tissue or organ that does not normally have nephron progenitor activity as described above. In this context, the cell has no ability, minimal, insubstantial or insufficient ability to differentiate into some or all nephron segments as described above. This may be any cell that can be propagated in vitro or in vivo and in which a SNAI2 gene, an EYA1 gene and a SIX1 gene are not normally expressed, or are expressed at a level which does not induce or otherwise cause said cell to have nephron progenitor activity.

In one embodiment, the cell is a differentiated cell or cell line which does not normally have nephron progenitor activity as described above. Differentiated cells have no or minimal or substantial intrinsic progenitor potential and so are a "safe" choice for producing nephron progenitors because there is less chance that these cells may become tumorigenic following expression of a SNAI2 gene, an EYA1 gene and a SIX1 gene. Non-limiting examples include fibroblasts, renal cells such as adult renal epithelial cells (e.g HK2 cells, hRPTECs), although without limitation thereto.

In another particular embodiment, the cell may be a progenitor cell in its normal state. A progenitor cell may have the advantage that it is multipotential and, as a result of expressing respective nucleotide sequences of a SNAI2 gene, an EYA1 gene and a SIX1 gene, or fragments thereof, is not only capable of differentiating into a nephron but also into one or more other renal cell types, reneal structures or tissues (e.g. ureteric components such as collecting ducts or renal vasculature) as a result of its multipotentiality. Non-limiting examples of progenitor cells include urine-derived stem cells, glomerular parietal epithelial cells, ureteric epithelial progenitor cells, intermediate mesoderm and posterior primitive streak cells, without limitation thereto. The in vitro production of renal progenitor cells (such as from human embryonic stem cells or iPSCs) that may be used according to the invention is described in detail in International Publications WO2014/197934 and WO2016/94948.

In another particular embodiment, the cell may be a primary postnatal cell type with no renal identity (e.g. fibroblast) or other mature adult cell type with no progenitor activity (e.g. primary proximal tubule epithelial cells).

In another embodiment, the cell may be a pluripotent stem cell. In this embodiment, the SNAI2, EYA1 and SIX1 genes would be inducing nephron progenitor status rather than growth factor induction.

As hereinbefore described, the cell is induced to possess nephron progenitor potential or nephron progenitor activity by expressing at least one exogenous nucleic acid that comprises a nucleotide sequence of a SNAI2 gene, an EYA1 gene and a SIX1 gene, or respective fragments thereof, at a level that induces said cell to have nephron progenitor potential or activity.

The term "nucleic acid" as used herein designates single- or double-stranded DNA and RNA. DNA includes genomic DNA and cDNA. RNA includes mRNA, RNA, RNAi, siRNA, cRNA, guide RNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylycytosine, methylinosine, methyladenosine and/or thiouridine, although without limitation thereto.

A "gene" is a structural unit or region of a genome that comprises a nucleotide sequence encoding an amino acid sequence of a protein. Typically, a gene comprises one or more exons that encode a protein and non-coding genetic elements such as one or more introns, 5' and 3' UTR and regulatory regions such as a promoter and/or enhancer.

An "exogenous" nucleic acid is at least one nucleic acid that is not normally present in the genome of the cell. While a SNAI2 gene, an EYA1 gene and a SIX1 gene are present in the genome of the cell, the exogenous nucleic acid comprising SNAI2, EYA1 and SIX1 nucleotide sequences is in a form not normally present in the genome of the cell. Suitably, the at least one exogenous nucleic acid is in the form of, or part of, a genetic construct. Preferably, the genetic construct is a transposon construct as will be described in more detail hereinafter. Specifically excluded from the exogenous nucleic acid are nucleotide sequences of one or more of a SIX2, HOXA11 and OSR1 gene, particularly murine forms of these genes.

By "protein" is meant an amino acid polymer. The amino acids may be natural or non-natural amino acids, D- or L-amino acids as are well understood in the art.

The term "protein" includes and encompasses "peptide", which is typically used to describe a protein having no more than fifty (50) amino acids and "polypeptide", which is typically used to describe a protein having more than fifty (50) amino acids.

Suitably, the at least one exogenous nucleic acid comprises a nucleotide sequences of a SNAI2 gene, an EYA1 gene and a SIX1 gene, or respective fragments thereof. A non-limiting example of a nucleotide sequence of a human SNAI2 gene comprises the nucleotide sequence set forth in SEQ ID NO:1. A non-limiting example of a nucleotide sequence of a human EYA1 gene comprises the nucleotide sequence set forth in SEQ ID NO:2. A non-limiting example of a nucleotide sequence of a human SIX1 gene comprises the nucleotide sequence set forth in SEQ ID NO:3. Corresponding murine nucleotide sequences are set forth in SEQ ID NOs.:14-16.

It will also be appreciated that nucleotide sequence variants may be used according to the invention. As used herein, a nucleotide sequence "variant" has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with the nucleotide sequence set forth in any one of SEQ ID NOs.:1-3 or 14-16. The variant may be a naturally-occurring variant, such as an allelic variant, or may be produced artificially. Non-limiting examples of artificial variants are codon-optimized nucleotide sequences and mutagenized nucleotide sequences that encode protein variants (e.g variants of EYA1, SIX1 and/or SNAI2 proteins or fragments thereof).

A protein "variant" disclosed herein may have one or more amino acids deleted or substituted by different amino acids. It is well understood in the art that some amino acids may be substituted or deleted without changing biological activity of the peptide (conservative substitutions). As used herein, a protein "variant" has at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity with an amino acid sequence encoded by the nucleotide sequence set forth in any one of SEQ ID NOs.: 1-3 or 14-16. Suitably, the protein variant has at least 60%, 65%, 70%, 75%, 80%, 85%, 90%, 91%, 92%, 93%, 94%, 95%, 96%, 97%, 98% or 99% of the biological activity of a protein having an amino acid sequence encoded by the nucleotide sequence set forth in any one of SEQ ID NOs.: 1-3 or 14-16. Preferably, the biological activity is transcription factor activity.

Terms used generally herein to describe sequence relationships between respective proteins and nucleic acids include "comparison window", "sequence identity", "percentage of sequence identity" and "substantial identity". Because respective nucleic acids/proteins may each comprise (1) only one or more portions of a complete nucleic acid/protein sequence that are shared by the nucleic acids/proteins, and (2) one or more portions which are divergent between the nucleic acids/proteins, sequence comparisons are typically performed by comparing sequences over a "comparison window" to identify and compare local regions of sequence similarity. A "comparison window" refers to a conceptual segment of typically 6, 9 or 12 contiguous residues that is compared to a reference sequence. The comparison window may comprise additions or deletions (i.e., gaps) of about 20% or less as compared to the reference sequence for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e. resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference. A detailed discussion of sequence analysis can be found in Unit 19.3 of CURRENT PROTOCOLS IN MOLECULAR BIOLOGY Eds. Ausubel et al. (John Wiley & Sons Inc NY, 1995-2015).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

As used herein a "fragment" of an isolated nucleic acid comprises a portion, sub-sequence or sub-region of an isolated nucleic acid comprising a nucleotide sequence set forth in any one of SEQ ID NOs.:1-3 or 14-16.

Suitably, the nucleic acid fragment encodes a protein fragment.

Suitably, the protein fragment has at least 60%, 65%, 70%, 75%, 80%, 85%, 90%, 91%, 92%, 93%, 94%, 95%, 96%, 97%, 98% or 99% of the biological activity of a protein having an amino acid sequence encoded by the nucleotide sequence set forth in any one of SEQ ID NOs.: 1-3 or 14-16. Preferably, the biological activity is transcription factor activity.

As hereinbefore described, it will be understood that it is the expression of the EYA1, SIX1 and SNAI2 nucleotide sequences disclosed herein (such as comprising the nucleotide sequences set forth in SEQ ID NOs.:1-3 or 14-16, or variants or fragments thereof) at a suitable level that induces or otherwise causes said cell to have nephron progenitor activity. Suitably, expression of the at least one exogenous nucleic acid is inducible, repressible or otherwise regulatable to thereby "switch" said cell from having nephron progenitor potential to having nephron progenitor activity. Thus, the presence of the at least one exogenous nucleic acid disclosed herein (such as comprising the nucleotide sequences set forth in SEQ ID NOs.:1-3 or 14-16, or variants or fragments thereof) induces or "re-programs" the cell to have nephron progenitor potential, whereby induction of expression of the at least one exogenous nucleic acid induces, causes or confers nephron progenitor activity. It will also be appreciated that an inducible, repressible or otherwise regulatable expression system allows the EYA1, SIX1 and SNAI2 genes to be "switched off", to enable the nephron progenitor cells to subsequently differentiate into nephrons.

As generally used herein "expression level" in the context of nucleic acids such as comprising the nucleotide sequences set forth in SEQ ID NOs.:1-3 or 14-16, or variants or fragments thereof, may refer to nucleic acid (e.g mRNA) expression levels or encoded protein expression levels (i.e EYA1, SIX1 and SNAI2 proteins, respectively). Expression levels may be measured and/or expressed in absolute terms (e.g. number of molecules, mass etc) or in relative terms (e.g. fold expression, expression ratios, amount per cell etc) as are well understood in the art.

Measurement of nucleic acid levels may be performed using any methods known in the art inclusive of nucleic acid sequence amplification, probe hybridisation, spectrophotometry, in situ hybridization, nucleic acid arrays, nucleic acid blotting, or combinations of these as are well known in the art. These may be performed qualitatively, semi-quantitatively or quantitatively. Non-limiting examples of nucleic acid detection are provided in CURRENT PROTOCOLS IN MOLECULAR BIOLOGY Eds. Ausubel et al. (John Wiley & Sons Inc NY, 1995-2015). Measurement of expressed EYA1, SIX1 and SNAI2 nucleic acids is also described in details in the Examples.

Measurement of protein levels may be performed using any methods known in the art inclusive of immunodetection of proteins using specific antibodies and direct detection of proteins such as by staining (e.g. silver staining, Coomassie blue staining), N-terminal sequencing, mass spectroscopy or chromatography (e.g RP-HPLC), 2-D protein profiling and protein arrays, or combinations of these. Immunodetection of proteins may be performed using antibodies specific for respective EYA1, SIX1 and SNAI2 proteins. Particular formats for immunodetection may include immunohistochemistry, immunoprecipitation, ELISA and immunoblotting, although without limitation thereto. These methods may be performed qualitatively, semi-quantitatively or quantitatively. Non-limiting examples of protein detection are provided in CURRENT PROTOCOLS IN PROTEIN SCIENCE Eds. Coligan et al. (John Wiley & Sons Inc NY, 1995-2015).

In order to facilitate delivery of the at least one exogenous nucleic acid (such as comprising the EYA1, SIX1 and SNAI2 nucleotide sequences set forth in SEQ ID NOs.:1-3 or 14-16, or variants or fragments thereof) to a cell, the at least one exogenous nucleic acid is present in a genetic construct. Suitably, the genetic construct is an "expression construct" wherein the at least one exogenous nucleic acid is operably linked or operably connected to one or more regulatory nucleotide sequences that control, facilitate or regulate expression of the EYA1, SIX1 and SNAI2 nucleotide sequences. By "operably linked" is meant that said additional nucleotide sequence(s) is/are positioned relative to the EYA1, SIX1 and SNAI2 nucleotide sequences preferably to initiate, regulate or otherwise control transcription of the EYA1, SIX1 and SNAI2 nucleotide sequences. Typically, said one or more regulatory nucleotide sequences may include, but are not limited to, promoter sequences, leader or signal sequences, ribosomal binding sites, polyadenylation sequences, transcriptional start and termination sequences, donor/acceptor splice sites, Kozak and translational start and termination sequences, and/or enhancer or activator sequences. The choice of said one or more regulatory nucleotide sequences may be at least partly dependent on the host cell type used for expression, particularly according to the origin of the host cell (e.g. mammalian or other vertebrates, plant, bacterial, yeast etc). Suitably, the one or more regulatory nucleotide sequences are operable in a human or other mammalian cell.

Broadly, the genetic construct may be in the form of, or comprise genetic components of, a plasmid, a transposon, a bacteriophage, a cosmid, a yeast or bacterial artificial chromosome as are well understood in the art. The genetic construct may be either a self-replicating extra-chromosomal construct such as a plasmid, or more preferably a construct that integrates into a host cell genome. Preferably, the genetic construct is a "non-viral" genetic construct. By this is meant that the genetic construct does not comprise, or is substantially free of, genetic elements and/or nucleotide sequences of viral origin. In the particular context of humans, the genetic construct does not comprise, or is substantially free of, genetic elements and/or nucleotide sequences of viral vectors typically used in human gene therapy such as lentivirus, adenovirus, poxvirus (e.g vaccinia virus) and/or retrovirus vectors, although without limitation thereto.

In a particular embodiment, the genetic construct is a plasmid that comprises one or more components of a transposon. The one or more components of the transposon suitably include inverted repeat (IR) sequences positioned at the 5' and 3' terminus of the transposon. Non-limiting embodiments of IR nucleotide sequences are provided in SEQ ID NOs.:4 and 5.

The genetic construct may further comprise a nucleotide sequence encoding a transposase which facilitates insertion of the transposon-containing elements of the genetic construct into a host cell genome. Typically, the transposase nucleotide sequence would be located 5' of the 5' IR or 3' of the 3' IR. Alternatively, the transposase is encoded by a nucleotide sequence of a separate plasmid. An example of a transposon-containing genetic construct is a "piggyBac" construct. In this regard, reference is made to Woodard & Wilson, 2015, Trends. Biotechnol. 33 525 which provides a review of "piggyBac" expression constructs and transposase systems for genomic insertion.

In a preferred form, the genetic construct comprises respective nucleotide sequences of a SNAI2 gene, an EYA1 gene and a SIX1 gene, or respective fragments thereof located in the same genetic construct. It will be appreciated that an advantage of the nucleotide sequences of the SNAI2 gene, the EYA1 gene and the SIX1 gene, or respective fragments thereof being located in the same genetic construct is that this facilitates co-ordinated expression of the SNAI2 gene, the EYA1 gene and the SIX1 gene, and/or their respective encoded proteins. Preferably, co-ordinated expression of the SNAI2 gene, the EYA1 gene and the SIX1 gene, and/or their respective encoded proteins may facilitate at least comparable, or preferably stoichiometric expression of the SNAI2 gene, the EYA1 gene and the SIX1 gene, and/or their respective encoded proteins in a cell. It will be appreciated that the term "stoichiometric" in this context does not mean or imply 1:1:1 expression (i.e on a molecule-for-molecule basis), but can include tolerable variation of no more than 10-fold, 9-fold, 8-fold, 7-fold, 6-fold, 5-fold, 4-fold, 3-fold or 2-fold between any two of the SNAI2 gene, the EYA1 gene and the SIX1 gene, and/or their respective encoded proteins.

Preferably, each of the respective nucleotide sequences are separated by intervening nucleotide sequences. In some embodiments, the intervening nucleotide sequences may encode one or more same or different peptides that facilitate post-translational cleavage and separation of the protein products of the expressed SNAI2, EYA1 and a SIX1 nucleotide sequences. Non-limiting examples of suitable peptides include self-cleaving peptides such as 2A peptides and/or variants of these. Non-limiting embodiments of intervening nucleotide sequences are provided in SEQ ID NOs.:9-11, 18 and 19.

It will be appreciated that other genetic constructs may be suitable, inclusive of transient expression constructs without permanent or stable integration of the SNAI2, EYA1 and SIX1 nucleic acids into the genome. Non-limiting examples include episomes, Sendai viral delivery or mRNAs. This would provide a "footprint free" outcome, such as preferred in the genetic reprogramming of iPSCs.

In one particular embodiment, the genetic construct may be pT-mSES (SEQ ID NO:12), expressing SIX1, SNAI2 and EYA1 genes from the elongation factor 1 alpha promoter (SEQ ID NO:13). As will be described in more detail hereinafter, direct, in vivo administration of a genetic construct comprising SIX1, SNAI2, and EYA1 nucleotide sequences resulted in reprogramming of host cells to become Cited1+ cells.

In another embodiment, the genetic construct may facilitate Crispr/Cas guide RNA—induced gene activation. This would be a way to induce the SNAI2, EYA1 and SIX1 genes from endogenous loci with a Cas9-VP64 or other fusion protein using guide RNAs to target the SNAI2, EYA1 and SIX1 genes.

Suitably, the genetic construct comprises one or more same or different promoters. Preferably, the genetic construct comprises a single promoter that is operably linked to the respective nucleotide sequences of a SNAI2 gene, an EYA1 gene and a SIX1 gene, or respective fragments thereof, located in the same genetic construct. The promoter may be a constitutive or inducible promoter, preferably operable in a human or other mammalian cell. Suitably, the promoter is inducible, repressible or otherwise regulatable. Non-limiting examples of such promoters are antibiotic-inducible or repressible promoters (e.g doxycycline, tetracycline inducible or repressible promoters), alcohol-inducible promoters, steroid-inducible promoters and metal-inducible promoters, although without limitation thereto. In one embodiment, the promoter is a doxycycline-inducible promoter. A particular example of a doxycycline-inducible promoter includes a tetracycline-responsive element (TRE). A non-limiting embodiment of a nucleotide sequence of a TRE is provided in SEQ ID NO:6.

The genetic construct may further comprise a nucleotide sequence that encodes a detection marker which allows detection and selection of cells that have expressed the detection marker and are therefore cells more likely to have expressed the SNAI2, EYA1 and SIX1 proteins. Preferably, the detection marker allows visual detection and selection or enrichment of cells having expressed the SNAI2, EYA1 and SIX1 proteins. An example is a fluorescent detection marker such as mCherry which allows fluorescence-based detection, such as by fluorescence microscopy, or cell sorting by flow cytometry. Other fluorescent detection markers are well known in the art and include DsRed and its variants, AsRed, mStrawberry, mVenus, mCitrine. mTurquoise and mWasabi, although without limitation thereto. A non-limiting embodiment of a nucleotide sequence encoding mCherry is provided in SEQ ID NO:7.

Another aspect of the invention provides method of inducing nephron progenitor potential in a mammalian cell, tissue or organ said method including the step of administering to said cell, tissue or organ at least one exogenous nucleic acid that comprises a nucleotide sequence of a SNAI2 gene, an EYA1 gene and a SIX1 gene, or respective fragments thereof, and that are expressible at a level that can induce said cell, tissue or organ to have nephron progenitor activity.

A related aspect provides a method of inducing nephron progenitor activity in a mammalian cell, tissue or organ, said method including the step of administering to said cell, tissue or organ, at least one exogenous nucleic acid that comprises a nucleotide sequence of a SNAI2 gene, an EYA1 gene and a SIX1 gene, or respective fragments thereof, and that are expressed at a level to induce said cell tissue or organ to have nephron progenitor activity.

As hereinbefore described, co-ordinated expression of an exogenous SNAI2 gene, EYA1 gene and SIX1 gene, or respective fragments thereof, can induce a cell to have nephron progenitor activity, wherein the cell normally has no substantial nephron progenitor potential or activity.

In addition to expression of the exogenous SNAI2 gene, EYA1 gene and SIX1 gene, or respective fragments thereof, the inventors have discovered that the induction of nephron progenitor potential or activity is facilitated by exposing said cell to appropriate culture conditions in vitro. Suitably, the appropriate culture conditions include media that facilitates induction of nephron progenitor potential or activity. In an embodiment, the media comprise a bone morphogenic protein (BMP), a fibroblast growth factor (FGF), a selective inhibitor of Rho-associated, coiled-coil containing protein kinase (ROCK), heparin, a Wnt agonist and leukaemia inhibitory factor (LIF).

The BMP is preferably BMP7. A typical BMP concentration range is about 10-200 ng/mL, about 20-100 ng/mL or about 50 ng/mL.

The FGF is preferably FGF2 or FGF9, or more preferably FGF2. FGF is typically at a concentration in the range of about 50-500 µg/mL or about 100-300 µg/mL, or at about 250 µg/mL.

The Wnt agonist is preferably a GSK3 inhibitor such as CHIR99021. Other examples of Wnt agonists are described in International Publication WO2014/197934. A typical Wnt agonist is at a concentration in the range of about 0.1-1 µg/mL or about 0.25-2.5 µg/mL, or at about 1 µg/mL.

The inhibitor of ROCK is preferably Y27632. A typical inhibitor of ROCK is at a concentration in the range of about 1-50 µM or about 5-25 µM, or at about 10 µM.

Heparin is typically at a concentration in the range of about 0.1-1 µg/mL or about 0.25-2.5 µg/mL, or at about 1 µg/mL.

LIF is typically at a concentration in the range or about 1-50 ng/mL, about 5-20 ng/mL or at about 10 µg/mL.

In embodiments of the method relating to human cells, the media may comprise additional molecules such as TGFβ/Smad inhibitors. Preferably, the media includes inhibitors of Smad 2/3 and/or Smad 1/5/8 pathways. In particular embodiments these include an inhibitor of the transcriptional activity of the BMP type I receptors ALK2 and ALK3 such as LDN193189, and/or a TGF-β type I receptor ALK4/ALK5/ALK7 kinase inhibitor such as A83-01. ALK2 and ALK3 inhibitors such as LDN193189 may be present at a concentration in the range of about 1-1000 nM, about 2-500 nM or about 5-200 nM, or at about 10-100 nM. A TGF-β type I receptor ALK4/ALK5/ALK7 kinase inhibitor such as A83-01 may be present at a concentration in the range of about 0.01-2 nM, about 0.02-1 nM, or at about 0.05-0.5 nM.

In a particular embodiment, the medium is an NPSR medium such as described in Li et al., 2016.

It will also be appreciated that induction of nephrons may be performed in vivo. As shown in the Examples, direct, in vivo administration of a genetic construct comprising SIX1, SNAI2, and EYA1 nucleotide sequences resulted in reprogramming of host cells to become Cited1+ cells.

A further aspect of the invention provides a method of producing a nephron, said method including the step of differentiating said nephron from one or more mammalian cells having nephron progenitor activity, said one or more cells each comprising at least one exogenous nucleic acid that comprises a nucleotide sequence of a SNAI2 gene, an EYA1 gene and a SIX1 gene, or respective fragments thereof, and are expressed at a level that induces said cell to have nephron progenitor activity.

It will be understood that nephron progenitors that comprise a nucleotide sequence of a SNAI2 gene, an EYA1 gene and a SIX1 gene, or respective fragments thereof expressed at a level that induces nephron progenitor activity, may be differentiated into nephrons in vitro or in vivo.

In some embodiments, the nephron progenitors may be multipotent cells or pluripotent cells as previously described, having the capacity to differentiate into other renal cell types, tissues or structures in addition to nephrons. Multipotential cells or pluripotential nephron progenitor cells may be differentiated into renal cell types, tissues or structures in addition to nephrons, such as glomerulus, juxtaglomerular apparatus, interstitial tissue, collecting ducts, Bowman's capsule, proximal and/or distal convoluted tubules, vasculature such as arterioles, arteries, veins and/or capillaries, although without limitation thereto.

Thus, the nephron progenitor cells disclosed herein may be used to produce (e.g. by differentiation) some or all nephron segments (other than collecting duct), which include nephron epithelia such as connecting segment, distal convoluted tubule (DCT) cells, distal straight tubule (DST) cells, proximal straight tubule (PST) segments 1 and 2, PST cells, podocytes, glomerular endothelial cells, ascending Loop of Henle and/or descending Loop of Henle, although without limitation thereto, alone or in combination with one or more other renal cell types, tissues or structures in addition to nephrons, such as glomerulus, juxtaglomerular apparatus, interstitial tissue, collecting ducts, Bowman's capsule, proximal and/or distal convoluted tubules, vasculature such as arterioles, arteries, veins and/or capillaries, although without limitation thereto.

Accordingly, the nephron progenitor cells disclosed herein may be suitable for therapeutic intervention in kidney disease.

An aspect of the invention provides method of producing a renal structure, said method including the step of providing a plurality of mammalian cells comprising at least one exogenous nucleic acid that comprises a nucleotide sequence of a SNAI2 gene, an EYA1 gene and a SIX1 gene, or respective fragments thereof, that are expressed at a level to induce said cells to have nephron progenitor activity, and/or one or more renal cells or tissues obtained from said cells, to thereby produce the renal structure.

The one or more renal cells or tissues obtained from said cell may include nephrons and, optionally, one or more other renal cells or tissues in addition to the nephrons.

The capacity of these cells to 'self-organise' may be exploited to facilitate kidney repair, such as by way of kidney tissue or organ bioengineering.

In one embodiment, the renal structure may be a renal organoid.

Suitably, the renal organoid is a three-dimensional renal structure.

A renal "organoid" is a complex multicellular kidney structure that comprises fully segmented nephrons surrounded by endothelia and renal interstitium and is transcriptionally similar to a human fetal kidney. The renal organoid may also include vascularization through development of vascular endothelium.

In vitro culture conditions that favour the production of renal organoids typically include culture of the nephron progenitors disclosed herein in media that include an FGF such as FGF2 or FGF9 and a Wnt agonist such as CHIR99021. In this regard, reference is made to WO2016/94948, Takasato et al., 2016 and Takasato & Little, 2016, which provide particular examples of methods whereby multicellular renal structures such as organoids may be produced from nephron progenitors or mixed populations of progenitor cells comprising nephron progenitors.

Another embodiment provides use of a plurality of nephron progenitors and/or renal cells obtained therefrom (inclusive of renal organoids), to produce an engineered or artificial kidney. For example, nephron progenitors may be incorporated within a scaffold, such as a decellularised human kidney or extracellular matrix (ECM) component thereof, polyester fleece or biodegradable polymer scaffold, to thereby produce a regenerated renal tubule structure. In some embodiments the ECM from a kidney scaffold may be used as a matrix (e.g generated from the ECM alone or in association with a hydrogel) in which to seed or bioprint the nephron progenitor cells, optionally together with other renal cell types, to thereby recellularize the kidney scaffold or matrix. By way of example, the nephron progenitor cells may be provided in combination with one or more other progenitor cells such as ureteric epithelial progenitor cells, or at least partly in vitro differentiated cells that give rise to ureteric renal structures such as collecting duct.

Non-limiting examples of decellularised kidney scaffolds potentially suitable according to this aspect of the invention are described in Song et al., 2013, Nature Medicine 19 646 and Oxburgh et al., 2017, JASN 28 1370

In another embodiment, human nephron progenitors disclosed herein may be used to make a chimeric kidney in a non-human host animal, such as pig. By way of example, human nephron progenitors may be adoptively transferred to a pig in which the endogenous nephron progenitors have been removed to thereby grow a chimeric organ with human nephrons.

As used herein "bioprinted" renal structures may include renal organoids or organ-like structures produced using the nephron progenitor cells described herein and/or renal cells or tissues differentiated or otherwise obtained from the nephron progenitor cells. By way of example, the nephron progenitor cells may provided in combination with one or more other progenitor cells such as ureteric epithelial progenitor cells, or at least partly in vitro differentiated cells that give rise to ureteric renal structures such as collecting duct.

Suitably, the bioprinted renal structure is a three-dimensional renal structure.

It will also be appreciated that the three-dimensional structure may be constructed or formed from a plurality of bioprinted "layers" or "arrays", as will be described in more detail hereinafter.

The bioprinted renal structure component may be, or comprise, any structural and/or functional component of a kidney, such as a glomerulus, juxtaglomerular apparatus, interstitial tissue, collecting ducts, Bowman's capsule, proximal and/or distal convoluted tubules, vasculature such as arterioles, arteries, veins and/or capillaries, although without limitation thereto.

As used herein, "bioprinted" and "bioprinting" includes and encompasses utilizing three-dimensional, precise deposition of cells (e.g., cell solutions, cell-containing gels, cell suspensions, cell concentrations, multicellular aggregates, organoids, multicellular bodies, etc.) via methodology that is compatible with an automated or semi-automated, computer-aided, three-dimensional prototyping device (e.g., a bioprinter). In this regard, reference is made to United States Patent Applications US20120116568, US20130164339 and US20140012407 which provide non-limiting examples of potentially suitable bioprinting techniques.

By way of example, in some embodiments, at least one component of an engineered, implantable renal organoid tissue and/or organ may bioprinted. In further embodiments, the engineered, implantable tissues and/or organs are entirely bioprinted. In still further embodiments, bioprinted constructs are made with a method that utilizes a rapid prototyping technology based on three-dimensional, automated, computer-aided deposition of renal cells as disclosed herein, including cell solutions, cell suspensions, cell-comprising gels or pastes, cell concentrations, multicellular bodies (e.g., cylinders, spheroids, ribbons, etc.), and confinement material onto a biocompatible surface (e.g., composed of hydrogel and/or a porous membrane) by a three-dimensional delivery device (e.g., a bioprinter). As used herein, in some embodiments, the term "engineered," refer to renal tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules. In still further embodiments, three-dimensional tissue structures form through the post-printing fusion of cells or multicellular bodies similar to self-assembly phenomena in early morphogenesis.

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage. In some embodiments, the method of bioprinting is continuous and/or substantially continuous. A non-limiting example of a continuous bioprinting method is to dispense bio-ink from a bioprinter via a dispense tip (e.g., a syringe, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries. In further embodiments, a repeating pattern of bioprinted function units comprises a layer or array and a plurality of layers or arrays are bioprinted adjacently (e.g., stacked) to form an engineered tissue or organ. In various embodiments, 2, 3, 4, 5, 6, 7, 8, 9, 10, 11, 12, 13, 14, 15, or more layers or arrays are bioprinted adjacently (e.g., stacked) to form an engineered renal tissue or organ.

In some embodiments, a bioprinted functional unit repeats in a tessellated pattern. A "tessellated pattern" is a plane of figures that fills the plane with no overlaps and no gaps.

Advantages of continuous and/or tessellated bioprinting include, by way of non-limiting example, increased productivity of bioprinted tissue. Another non-limiting, exemplary advantage is eliminating the need to align the bioprinter with previously deposited elements of bio-ink. Continuous bioprinting also facilitates printing larger tissues from a large reservoir of bio-ink, optionally using a syringe mechanism.

In various embodiments, methods for continuous bioprinting involve optimizing and/or balancing parameters such as print height, pump speed, robot speed, or combinations thereof independently or relative to each other. In one example, the bioprinter head speed for deposition was 3 mm/s, with a dispense height of 0.5 mm for the first layer and dispense height was increased 0.4 mm for each subsequent layer. In some embodiments, the dispense height is approximately equal to the diameter of the bioprinter dispense tip. Without limitation a suitable and/or optimal dispense distance does not result in material flattening or adhering to the dispensing needle. In various embodiments, the bioprinter dispense tip has an inner diameter of about, 20, 50, 100, 150, 200, 250, 300, 350, 400, 450, 500, 550, 600, 650, 700, 750, 800, 850, 900, 950, 1000 µm, or more, including increments therein. In various embodiments, the bio-ink reservoir of the bioprinter has a volume of about 0.5, 1, 2, 3, 4, 5, 6, 7, 8, 9, 10, 15, 20, 25, 30, 35, 40, 45, 50, 55, 60, 65, 70, 75, 80, 85, 90, 95, 100 $cm^3$, or more, including increments therein. In some embodiments, the pump speed is suitable and/or optimal when the residual pressure build-up in the system is low. In some embodiments, favourable pump speeds depend on the ratio between the cross-sectional areas of the reservoir and dispense needle with larger ratios requiring lower pump speeds. In some embodiments, a suitable and/or optimal print speed enables the deposition of a uniform line without affecting the mechanical integrity of the material.

By way of example only, Organovo partnered with Invetech have developed an organ printing machine which uses a hydrogel scaffold to place human cells in a desired orientation to recreate human organs. Kidney cells or tissues differentiated or otherwise obtained from the nephron progenitors described herein may be used with machines, such as the Organovo machine referred to above, to develop a "bioprinted" human kidney organoid or kidney.

Another embodiment provides an array of nephron progenitors and optionally one or more other renal progenitors or renal cell types, having a planar geometry.

The array may comprise a plurality of stacked arrays, preferably 2, 3, 4, 5, 6, 7, 8, 9, 10, 11, 12, 13, 14 or 15 or more stacked arrays.

The arrays may stacked in a tessellated pattern.

Another aspect of the invention provides method of treating or preventing a renal disease, disorder or condition in a mammal, said method including the step of administering to the mammal at least one exogenous nucleic acid that comprises a nucleotide sequence of a SNAI2 gene, an EYA1 gene and a SIX1 gene, or respective fragments thereof, that are expressed at a level to induce a cell to have nephron progenitor activity, or a cell comprising said at least one exogenous nucleic acid and/or one or more renal cells or tissues obtained from said cell, to thereby treat or prevent the renal disease, disorder or condition in the mammal.

The one or more renal cells or tissues obtained from said cell may include nephrons and, optionally, one or more other renal cells or tissues in addition to the nephrons.

It will be appreciated that one embodiment of the method of this aspect may, include adoptively transferring or transplanting nephron progenitor cells, into a human to thereby produce the kidney, or kidney cells or tissues, or progenitors of these. The nephron progenitor cells may be adoptively transferred in combination with one or more other progenitor cells such as ureteric epithelial progenitor cells that give rise to ureteric renal structures such as collecting duct.

According to this embodiment, differentiation of the nephron progenitor cells into the kidney or kidney cells or tissues occurs in vivo.

It will also be appreciated that the method may include administration of a genetic construct directly to the mammal in vivo. As shown in the Examples, direct, in vivo administration of a genetic construct comprising SIX1, SNAI2, and EYA1 nucleotide sequences resulted in reprogramming of host cells to become Cited1+ cells.

Another embodiment of the method of this aspect may include at least partly differentiating isolated or purified nephron cells in vitro into kidney, or kidney cells or tissues, or progenitors of these. Suitably, the at least partly in vitro differentiated cells kidney, or kidney cells or tissues, or progenitors thereof, are adoptively transferred or transplanted into a human. The nephron progenitor cells may be adoptively transferred in combination with one or more other progenitor cells such as ureteric epithelial progenitor cells, or at least partly in vitro differentiated cells that give rise to ureteric renal structures such as collecting duct.

In some embodiments, renal structures such as organoids, reconstituted kidney scaffolds and/or bioprinted renal structures may be adoptively transferred to the human.

Particular embodiments of this aspect may relate to repairing a damaged or diseased kidney. By way of example, the method may include one or more of (i) isolating one or more differentiated cell types and/or or intermediate progenitor cell types from the organoids; (ii) delivering the one or more differentiated cell types and/or or intermediate progenitor cell types into a damaged or diseased kidney to thereby facilitate repair and/or regeneration of the diseased or damaged kidney. Delivery might by directly into the damaged or diseased kidney via parenchymal injection or via a vascular route.

Another embodiment provides the generation of kidney cells or tissues differentiated from the nephron progenitors in devices for assisting or facilitating renal dialysis. For example, bioartificial kidneys may be made by seeding kidney cells, or their progenitors into reactors to produce a 'renal assistance device' for use in parallel with dialysis or in bioartificial kidney devices that are implanted into the patient.

It will also be appreciated that the directed differentiation of nephron progenitors, renal organoids and/or bioprinted renal structures described herein may be suitable for cellular therapy.

For example, the nephron progenitors described herein may be useful for generating renal cells or tissues after gene correction in certain genetically-inherited renal conditions. For example, correction of single gene renal disorders, including Alport syndrome (COL4A3 mutation) and the polycystic kidney diseases (PKD1, PKD2 and others), may be assisted or facilitated by regeneration of renal tissue from the nephron progenitors and/or ureteric epithelial progenitors described herein after gene correction.

In a particular embodiment, autologous cells derived, obtained or originating from a patient with genetic renal disease may be used to produce nephron progenitors for repair of genetic mutation(s) in vitro. Such cells could be used according to the method of the invention and then administered to the patient for autologous cellular therapy.

It will also be appreciated that the directed differentiation of nephron progenitors described herein may provide potential sources of purified, differentiated renal cells, bioprinted renal structures, renal organoids, arrays or renal tissue subtypes for nephrotoxicity screening.

The development of interventions aimed at preventing disease, including drug and cellular-based therapies, is made difficult by the lack of availability of primary human kidney cells for in vitro drug testing.

Accordingly, one particular embodiment provides a method of determining the nephrotoxicity of one or a plurality of compounds, said method including the step of contacting the one or plurality of compounds with the nephron progenitor cells and/or ureteric epithelial progenitor cells described herein, either as an organoid or after isolation and purification, or kidney cells or tissues differentiated or otherwise obtained therefrom, to thereby determine whether or not the one or plurality of compounds is nephrotoxic.

Preferably, the method is performed using organoids or from isolated or purified nephron progenitor cells, or kidney cells or tissues derived from the nephron progenitor cells.

Many useful drugs have nephrotoxic side effects, such as by direct tubular effects (e.g aminoglycoside antibiotics, cisplatin, radiocontrast media, NSAIDs, ACE inhibitors), interstitial nephritis (e.g β lactam antibiotics, lithium, CsA, anti-epileptic drugs such as phenytoin) or glomerulonephritis, for example. It may therefore be advantageous to test new or existing drugs using defined, specific kidney cells and tissue types differentiated or otherwise obtained from the isolated or purified nephron progenitor cells described herein. The hereinbefore described "bioprinted" kidney or bioprinted kidney organoid may also be applicable to nephrotoxicity screening.

Nephrotoxicity may be assessed or measured by any appropriate test for renal cell function in vitro, including decreased creatinine clearance or biomarker expression such as by the Human Nephrotoxicity $RT^2$ Profiler™ PCR Array from Qiagen or the High Content Analysis (HCA) Multiplexed Nephrotoxicity Assay from Eurofins, although without limitation thereto.

So that the invention may be fully understood and put into practical effect, reference is made to the following non-limiting examples.

EXAMPLES

Introduction

We have previously demonstrated a proof-of-concept for direct reprogramming to induced nephron progenitors (iNPs) using a lentivirus-mediated screen that identified a pool of six transcription factors (SIX1, SIX2, OSR1, HOXA11, EYA1 and SNAI2) (Hendry et al., 2013). The resulting iNPs demonstrated appropriate NP gene and protein expression together with a selective capacity to integrate into the endogenous NP population within the nephrogenic zone of ex vivo embryonic mouse kidney cultures. Although an exciting advance, this original system of reprogramming to iNPs was limited by a lack of transcription factor inducibility and no selective marker. This hampered the evaluation of subsequent nephron differentiation capacity and ability to selectively enrich for reprogrammed clones. The specific generation of a NP population using an inducible and reversible direct reprogramming approach would represent a major advance in this field.

An additional complicating factor to this field has been the lack of defined media conditions able to maintain NP long term in vitro. Early studies of mouse NPs suggested the requirement of FGF9/20 (Barak et al., 2012), suppression of SMAD-based BMP signaling (Brown et al., 2013), low-level canonical Wnt signaling (Karner et al., 2011) and a potential role for LIF (Barasch et al., 1999, Plisov et al., 2001). Building on this knowledge, three recent studies have reported overlapping but unique NP-supportive media formulations capable of supporting the in vitro expansion of mouse (endogenous) and human (endogenous, ESC or iPSC-derived) NP populations (Li et al., 2016, Brown et al., 2015, Tanigawa et al., 2016).

Here we report the development of a novel piggyBac transposon system for direct transcriptional reprogramming to iNPs. Incorporation of an inducible promoter, selectable marker for cell enrichment and 2A peptide cleavage signals enabled inducible, simultaneous expression of all six previously identified genes within our iNP reprogramming pool. Clonal selection and analysis of transposon integration events revealed a requirement for only three of these genes, SIX1, EYA1 and SNAI2, to generate an iNP phenotype able to contribute to nephron formation in vivo and ex vivo, in mouse kidney and human iPSC-derived kidney organoids. The combination of inducible expression of these genes with culture in a previously reported NP-supportive medium, NPSR (Li et al., 2016), proved to be the most effective method to generate human iNPs and also enabled reprogramming of primary proximal tubule cells. Such cells were able to contribute to nephron formation in vivo and ex vivo, in neonatal mouse kidney and human iPSC-derived kidney organoids, and integrate into nephrons of the postnatal murine kidney following acute ischemic injury. This approach represents a significant step towards the generation of NPs to facilitate the production of nephrons for kidney bioengineering applications in the future.

Experimental Procedures

Reprogramming Constructs, Transfection and Clone Generation

The full length reprogramming transposon (pT-iNP) was constructed using commercial gene synthesis and cloned into the pUC57-Amp plasmid (GENEWIZ, South Plainfield, N.J.). The smaller reprogramming transposons (pT-SOH and pT-SES) and control transposon (pT-mCherry) were generated using pT-iNP as a starting template and following standard cloning procedures, including restriction enzyme digestion (New England Biolabs, Ipswich, Mass.) and ligation with T4 DNase Ligase (Invitrogen, ThermoFisher Scientific, Waltham, Mass.) according to manufacturer's directions. The plasmid pT-mSES expressing the mouse transcription factors for in situ experiments is available as vector ID VB170415-1003gad (Cyagen/Vectorbuilder, Santa Clara, Calif.). Plasmids pT-TetON (Saridey et al., 2009) and pEF-1α-m7pB (Woodard et al., 2017) have been described previously. Plasmid DNA for transfection was prepared using the ZymoPURE Plasmid Midiprep Kit (Zymo Research, Irvine, Calif.). For HK2 cells, transfection was performed with FuGENE HD or FuGENE 6 (Promega, Madison, Wis.) in 6-well plates according to the manufacturer's instructions, with 1 µg of DNA used for each transfection, containing equimolar amounts of reprogramming or control transposons, 200 ng pT-TetON and 100 ng pEF-1α-HA-m7pB. For hRPTECs (CC-2553; Lonza, Basel, Switzerland), transfection was performed via electroporation using the Neon Transfection system (ThermoFisher Scientific, Waltham, Mass.) 48 hours after passaging. Prior to electroporation, cells were harvested with TrypLE (ThermoFisher) and resuspended in Buffer R at a final density of $1 \times 10^7$ cells/mL. One hundred microliters of the cell suspension was added to a tube containing the reprogramming plasmids (2 µg pEF-1α-HA-m7pB, 2 µg pT-TetON and 5 µg pT-SES) and electroporated using optimised conditions (1150 V, 30 ms, 2 pulses). For reprogramming experiments using stably-transfected HK2 cells, transfected cells were cultured for 2 weeks prior to brief exposure to doxycycline and FACS isolation of mCherry-expressing stably transfected cells. Stably transfected clones were generated through serial dilution and expansion of the FACS isolated population.

Cell Culture and Reprogramming

HK2 cells (ATCC; CRL-2190) were maintained as described previously (Jones et al., 2003) in HK2 growth media (HGM; DMEM/F12 [Invitrogen] supplemented with 5 µL/mL Insulin-Transferrin-Selenite [ITS] solution [5 µg/mL insulin, 5 µg/mL transferrin and 5 ng/mL sodium selenite; Sigma Aldrich, St. Louis, Missouri], 100 U/mL penicillin and 100 g/mL streptomycin solution [PenStrep; Invitrogen], 0.1 µM hydrocortisone [Sigma Aldrich], 2 nmol/L L-glutamine [GlutaMax; Invitrogen] and 10% fetal calf serum [FCS]). For reprogramming, stably transfected cells were seeded at a density of 4000 cell/cm² and allowed to recover for 48 hours. Following recovery, media was replaced with HGM containing 2 mM valproic acid (VPA; Sigma Aldrich) and 2 µg/mL doxycycline (Sigma Aldrich) for a total of 48 hours, refreshing after 24 hours. Cells were then exposed to media containing 2 µg/mL doxycycline without VPA for the duration of reprogramming (typically 8 days), refreshing media to replenish the doxycycline every 24 hours. For NP media experiments, HGM media was removed and replaced with either CDBLY, NPEM or NPSR (Tanigawa et al., 2016, Li et al., 2016, Brown et al., 2015), with 2 ug/mL doxycycline for days 5 through 8 of the reprogramming protocol. Doxycycline exposure was discontinued to test the differentiation capacity of the iNPs in subsequent functional assays.

Transposon Copy Number Assay

Genomic DNA was purified by DNeasy Blood and Tissue Kit (Qiagen) and diluted to 1 ng/µl in buffer AE (Qiagen, Hilden, Germany). Quantitative PCR (qPCR) was performed with iQ SYBR Green (Bio-Rad, Hercules, Calif.). For the reprogramming transposons, each well contained 10 ng of genomic DNA. The standard curve wells were dilutions of each reprogramming plasmid in 10 ng of genomic DNA from naïve HK2s. The primer sets for detection of pT-TetON were rtTA-F (GAGCAAAGTCATAAACGGCG; SEQ ID NO:31) and rtTA-R (CTTTT-GAGCGAGTTTCCTTGTC; SEQ ID NO:32), for pT-SOH were HOXA11-F (TCAGAACAGGAGAATGAAGGAAA; SEQ ID NO:33) and Tm2A-R (ACATCGCCACAGGT-CAAC; SEQ ID NO:34), and for pT-SES were E2A-F (CTTTGTTGAAACTCGCTGGC; SEQ ID NO:35) and SIX1-R (GGCAGCATCGACATCAATTTAA; SEQ ID NO:36). The program was 95° C. for 3 min, 40 cycles of 95° C. for 10 sec and 58° C. for 30 sec followed by melt curve analysis. The primers and program for quantification of the number of haploid genomes by qPCR for RnaseP has been previously described elsewhere (Woodard et al., 2012). Technical triplicates were performed for each data point. Data analysis was performed in CFX Manager (Bio-Rad), Excel (Microsoft, Redmond, Wash.), and GraphPad Prism software.

Western Blotting

HK2 cells were transfected with the pT-iNP construct using FuGENE 6 (Promega) and harvested for lysis in radioimmunoprecipitation (RIPA) buffer 72 hours post-transfection. Western blotting was performed according to antibody manufacturer's directions (Abcam) using the Bio-Rad Mini System (Bio-Rad) and 20% pre-cast polyacrylamide gels (Bio-Rad). Proteins were transferred to nitrocellulose membranes (Bio-Rad) using the Semi-dry transfer buffer according to the Abcam protocol and visualized with Ponceau Red (Sigma Aldrich). Blocking and antibody incubations were performed for 12-16 hours at 4° C., with the blocking solution (5% skim milk) and antibodies diluted in Tris Buffer Saline Tween20 (TBST). Antibody details are listed in Table 3. Blots were visualized using x-ray film and chemiluminescence detection (ThermoFisher).

Excision PCR

Transfections were performed in triplicate and cells harvested the following day by trypsinization. A modified miniprep procedure was performed on the cell pellet with 5-minute incubations in buffers P2 and N3 to purify the plasmid DNA from the cells. The positive control plasmid pT-iNP-Exc was made by digesting pT-iNP with PspXI (New England Biolabs) and self-ligating the purified vector backbone fragment. The first-round excision PCR reaction contained 1 µl of each plasmid miniprep as template in a 50 µl reaction containing Taq-Pro Red Complete (Denville Scientific, Holliston, Mass.) and the primers iNP-Exc-3F (GGCGATTAAGTTGGGTAACG; SEQ ID NO:37) and iNP-Exc-3R (ACTGGAAAGCGGGCAGTGAG; SEQ ID NO:38). The second-round excision PCR used 1 µl of the first-round PCR as the DNA template in a 50 µl reaction containing Taq-Pro Red Complete (Denville Scientific) and the primers iNP-Exc-2F (CGACGGCCAGTGAAT-TCGAG; SEQ ID NO:39) and iNP-Exc-2R (CTTCCGGCTCGTATGTTGTG; SEQ ID NO:40). Both programs were 95° C. 2 min, 40 cycles of 95° C. 30 sec, 56° C. 30 sec, and 72° C. 30 sec, followed by 72° C. for 10 min and a hold at 10° C. Samples were run on a 4% agarose (Denville Scientific) TAE gel containing ethidium bromide (Bio-Rad) and imaged on the ChemiDoc XRS+ (Bio-Rad).

Immunofluorescence

For immunofluorescence, cultures and tissues were fixed in ice cold 2% paraformaldehyde (PFA; Sigma Aldrich) for 10 minutes (cell monolayers), 20 minutes (mouse and human organoids) or 1 hour (postnatal kidneys), followed by 15 minutes washing in three changes of phosphate-buffered saline (PBS). Adult kidneys were fixed in 4% PFA at 4° C. for 5 hours. Postnatal kidneys were cryoprotected in 30% sucrose solution (Sigma Aldrich) overnight prior to embedding and cryosectioning. For immunofluorescence of sections and cell monolayers cultured on coverslips, blocking and antibody staining incubations were performed for 1 hour at room temperature. Organoids were cut off transwell filters and transferred to 48 well plates for immunofluorescence, with all incubations performed at 4° C. overnight on a rocking platform. Blocking solutions included either 10% donkey serum or sheep serum with 0.1% (cells and sections) or 0.3% (organoids) Triton-X-100 (TX-100; Sigma Aldrich) in PBS, with the addition of 50% Mouse on Mouse (M.O.M.; Vector Laboratories, Burlingame, Calif.) block where mouse primary antibodies were to be used on mouse tissue. Antibodies were diluted in 0.1-0.3% TX-100/PBS and details are supplied in Table 3. Primary antibodies were detected with Alexa Fluor-conjugated fluorescent secondary antibodies (Invitrogen), diluted 1:500. Nuclei were detected with DAPI diluted 1:1000 in PBS included with the secondary antibody solution. Cells/sections and organoids were washed in three changes of PBS for either 30 minutes (10 minutes per wash) or 3 hours (1 hour per wash) respectively following primary and secondary antibody incubations. For periodic acid-Shiff (PAS) staining, sections were stained using the Ventana PAS staining kit (Roche, Basel, Switzerland) according to manufacturer's instructions in a Ventana bench mark special stains automated slide stainer (Roche). Coverslips and sections were mounted using ProLong Gold (Invitrogen) for immunofluorescence or Biomount X (Sterihealth, Victoria, Australia) for histochemistry prior to imaging. For in situ reprogramming, ProLong Gold+DAPI mounting media was used instead (Life Technologies). Imaging was performed on the Olympus BX-51 upright microscope and Zeiss Meta 510 or Zeiss LSM 780 confocal microscopes and the Leica DM1000 light microscope.

Quantitative RT-PCR

RNA was extracted from cell cultures using RNeasy Mini/Micro Kits (Qiagen) or Bioline Isolate II Mini/Micro Kits (Bioline, New South Wales, Australia) as per manufacturer's instructions. Synthesis of cDNA and qRT-PCR was performed and analysed as described previously and using the same qRT-PCR primers (Hendry et al., 2013). Each qRT-PCR reaction was performed in triplicate, with means calculated based on at least two biological replicates and expressed as +/− SEM. Data was graphed and analysed in GraphPad Prism 7.

RNA-Seq

RNA was isolated using the Bioline Isolate II Mini kit from Clone 8 iNPs (cultured in NPSR or HGM) and Clone 8 uninduced control cells (exposed to identical reprogramming conditions in HGM, but without doxycycline), with 3 replicates per condition. RNA was submitted to the MCRI Research Genomics Service (Translational Genomics Unit, MCRI, Melbourne, Australia) for library preparation and sequencing (75 bp paired end reads) using the Illumina TruSeq Stranded Total RNA library Prep Kit and Illumina NextSeq 500 Sequencing System (Illumina, San Diego, Calif.). The datasets were deposited in NCBI's Gene Expression Omnibus (Edgar et al., 2002) and are accessible through GEO Series accession number GSE107410 (https://www.ncbi.nlm.nih.gov/geo/query/acc.cgi?acc=GSE107410). Reads were trimmed for quality using Trimmomatic v0.35 (Bolger et al., 2014) to remove bases from the ends of reads with quality lower than 25, as well as exclude reads less than 30 bp and Illumina adaptors. The trimmed reads were then mapped to the hg38 reference genome using the STAR aligner v2.5.2a (Dobin et al., 2013) in two pass paired end mode and gene level counts calculated using FeatureCounts v1.5.0-p3 (Liao et al., 2014) and the GENCODE_V20 annotation. The R programming language and Bioconductor (Gentleman et al., 2004) packages were used for subsequent analyses. Genes showing low expression (less than one count per million in at least three samples) were excluded from the analyses and counts were normalized using TMM (Robinson et al., 2010). Differential expressions analysis was performed using voom transformed counts (Law et al., 2014) and limma (Ritchie et al., 2015). Differential expression was tested between four groups: (1) Clone 8 uninduced and Clone 8 iNPs in HGM, (2) Clone 8 uninduced and Clone 8 iNPs in NPSR, (3) Clone 8 uninduced and both Clone 8 iNPs in HGM and NPSR combined, (4) Clone 8 iNPs in HGM and Clone 8 iNPs in NPSR. Testing relative to a threshold (TREAT) analysis from limma was also performed, assessing for a $\log_2$-fold change greater than 1 (2-fold) across all four groups.

Neonatal Injection Assay

Neonatal injections of control (HK2-mCherry) and test (reprogrammed) cells into the cortical region of postnatal mice were performed as described previously (Li et al., 2015) in accordance with Institutional animal ethics guidelines (IMB/132/13/NHMRC and A783). Injections were performed in triplicate for control and test cells (approximately $4.5 \times 10^4$ cells per injection) and kidneys were harvested at 3 and 7 days post-injection. For the test cell injection depicted in FIG. 3, reprogramming of the injected cell population was confirmed via qRT-PCR.

Mouse Kidney Organoid Assay

Assays were performed as previously described (Lusis et al., 2010, Davies et al., 2012), with some modifications to cell percentages and culture setup. Organoids consisted of a total of $5 \times 10^5$ single cells containing 5% exogenous (control or test) cells. Following centrifugation, aggregates were transferred to 6-well Transwell filter plates (Corning, Corning, N.Y.) for culture as organoids at an air-media interface. Mouse kidney organoids were cultured for 7 days in DMEM/F12 (cat. no 11320-082; Invitrogen) supplemented with 1% PenStrep (Invitrogen) and 10% FCS, without doxycycline to enable differentiation of the iNPs. A minimum of three mouse organoids were generated for each cell type and media condition. Prior to harvesting, organoids were briefly exposed to doxycycline (<6 hours) to re-express mCherry in the control and test cells to assist localization via immunofluorescence.

Human iPSC-Derived Kidney Organoid Assay

The CRL1502 clone C32 hiPSC line (Briggs et al., 2013) was differentiated to renal progenitors as described previously (Takasato et al., 2016). At day 7, the iPS-derived progenitor cells were detached, resuspended and counted before combining with test (reprogrammed iNPs) or control (HK2-mCherry) cells to form suspensions of 95% day 7 C32s and 5% test or control cells. Suspensions were then aggregated and organoids cultured according to Takasato et al. (2016). At least 3 organoids were generated for each cell type and media condition. Prior to harvesting at day 10 post-aggregation, organoids were briefly exposed to doxycycline (<6 hours) to re-express mCherry in the control and test cells to assist localization via immunofluorescence.

Ischemia Reperfusion Injury (IRI) Model of Acute Kidney Injury

Unilateral IRI was performed as previously described (Marschner et al., 2016) using immunodeficient male NOD-SCID gamma (NSG) mice (Animal Resources Centre [ARC], JAX stock number 005557) in accordance with institutional animal ethics guidelines (animal ethics number A831 and A846). Mice were divided between test (Clone 8 iNP cell-injected) and control (Clone 8 uninduced cell-injected) groups, with 3 biological replicates per group. In each mouse, left kidney was subjected to 15 minutes of renal pedicle clamping followed by direct injection into the renal parenchyma of $5 \times 10^5$ test or control cells resuspended in 50 uL of PBS. The clamp was then released to facilitate reperfusion. Both injected and uninjected kidneys were harvested at 10 days post-surgery for immunofluorescence and histochemical analyses. Quantification of Clone 8 iNP and control cell integration events was performed on at least 6 sections for each of the biological replicates, with sections spaced evenly to cover the entire sectioned kidney. Means were calculated based on 3 biological replicates per condition and expressed as +/− SEM.

In Situ Reprogramming by Renal Pelvis Hydrodynamic Injection of pT-mSES

Renal pelvis hydrodynamic injection was performed as previously described (Woodard et al Sci Rep 2017, Woodard et al J. Vis. Exp. 2017) on 15 week-old Cited1-CreER$^{T2}$ BAC transgenic mice (Boyle et al Dev. Biol. 2008). Mice were assayed for presence of the GFP transgene at weaning (Transnetyx, Cordova, Tenn.). A solution of 50 ug of pT-mSES in 100 uL of buffer QR (Minis Bio, Madison, Wis.) was injected quickly into the renal pelvis of mice anesthetized with ketamine/xylazine. Mice were treated every 8-12 h with buprenorphine for pain management for 48 h and sacrificed at 72 h post-injection.

Results

Development of a piggyBac Transposon-Mediated Reprogramming System

PiggyBac transposons offer several advantages over traditional gene delivery systems, including a large cargo capacity (Li et al., 2011), multiplexed gene delivery (Kahlig et al., 2010), flexibility of target cell type (Woodard et al., 2015), suitability for in vivo applications (Saridey et al., 2009, Doherty et al., 2012) and ability to be excised from the genome (Elick et al., 1996). Six transcription factors (SIX1, SIX2, OSR1, EYA1 and SNAI2) have previously been identified that, when co-transduced in individual lentiviral constructs, were able to induce a NP-like state in the mature human kidney epithelial cell line (HK2) (Hendry et al., 2013). However, this was relatively uncontrolled expression which did not ensure that all six genes would be expressed in the same cell at even roughly comparable, let alone stoichiometric levels.

Figure 1:
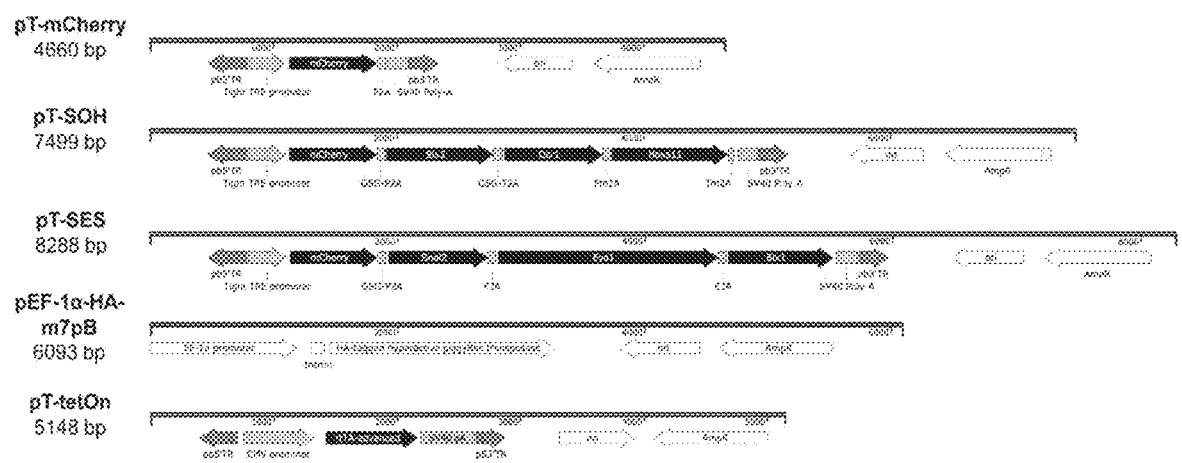
FIG. 1: piggyBac Transposon and Transposase Plasmid Maps.

To generate a reprogramming system that would provide greater control over reprogramming factor expression, a three-component system was designed that comprised two piggyBac transposons for reprogramming factor delivery (pT-SOH, containing SIX2, OSR1 and HOXA11, and pT-SES, containing SNAI2, EYA1 and SIX1), a separate piggyBac transposon conferring doxycycline inducibility (pT-TetON) (Saridey et al., 2009) and a hyperactive piggyBac transposase plasmid (p-EF-1α-HA-m7pB) for efficient mammalian genomic integration (FIG. 1 and Table 1) (Yusa et al., 2011, Doherty et al., 2012). The multicistronic piggyBac reprogramming transposons were each engineered under the control of a Tight TRE doxycycline-inducible promoter, driving the mCherry fluorescent reporter and three reprogramming factors separated by unique 2A peptides (FIG. 1 and Table 2). Precise excision of the transposon plasmids from the genome was confirmed (FIG. 2B), as was the efficient cleavage of all six intervening 2A-peptides (FIG. 2C) and the expression and correct localisation of reprogramming factor proteins for which functional commercial antibodies were available (FIG. 2D and Table 3). A transposon with the mCherry reporter alone (pT-mCherry) under the control of the Tight TRE promoter was constructed as a control for the transfection and integration process itself (FIG. 1). Expression of this reporter confirmed functionality and stringency of the TightTRE promoter (FIG. 2E).

A reprogramming transposon construct containing all six reprogramming factors (pT-iNP) was also generated (FIG. 2A). However, as it was found to be less efficient at being precisely excised from the transposon plasmid compared to pT-SOH and pT-SES (FIG. 2B), all subsequent experiments presented herein used the dual reprogramming transposons (pT-SOH and pT-SES). Efficient cleavage of all six intervening 2A-peptides was confirmed (FIG. 2C), as was the expression and correct localisation of reprogramming factor proteins for which functional commercial antibodies were available (FIG. 2D and Table 3). Finally, functionality and stringency of the TightTRE promoter was ensured using the mCherry fluorescent reporter (FIG. 2E).

In Vitro Reprogramming of Human Kidney Epithelial Cells to a NP-Like Phenotype

To confirm successful reprogramming to iNPs using the piggyBac transposon system, we utilized the same adult human kidney epithelial cell line (HK2) that was used in our original lentiviral screening approach (Hendry et al., 2013). Following co-transfection of the reprogramming and TetON transposons (pT-SOH, pT-SES and pT-TetON) along with the m7pB transposase, HK2 cells were exposed to a combination of valproic acid (VPA) and doxycycline for 48 hours to aid the reprogramming process (Hendry et al., 2013, Huangfu et al., 2008). After 48 hours, VPA was removed and reprogramming continued with doxycycline alone. Gene expression was assessed over a 10 day time course in order to find the optimal length of doxycycline exposure to induce reprogramming (FIG. 3A) and using primers that detect only endogenous gene expression in cases where the those genes were included in the transposons. A number of NP and EMT markers, including SALL1, SIX2, PAX2, OSR1, MMP2 and MMP9, were found to increase in expression over time. Despite CITED1 RNA levels decreasing dramatically after 4 days of doxycycline exposure, robust CITED1 protein expression was observed between days 6-8 of reprogramming. This data, combined with the spike in stromal marker FOXD1 by day 10, suggested 8 days of doxycycline exposure to be optimal.

By day 8 of reprogramming, the formation of raised structures co-ordinately expressing CITED1 and mCherry protein were observed in cultures transfected with the reprogramming transposons (FIGS. 3B and 3C), but were absent from control cells (FIG. 3C). Further analysis revealed expression of a range of additional marker proteins in these structures, including PAX2, SIX2 and EYA1 (FIG. 3D), with co-ordinated expression of NP proteins including EYA and SIX2 being confirmed where permitted by antibody species cross-reactivity (FIG. 12A). Furthermore, these structures lacked epithelial E-CADHERIN protein expression (FIG. 12B) which, along with the increase in MMP2 and MMP9 gene expression, was suggestive of an EMT event.

As a first-pass assessment of whether any cells within the heterogeneous reprogrammed cell population displayed differentiation capacity, we used a mouse neonatal injection model which exploits the persistence of the mouse NP population to postnatal day 2 (PND2) to test whether exogenous cells can incorporate into developing nephron structures (Li et al., 2015) (FIG. 4A). Reprogrammed cells combined with fluorescent microspheres for confirmation of injection site were directly injected into the renal parenchyma of PND1 mouse kidneys, whilst control mice were injected with control HK2-mCherry cells (HK2 cells transfected with a transposon carrying mCherry only and then subjected to the same reprogramming protocol) or fluorescent microspheres alone. At 3 days post-injection, surviving cells were seen in both test (iNP) and control (HK2-mCherry) kidneys, with a proportion of these cells being integrated into developing tubules (defined by laminin-bound basement membrane) (FIG. 4Bi). However, by 7 days post-injection no HK2-mCherry cells persisted in control kidneys, despite the presence of fluorescent microspheres confirming that the suspension was delivered successfully (FIG. 4D). In contrast, abundant reprogrammed cells were integrated into LTL+ proximal and LTL− distal nephron segments (co-stained with laminin to mark tubule basement membranes) (FIG. 4Bii). Of note was the formation of extended tubule segments by the reprogrammed cells and their binding of LTL on the apical brush border membrane as would be expected for a mature proximal tubule. No interstitial reprogrammed cells were observed.

Taken together, these data indicated the acquisition of a NP-like phenotype by the reprogrammed HK2 cells and the presence of a subset of cells with nephrogenic differentiation capacity, suggesting the effectiveness of our novel transposon-mediated reprogramming system.

Reprogrammed Cells Display In Vivo Nephron Formation Capacity

The distinct advantage of this system over others is its transferability to in vivo and ex vivo applications, enabling the demonstration of true nephron potential via differentiation of reprogrammed cells. To test whether any cells within the heterogeneous reprogrammed cell population displayed differentiation capacity, we used a previously described mouse neonatal injection model (Li et al., 2015) (FIG. 4A). In mice, the NP population persists and nephrogenesis continues up to postnatal day 2 (PND2) (Rumballe et al., 2011), providing the ideal model with which to test whether exogenous cells can incorporate into developing nephron structures. Reprogrammed cells combined with fluorescent microspheres for confirmation of injection site were directly injected into the renal parenchyma of PND1 mouse kidneys (FIG. 4A). Kidneys of the control mice were injected with control HK2-mCherry cells (HK2 cells transfected with a transposon carrying mCherry only and then subjected to the same reprogramming protocol) or fluorescent microspheres alone. Kidneys were harvested 3 and 7 days post-injection and successful injection was confirmed by the presence of fluorescent microspheres (FIG. 15). At 3 days post-injection, surviving cells were seen in both test (iNP) and control (HK2-mCherry) kidneys, with a proportion of these cells being integrated into developing tubules (defined by laminin-bound basement membrane) (FIG. 4B i).

However, by 7 days post-injection, no injected cells were observed in control kidneys despite the presence of fluorescent microspheres confirming that the suspension was delivered successfully (FIG. 4B ii), suggesting that HK2 cells were not able to successfully integrate into renal tubular epithelium in this assay. In contrast, abundant reprogrammed cells were observed at day 7, all of which were integrated into developing nephron structures (FIG. 4B ii, bottom panel). Reprogrammed cells contributed to both LTL$^+$ proximal and LTL$^-$ distal nephron segments (co-stained with laminin to mark tubule basement membranes), but showed a preference for proximal (95%) over distal (5%) portions (FIG. 4C). Of note was the formation of extended tubule segments by the reprogrammed cells and their binding of LTL on the apical brush border membrane, as would be expected for a mature proximal tubule. This data suggests that a subset of cells expressing the reprogramming transposon possessed nephrogenic differentiation capacity in vivo and had therefore been successfully dedifferentiated to iNPs.

Clonal Selection Identifies a Requirement for Only Three Genes to Efficiently Reprogram to iNPs The cells generated via transposon integration likely represent a polyclonal pool with considerable variation in transposon integration number, integration site and presumably success of reprogramming between individual cells. To overcome any resulting experimental variation, reprogrammed individual clones were derived using the same pool of stably transfected (pT-SOH, pT-SES and pT-TetON constructs) as used in previous experiments. FIG. 5A shows data from 12 reprogrammed clones subjected to iNP reprogramming. Endogenous gene expression analysis revealed wide variation in the expression of NP markers between clones with low levels of endogenous SIX2 expression in all but one clone, designated Clone 8 (FIG. 5A). In contrast to the other 11 clones, Clone 8 possessed increased expression of both SIX2 and CITED1, as well as a notably more mesenchymal morphology from day 5 of reprogramming (Clone 8 iNPs+dox; FIG. 5C). All subsequent experiments were performed using this optimally reprogrammable clone.

As the six critical transcription factors were delivered in two separate transposons (pT-SOH and pT-SES), clonal selection allowed us to correlate successful reprogramming with relative transposon integration levels. Transposon copy number analysis revealed very low levels of pT-SOH integration in nearly all clones. Clone 8 possessed the highest copy number of pT-SES (FIG. 5B), revealing an inverse correlation between pT-SES integration and MEOX2 expression (Clones 7 and 9) and positive correlations between pT-SES integration and CITED1 expression (Clones 3, 5 and 8) and pT-SOH integration and OSR1 expression (Clones 5 and 12). Clone 12 showed no evidence of NP marker expression above control and possessed the highest level of pT-SOH, suggesting that this construct had a detrimental effect on reprogramming to iNPs. Of note, in our previous combinatorial screen for reprogramming factors, the pT-SES factors transduced individually and the combination of SIX1 and SNAI2 were not found to be one of the 10 reprogramming pools able to induce CITED1 expression (Hendry et al, 2013). Similarly, cells transfected with SIX1 and EYA1 showed a small increase in SIX2 but not CITED1 expression (FIG. 11). Taken together, these data suggest that SNAI2, EYA1 and SIX1 are sufficient to induce SIX2 and CITED1 gene expression in HK2 cells and that reprogramming to iNPs could be achieved with these three factors alone when transposon copy number per cell was sufficient.

Clone 8 iNPs Show Improved NP Phenotype and a Capacity to Grow as 3D Aggregates after Culture in NP Maintenance Media To examine whether culture of iNPs in recently defined NP maintenance media was feasible, we cultured Clone 8 iNPs in each of three previously described media formulations; CDBLY (Tanigawa et al., 2016), NPEM (Brown et al., 2015) and NPSR (Li et al., 2015). Initially, complete replacement of the original basal media for all 8 days of the reprogramming protocol was trialed. However, this was found to have a negative effect on SIX2 expression (data not shown). Instead, NP-supportive media was added after initial reprogramming, from the time of induction of CITED1 protein expression (approximately day 5 post-doxycycline addition, refer to FIG. 3). This improved the expression of a range of NP genes in Clone 8 iNPs compared to HK2 growth media (HGM), with slightly different outcomes for each media formulation (FIG. 6A). Culture in NPEM improved SIX1, PAX2 and MEOX2, while CDBLY culture improved SIX1, PAX2, MEOX2 and CITED1. NPSR resulted in a greater improvement in global NP gene expression, both in the number of genes showing an increase above control (SALL1, SIX1, SIX2, EYA1, MEOX2 and OSR) and the level of this increase. Importantly, control cells lacking the reprogramming transposon but cultured in NPEM or CDBLY exhibited little induction in NP markers, highlighting the importance of having the reprogramming transposons present (FIG. 7A). NPSR alone increased the expression of some NP genes when compared to the other two media, but this induction was significantly lower than in Clone 8 iNPs cells for several key NP markers (FIG. 14B), suggesting a complementary effect between the media and transposon.

Several studies have now reported the generation of NP-like populations from pluripotent cell sources (Takasato et al., 2014, Lam et al., 2014, Taguchi et al., 2014, Morizane et al., 2015). To compare this approach to transposon-mediated iNPs, dermal fibroblast-derived iPSCs (CRL1502 clone C32) were differentiated towards kidney using our previously published directed differentiation protocol (Takasato et al., 2016). Whilst these differentiated iPSCs represent a mixed population of renal progenitors, when looking at NP markers alone, two genes recently shown to be important markers of human NPs, SIX1 and SIX2 (O'Brien et al., 2016), were both higher (approximately 5500- and 2-fold, respectively) in Clone 8 iNPs compared to iPSC-derived NPs (FIG. 6B).

When developing the NPSR media for NP maintenance, Li et al. (2016) showed that 3D aggregate culture of isolated NPs was the optimal culture condition with which to maintain NP identity. To investigate the response of directly reprogrammed cells to this culture system, Clone 8 iNPs were transferred to low attachment 96-well plates and cultured in NPSR. Within 3 days, Clone 8 iNPs formed tight spheres, continuing to proliferate and in some cases forming a single floating aggregate by 5 days of culture (FIG. 6C). In contrast, Clone-8 iNPs cultured in control media (HGM) and HK2-mCherry control cells cultured in NPSR could not be maintained in this fashion, highlighting the cooperation between the transposon reprogramming and the optimal media conditions.

Induction of a Nephron Progenitor-Like Transcriptional Profile

In order to further characterize the Clone 8 iNPs at a transcriptional level, RNAseq profiling was performed on parental Clone 8 cells without induction (no doxycycline, HGM media) in comparison to the same lines after doxycycline induction for 10 days and cultured in either control (HGM) or NP maintenance (NPSR) media. Profiling was performed in triplicate and a PCA analysis showed tight correlation of triplicates for each sample (FIG. 6Bi). Genes differentially expressed (log 2 threshold>1, FDR<0.05) between control uninduced clone 8 and both induced conditions were selected. An unbiased clustering revealed strong alignment in gene expression between the induced NPs compared with the uninduced parental clone (FIG. 4Bii). GO analysis (https://toppgene.cchmc.org/) using these genes revealed upregulation of a signature of 36 genes from within the top 500 genes enriched in isolated murine NPs (www.gudmap.org.au; P4 KidCapMesRenVes_Crym_top-relativeexpression-ranked_500) (FIG. 6Biii). This signature also included genes within the reprogramming transposons. While a specific analysis of these 6 transcription factors revealed evidence that all had been induced (FIG. 7D), expression was significantly higher for SIX1, EYA1 and SNAI2 (FIG. 6Biv). Together this data supports the view that these three genes are able to cause transdifferentiation to a NP state.

Clone 8 iNPs Show Nephrogenic Potential in Mouse and Human Organoids

While in vitro data supported a role for the addition of NP-maintenance media for sustained iNP culture, it was important to confirm the nephron forming capacity of the cells after NP media culture. To do this, we used two ex vivo differentiation assays; an embryonic mouse kidney organoid assay (Davies et al., 2012, Lusis et al., 2010) (FIG. 8A) and a novel human iPSC-derived kidney organoid assay utilizing our directed differentiation protocol that would enable us to examine iNP behavior in a more human context compared to mouse organoids (FIG. 9B). Prior to harvesting, organoids were briefly exposed to doxycycline to initiate the re-expression of mCherry by either Clone 8 iNPs or control cells. In mouse kidney organoids, reprogrammed cells were found to integrate into both LTL⁺ proximal nephron segments as well as LTL⁻ distal nephron segments (co-stained with the epithelial marker E-CADHERIN) when reprogramming was performed in either HGM, CDBLY, NPEM and NPSR (FIG. 8A). Consistent with the results of gene expression analysis, Clone 8 iNPs cultured in NPSR showed the greatest level of contribution, with extended tubule segments composed of reprogrammed cells, predominantly in proximal tubules. Within tubules, integrated cells also showed evidence of mature segment-specific functional proteins, including the distal tubule solute transporter, Slc12a1, and the proximal tubule endocytic receptor, Megalin (FIG. 14A). In contrast, HK2-mCherry control cells failed to contribute to nephrons, in some instances clustering together and causing disruption to organoid structure (FIGS. 14A and 14Bi). The integration capacity of Clone 8 cells (cultured in HGM without doxycycline induction) was similarly evaluated. These cells did not integrate or survive the duration of the experiment (FIG. 14B ii).

Similar to mouse kidney organoids, Clone 8 iNPs showed the capacity to differentiate and integrate into developing LTL⁺ proximal and LTL⁻ distal nephron segments in human iPSC-derived kidney organoids after culture in NPEM (FIG. 8B). However, despite the iNPs cultured in CDBLY being observed within tubular structures, these structures showed poorly defined basement membranes, particularly around sites of iNP integration (FIG. 8B, CDBLY panel). As would be expected for bona fide NPs, Clone 8 iNPs did not contribute to GATA3⁺ collecting duct (FIG. 8B, HGM panel), but were also absent from glomeruli. Once again, the ability of uninduced Clone 8 control cells without doxycycline exposure to integrate into developing nephrons was assessed and revealed no integration. These Clone 8 control cells without doxycycline were seen to cluster together within the interstitium at early time points and either did not survive until the experimental endpoint of 10 days organoid culture (HGM, CDBLY and NPEM) or remained clustered within the interstitium (NPSR) (FIG. 14C).

Clone 8 iNPs Contribute to Nephrons Following Acute Ischemic Injury

One potential application of iNPs is their use as a cellular therapy for patients with kidney disease. Delivery of iNPs may assist in the direct repair of damaged tubular epithelium and improve renal function. In order to assess the effect of Clone 8 iNPs on the damaged kidney, cells were directly injected into the renal parenchyma of adult NSG mice immediately following the induction of acute renal injury by 15 minutes of unilateral ischemia. Kidneys were then reperfused. At 10 days post injection, Clone 8 iNPs were found to integrate into LTL-positive proximal tubules and LTL-negative distal convoluted tubules of the kidney cortex (FIGS. 9Ai, Aii and C), but not glomeruli or collecting ducts. In contrast, very few control cells (Clone 8 uninduced cells subjected to identical reprogramming conditions but in HGM lacking doxycycline) were observed in the injected kidneys from 3 replicate mice (FIGS. 9Ai and C). In addition, substantially more structural damage, such as tubular cell detachment, necrosis and tubule dilation, was present 10 days post-IRI in the control kidneys near cell injection sites compared to the Clone 8 iNP-injected kidneys (FIG. 9B). These data not only suggest that Clone 8 iNPs were well-tolerated by adult NSG mice, but that these cells are capable of integration into cortical tubules of the renal parenchyma.

Refined Reprogramming and Culture Conditions can Generate iNPs from Primary Human Proximal Tubule Cells Primary human renal epithelial cells represent an accessible and reprogrammable cell source that can not only be isolated from patients through surgery or biopsy, but also through non-invasive urine collection methods (Zhou et al., 2012, reviewed in Oliveira Arcolino et al., 2015). We have previously demonstrated that normal human renal proximal tubule epithelial cells (hRPTECs) transduced with the six iNP reprogramming factors, SIX1, SIX2, OSR1, HOXA11, EYA1 and SNAI2, showed an increase in the expression of NP genes (Hendry et al., 2013). However, these cells did not integrate into endogenous kidney sub-compartments when assessed for nephron progenitor potential in mouse kidney organoid assays (data not shown). Having now developed an improved inducible reprogramming system and reduced the gene set to three factors, hRPTEC cells were subjected to the refined protocol and functionally assessed in the mouse kidney organoid assay (FIG. 11).

To achieve a high transfection efficiency, hRPTECs were electroporated with the pT-SES, pT-TetON and piggyBac transposase plasmids. Following 48 hours of recovery, transfected hRPTECs were exposed to the identical reprogramming protocol and media conditions (HGM followed by NPSR) as optimized for HK2 cells, then harvested at day 8 of reprogramming for the mouse kidney organoid assay. These cells showed a marked change in morphology and an increase in the expression of all NP markers except for PAX2 compared to parental hRPTECs (FIGS. 11A and B). However, PAX2 expression was similar to that of parental hRPTECs for which we have previously demonstrated high endogenous PAX2 levels (Hendry et al., 2013). In functional assays, transfected hRPTECs were observed in three separate kidney recombinations in a variety of locations. In particular, one organoid displayed abundant hRPTEC iNPs integrated within developing nephron structures marked by E-Cadherin (FIG. 11C). In contrast to HK2-derived iNPs, hRPTEC iNPs showed a preference for distal (31%) over proximal (3%) portions of the nephrons (FIG. 11D), but were absent from collecting duct (FIG. 15A). hRPTEC-mCherry control cells lacking the pT-SES construct, but subjected to the same reprogramming protocol, did not integrate into developing nephron structures (FIG. 15B). Taken together these data suggest that transposon-mediated reprogramming is transferrable to hRPTECs and represents a feasible option for iNP derivation from primary human cells.

Introduction of mouse transcription factors carried on the reprogramming transposon pT-mSES induced eGFP expression indicative of Cited1 positivity in a well-characterized transgenic mouse model containing a BAC transgene (FIG. 16). There were eGFP-positive cells with a similar morphology present in both QR-injected and pT-mSES-injected transgenic animals (FIG. 16, panels a and b). However, only in the pT-mSES-injected transgenic animals were there cells appearing to be derived from tubule-like structures that were eGFP-positive (FIG. 16c). In contrast, in wild-type, non-transgenic mice receiving either QR or pT-mSES, no positive eGFP cells could be found. Therefore, cellular reprogramming to an induced nephron progenitor state may be possible in vivo following gene delivery of Snai2, Six1 and Eya1.

DISCUSSION

Here we report the design of a piggyBac transposon-mediated system of reprogramming to iNPs. The resulting iNPs display nephrogenic potential both in vivo and in vitro in mouse kidney, integrate into tubules within human kidney organoids, and can contribute to tubules within damaged postnatal mouse kidney. Importantly, clonal analysis and transcriptional profiling suggested the requirement for re-expression of only three transcription factors to reprogram to iNPs: SNAI2, EYA1 and SIX1. This refinement is not only consistent with what we now know of mammalian kidney development, but is also interesting in a developmental context and considering our current knowledge of the requirements for successful NP culture in vitro.

It is understood that several proteins critical to the NP phenotype function during kidney development within transcriptional complexes and/or as upstream effectors of downstream NP-regulatory proteins. Loss of Six1 expression in mouse kidney results in a marked reduction of Six2, Pax2 and Sall1, but not Eya1, expression, leading to apoptosis of the metanephric mesenchyme (MM) (Li et al., 2003, Xu et al., 2015, Xu et al., 2003). Data from mouse models suggest that Six1 and Eya1 act upstream of these factors and form a transcriptionally active complex necessary for normal kidney development. This confirms a conserved regulatory mechanism between Six1 and Eya1 that has also been demonstrated by developmental studies of their homologs in drosophila eye (Chen et al., 1997, Pignoni et al., 1997) and human fetal kidney (O'Brien et al., 2016), as well as by gene co-transfection studies in vitro (Ohto et al., 1999). It therefore seems rational that forced reinstatement of such an evolutionarily conserved pathway in mature proximal tubule cells would be important for reprogramming to a NP-like state.

The ability to reprogram to iNPs in the absence of SIX2 was surprising given the critical role played by this gene in NP self-renewal and maintenance as shown in mouse kidney (Self et al., 2006, Kobayashi et al., 2008, Park et al., 2012) as well as the reported association between SIX2 mutation and both renal dysplasia and Wilms tumour (Walz et al., 2015, Weber et al., 2008, Wegert et al., 2015). However, it has been recently reported that the NPs of the human fetal kidney express both SIX1 and SIX2, whereas the SIX1 protein is not evident in the same region in the mouse (O'Brien et al., 2016). Interestingly, SIX1 was found to be one of the most highly regulated targets of SIX2 in human kidney, with both proteins likely to regulate a common set of NP genes through recognition of the same DNA binding motifs. However, whilst both proteins were found to complex with EYA1 as expected, they are likely to form independent regulatory complexes in vivo. Taken together, these data suggest that successful reprogramming to human iNPs in the absence of SIX2 may be attributed to the potential functional similarity between these proteins in human kidney and the fact that SIX1 expression may at least in part be directly activated by SIX2.

Despite a lack of evidence for the Six1 protein in mouse nephron progenitors, genetic loss of Six1 in mouse results in a marked reduction of Six2, Pax2 and Sall1, but not Eya1, leading to apoptosis of the metanephric mesenchyme (MM) (Li et al., 2003, Xu et al., 2015, Xu et al., 2003). Data from mouse models suggest that Six1 and Eya1 act upstream of these factors and form a transcriptionally active complex necessary for normal kidney development. This confirms a conserved regulatory mechanism between Six1 and Eya1 that has also been demonstrated by developmental studies of their homologs in drosophila eye (Chen et al., 1997, Pignoni et al., 1997) and human fetal kidney (O'Brien et al., 2016), as well as by gene co-transfection studies in vitro (Ohto et al., 1999).

Expression of Snai2 (Slug) in the endogenous mouse NP population is weak, instead showing strong expression in the cortical stroma (McMahon et al., 2008). However, SNAI2 was included in the original lentiviral screen due to its activity as an EMT regulatory factor (Savagner et al., 1997). While HK2 cells transduced with SNAI2 alone underwent a marked EMT, they did not adopt a NP-like phenotype (Hendry et al., 2013), suggesting the role of SNAI2 in the reprogramming pool to be related to inducing EMT. In support of this concept, studies of murine NP maintenance in vitro highlighted the favourable increase in Snai2 expression when isolated MM cells were treated with low levels of LIF (activating JAK/STAT signaling and maintaining nuclear SIX2) and the Rho kinase inhibitor Y27632 (inhibiting MET through the JNK-mediate differentiation pathway), a combination that is utilized in both CDBLY and NPSR NP-supportive media (Tanigawa et al., 2015). Thus, inclusion of SNAI2 in the reprogramming cocktail may serve to improve EMT in conjunction with NP-supportive media and enable EMT to occur in HGM in the absence of such signaling molecules and growth factors. As such, this factor may not be required if the starting cell population is not epithelial.

It is well-accepted that reprogramming can be imprecise as the transcriptional activity being imposed only serves to push the cell towards the desired attractor state/cellular endpoint (reviewed in Hendry et al., 2012). This also means that while there can be several ways to reach a desired endpoint, some transcription factor combinations may be more efficient than others. Given the possibility that the refined three-factor reprogramming pool is still suboptimal with respect to gene combination and/or stoichiometry, the addition of media selective for and supportive of NP maintenance is likely to have at least partially overcome these limitations. Indeed, whilst Clone 8 iNPs derived in HGM showed increased NP marker expression and contribution to nephron formation, improvement in the phenotype and behavior of these cells was evident when NP-supportive media was used.

It is likely that the refinement of the reprogramming system also played 376 a large part in its improved transferability to primary cells. hRPTECs reprogrammed using SNAI2, EYA1 and SIX1 and cultured in NPSR media showed phenotypic and functional characteristics of bona fide NPs. Interestingly, these cells showed a preference for integration into distal tubules over proximal tubules. This shift in segment preference compared to the HK2-derived iNPs, as well as lack of glomerular integration by these cell types despite displaying host of NP characteristics, may have arisen from differing stoichiometry of reprogramming factors between experiments or slight differences in their requirements in terms of the reprogramming factors themselves. Consistent with these notions, nephron segment identity of induced renal epithelial cells (iRECs) derived via direct transcriptional reprogramming of mouse embryonic fibroblasts has been found to be modulated by small alterations of the reprogramming factor cocktail (Kaminski et al., 2016). Having refined the gene set required to induce NPs, it will now be possible to look at the requirement for each factor individually in hRPTECs, potentially improving reprogramming efficiency further and expanding the protocol to additional starting cell types.

Inducible transposon approaches are of relevance for transdifferentiation to cellular endpoints other than kidney, as has been shown with the use of transposons for reprogramming to pluripotency (Woltjen et al., 2009). Here we demonstrate the use of inducible piggyBac-mediated reprogramming to iNPs. This represents a key breakthrough in the field as it may facilitate the large-scale generation of cells or tissues for renal regeneration. Indeed, it may also provide an approach to precisely generate specific individual cell types of the nephron. The discovery that iNPs survive and contribute to the renal tubules of acutely injured kidneys in adult mice highlights the possibility that transposon-induced iNPs may have cell therapy applications. Finally, the identification of these critical pioneer factors for the specification of NPs suggests the feasibility of direct cellular reprogramming in vivo.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

Tables

TABLE 1

Reprogramming factor gene names and corresponding accession numbers.

| Gene name | Symbol | Gene accession |
|---|---|---|
| Sine oculis homeobox 1 | SIX1 | NM_005982.3 |
| Sine oculis homeobox 2 | SIX2 | NM_016932.4 |
| Odd-skipped related 1 | OSR1 | NM_145260.2 |
| Homeobox A11 | HOXA11 | NM_005523.5 |
| Snail homolog 2 | SNAI2 | NM_003068.4 |
| Eyes absent homolog 1 | EYA1 | NM_17058.2 |
| Sine oculis homeobox 1 | Six1 | NM_009189.3 |
| Snail homolog 2 | Snai2 | NM_011415.2 |
| Eyes absent homolog 1 | Eya1 | NM_001310459.1 |

TABLE 3

Details of antibodies and lectins used for immunofluorescence and Western blot procedures.

| Specificity | Host species | Dilution range | Manufacturer and identifier |
|---|---|---|---|
| mCherry (RFP) | Rabbit | (IF) 1:200 - 1:400 (WB) 1:10,000 - 1:15,000 | MBL Medical & Biological Laboratories Co. Ltd. (PM005) |
| mCherry (RFP) | Mouse | (IF) 1:300 | MBL Medical & Biological Laboratories Co. Ltd. (M208-3) |
| CITED1 | Rabbit | (IF) 1:200 - 1:300 | Thermo Fisher Scientific (RB-9219-P1) |
| PAX2 | Rabbit | (IF) 1:200 - 1:300 | Zymed Laboratories, Inc. (71-600) |
| SIX2 | Rabbit | (IF) 1:200 - 1:300 (WB) 1:1000 | Proteintech Group (11562-1-AP) |
| EYA1 | Goat | (IF) 1:200 - 1:300 (WB) 1:500 - 1:1000 | Abcam (Ab99186) |
| Laminin | Rabbit | (IF) 1:200 - 1:300 | Sigma-Aldrich (L9393) |
| Human mitochondrial antigen | Mouse | (IF) 1:200 - 1:400 | Abcam (Ab92824) |
| Human nuclear antigen | Mouse | (IF) 1:300 | Abnova (MAB8178) |
| Proximal tubule brush border membrane | Lotus tetragonobulus lectin (LTA) | (IF) 1:200 - 1:400 | Vector Laboratories (B-1325) |
| E-Cadherin | Mouse | (IF) 1:200 - 1:300 | BD Biosciences (610181) |
| SNAI2 | Rabbit | (IF) 1:200 - 1:300 (WB) 1:500 - 1:1000 | Cell Signaling Technologies (C19G7) |
| HOXA11 | Mouse | (IF) 1:200 - 1:300 (WB) | Abnova (H00003207-M05) |
| 2A peptide | Rabbit | (WB) 1:10,000 - 1:15,000 | Merck Millipore (ABS31) |
| Slc12a1 | Rabbit | (IF) 1:300 | Proteintech (18970-1-AP) |
| Megalin | Mouse | (IF) 1:300 | Novus Biological (NB110-96417) |
| GFP | Goat | (IF) 1:1000 | Abcam (ab5450) |

(WB; Western blot, IF; Immunofluorescence)

TABLE 2

Nucleotide and protein sequences for each 2A sequence in the reprogramming transposons.

| 2A | Nucleotide sequence (5'→3') | Translation |
|---|---|---|
| GSG-P2A | GGATCCGGAGCCACGAACTTCTCTCTGTTAAAGCAAGCAGGAGACGTGGAAGAAAACCCCGGTCCC (SEQ ID NO: 21) | GSGATNFSLLKQAGDVEENPGP (SEQ ID NO: 25) |
| GSG-T2A | GGCTCCGGATCCGGAGAGGGCAGAGGAAGTCTGCTAACATGCGGTGACGTCGAGGAGAATCCTGGCCCA (SEQ ID NO: 22) | GSGSGEGRGSLLTCGDVEENPGP (SEQ ID NO: 26) |
| Pm2A | GCTACCAATTTTAGCTTGCTCAAACAGGCCGGGGATGTTGAGGAAAATCCAGGACCG (SEQ ID NO: 23) | ATNFSLLKQAGDVEENPGP (SEQ ID NO: 27) |
| Tm2A | GAAGGTCGTGGCTCCTTGTTGACCTGTGGCGATGTGGAAGAAAACCCAGGCCCT (SEQ ID NO: 24) | EGRGSLLTCGDVEENPGP (SEQ ID NO: 28) |
| F2A | GTGAAACAGACTTTGAATTTTGACCTTCTCAAGTTGGCGGGAGACGTGGAGTCCAACCCAGGGCCC (SEQ ID NO: 10) | VKQTLNFDLLKLAGDVESNPGP (SEQ ID NO: 29) |
| E2A | CAATGTACTAACTACGCTTTGTTGAAACTCGCTGGCGATGTTGAAAGTAACCCCGGTCCT (SEQ ID NO: 11) | QCTNYALLKLAGDVESNPGP (SEQ ID NO: 30) |

NUCLEOTIDE SEQUENCES iNP reprogramming factors
hSNAI2 (NM_003068.4; SEQ ID NO: 1)
ATGCCGCGCTCCTTCCTGGTCAAGAAGCATTTCAACGCCTCCAAAAAGCCAAACTACAGC
GAACTGGACACACATACAGTGATTATTTCCCCGTATCTCTATGAGAGTTACTCCATGCCT
GTCATACCACAACCAGAGATCCTCAGCTCAGGAGCATACAGCCCCATCACTGTGTGGAC
TACCGCTGCTCCATTCCACGCCCAGCTACCCAATGGCCTCTCTCCTCTTTCCGGATACTCC
TCATCTTTGGGGCGAGTGAGTCCCCCTCCTCCATCTGACACCTCCTCCAAGGACCACAGT
GGCTCAGAAAGCCCCATTAGTGATGAAGAGGAAAGACTACAGTCCAAGCTTTCAGACCC
CCATGCCATTGAAGCTGAAAAGTTTCAGTGCAATTTATGCAATAAGACCTATTCAACTTT
TTCTGGGCTGGCCAAACATAAGCAGCTGCACTGCGATGCCCAGTCTAGAAAATCTTTCAG
CTGTAAATACTGTGACAAGGAATATGTGAGCCTGGGCGCCCTGAAGATGCATATTCGGA
CCCACACATTACCTTGTGTTTGCAAGATCTGCGGCAAGGCGTTTTCCAGACCCTGGTTGC
TTCAAGGACACATTAGAACTCACACGGGGGAGAAGCCTTTTTCTTGCCCTCACTGCAACA
GAGCATTTGCAGACAGGTCAAATCTGAGGGCTCATCTGCAGACCCATTCTGATGTAAAG
AAATACCAGTGCAAAAACTGCTCCAAAACCTTCTCCAGAATGTCTCTCCTGCACAAACAT
GAGGAATCTGGCTGCTGTGTAGCACACTGA (EXCLUDED STOP CODON)
Length estimate. 807 bp (Protein = 30.01 kDa)

hSIX1 (NM_005982.3; SEQ ID NO: 2)
ATGTCGATGCTGCCGTCGTTTGGCTTTACGCAGGAGCAAGTGGCGTGCGTGTGCGAGGTT
CTGCAGCAAGGCGGAAACCTGGAGCGCCTGGGCAGGTTCCTGTGGTCACTGCCCGCCTG
CGACCACCTGCACAAGAACGAGAGCGTACTCAAGGCCAAGGCGGTGGTCGCCTTCCACC
GCGGCAACTTCCGTGAGCTCTACAAGATCCTGGAGAGCCACCAGTTCTCGCCTCACAACC
ACCCCAAACTGCAGCAACTGTGGCTGAAGGCGCATTACGTGGAGGCCGAGAAGCTGCGC
GGCCGACCCCTGGGCGCCGTGGGCAAATATCGGGTGCGCCGAAAATTTCCACTGCCGCG
CACCATCTGGGACGGCGAGGAGACCAGCTACTGCTTCAAGGAGAAGTCGAGGGGTGTCC
TGCGGGAGTGGTACGCGCACAATCCCTACCCATCGCCGCGTGAGAAGCGGGAGCTGGCC
GAGGCCACCGGCCTCACCACCACCCAGGTCAGCAACTGGTTTAAGAACCGGAGGCAAAG
AGACCGGGCCGCGGAGGCCAAGGAAAGGGAGAACACCGAAAACAATAACTCCTCCTCC
AACAAGCAGAACCAACTCTCTCCTCTGGAAGGGGGCAAGCCGCTCATGTCCAGCT
CAGAAGAGGAATTCTCACCTCCCCAAAGTCCAGACCAGAACTCGGTCCTTCTGCTGCAG
GGCAATATGGGCCACGCCAGGAGCTCAAACTATTCTCTCCCGGGCTTAACAGCCTCGCA
GCCCAGTCACGGCCTGCAGACCCACCAGCATCAGCTCCAAGACTCTCTGCTCGGCCCCCT
CACCTCAGTCTGGTGGACTTGGGGTCCTAA (EXCLUDED STOP CODON)
Length estimate: 855 bp (Protein = 32.22 kDa)

hEYA1 (NM_172058.2; SEQ ID NO: 3)
ATGGAAATGCAGGATCTAACCAGCCCGCATAGCCGTCTGAGTGGTAGTAGTGAATCCCC
CAGTGGCCCCAAACTCGGTAACTCTCATATAAATAGTAATTCCATGACTCCCAATGGCAC
CGAAGTTAAAACAGAGCCAATGAGCAGCAGTGAAACAGCTTCAACGACAGCCGACGGG
TCTTTAAACAATTTCTCAGGTTCAGCAATTGGGAGCAGTAGTTTCAGCCCACGACCAACT
CACCCAGTTCTCTCCACCACAGATTTACCCTTCCAACAGACCCATACCCACATATTCTCCCTA
CCCCTTCCTCACAAACTATGGCTGCATATGGGCAAACACAGTTTACCACAGGAATGCAAC
AAGCTACAGCCTATGCCACGTACCCACAGCCAGGACAGCCGTACGGCATTTCCTC
ATATGGTGCATTGTGGGCAGGCATCAAGACTGAAGGTGGATTGTCACAGTCTCAGTCAC
CTGGACAGACAGGATTTCTCAGCTATGGCACAAGCTTCAGTACCCCTCAACCTGGACAG
GCACCATACAGCTACCAGATGCAAGGTAGCAGTTTTACAACATCATCAGGAATATATAC
AGGAAATAATTCACTCACAAATTCCTCTGGATTTAATAGTTCACAGCAGGACTATCCGTC
TTATCCCAGTTTTGGCCAGGGTCAGTACGCACAGTATTATAACAGCTCACCGTATCCAGC
ACATTATATGACCAGCAGCAACACCAGCCCAACGACACCATCCACCAATGCCACTTACC
AGCTTCAAGAACCGCCATCTGGCATCACCAGCCAAGCAGTTACAGATCCCACAGCAGAG
TACAGCACAATCCACAGCCCATCAACACCCATTAAAGATTCAGATTCTGATCGATTGCGT
CGAGGTTCAGATGGGAAATCACGTGGACGGGCCGAAGAAACAATAATCCTTCACCTCC
CCCAGATTCTGATCTTGAGAGAGTGTTCATCTGGGACTTGGATGAGACAATCATTGTTTT
CCACTCCTTGCTTACTGGGTCCTACGCCAACAGATATGGGAGGGATCCACCCACTTCAGT
TTCCCTTGGACTGCGAATGGAAGAAATGATTTTCAACTTGGCAGACACATTTATTTTT
TAATGACTTAGAAGAATGTGACCAAGTCCATATAGATGATGTTTCTTCAGATGATA
ACGGACAGGACCTAAGCACATATAACTTTGGAACAGATGGCTTTCCTGCTGCAGCAACC
AGTGCTAACTTATGTTTGGCAACTGGTGTACGGGGCGGTGTGGACTGGATGAGAAAGTT
GGCCTTCCGCTACAGACGGGTAAAAGAGATCTACAACACCTACAAAAATAATGTTGGAG
GTCTGCTTGGTCCAGCTAAGAGGGAAGCCTGGCTGCAGTTGAGGGCCGAAATTGAAGCC
CTGACCGACTCCTGGTTGACACTGGCCCTGAAAGCACTCTCGCTCATTCACTCCCGGACA
AACTGTGTGAATATTTTAGTAACAACTACTCAGCTCATCCCAGCATTGGCGAAA
GTCCTGCTGTATGGGTTAGGAATTGTATTTCCAATAGAAAATATTTACAGTGCAACTAAA
ATAGGAAAAGAAAGCTGTTTTGAGAGAATAATTCAAAGGTTTGGAAGAAAAGTGGTGTA
TGTTGTTATAGGAGATGGTGTAGAAGAAGAACAAGGAGCAAAAAAGCACGCGATGCCCT
TCTGGAGGATCTCCAGCCACTCGGACCTCATGGCCCTGCACCATGCCTTGGAACTGGAGT
ACCTGTAA (EXCLUDED STOP CODON)
Length estimate: 1776 bp (Protein = 64.59 kDa)

Inverted repeats
piggyBac 3' inverted terminal repeat (SEQ ID NO: 4)
(Length: 236 bp, complement strand on vector)
TTAACCCTAGAAAGATAATCATATTGTGACGTACGTTAAAGATAATCATGCGTAAAATTG
ACGCATGTGTTTTATCGGTCTGTATATCGAGGTTTATTTATTAATTTGAATAGATATTAAG
TTTTATTATATTTACACTTACATACTAATAATAAATTCAACAACAATTTATTTATGTTTA
TTTATTTATTAAAAAAAAACAAAAACTCAAAATTTCTTCTATAAAGTAACAAAA

NUCLEOTIDE SEQUENCES piggyBac 5' inverted terminal repeat (SEQ ID NO: 5)
(Length: 311 bp)
TTAACCCTAGAAAGATAGTCTGCGTAAAATTGACGCATGCATTCTTGAAATATTGCTCTC
TCTTTCTAAATAGCGCGAATCCGTCGCTGTGCATTTAGGACATCTCAGTCGCCGCTTGGA
GCTCCCGTGAGGCGTGCTTGTCAATGCGGTAAGTGTCACTGATTTTGAACTATAACGACC
GCGTGAGTCAAAATGACGCATGATTATCTTTTACGTGACTTTTAAGATTTAACTCATACG
ATAATTATATTGTTATTTCATGTTCTACTTACGTGATAACTTATTATATATATTTTCTTG
TTATAGATA Promoter
Tight-TRE (SEQ ID NO: 6)
CGAGTTTACTCCCTATCAGTGATAGAGAACGTATGTCGAGTTTACTCCCT
ATCAGTGATAGAGAACGATGTCGAGTTTACTCCCTATCAGTGATAGAGAA
CGTATGTCGAGTTTACTCCCTATCAGTGATAGAGAACGTATGTCGAGTTT
ACTCCCTATCAGTGATAGAGAACGTATGTCGAGTTTATCCCTATCAGTGA
TAGAGAACGTATGTCGAGTTTACTCCCTATCAGTGATAGAGAACGTATGT
CGAGGTAGGCGTGTACGGTGGGAGGCCTATATAAGCAGAGCTCGTTTAGT
GAACCGTCAGATCGCC
Length estimate: 316 bp Fluorescent reporter
mCherry (SEQ ID NO: 7)
ATGGTGAGCAAGGGCGAGGAGGATAACATGGCCATCATCAAGGAGTTCATGCGCTT
CAAGGTGCACATGGAGGGCTCCGTGAACGGCCACGAGTTCGAGATCGAGGGCGAGG
GCGAGGGCCGCCCCTACGAGGGCACCCAGACCGCCAAGCTGAAGGTGACCAAGGGT
GGCCCCCTGCCCTTCGCCTGGGACATCCTGTCCCCTCAGTTCATGTACGGCTCCAAGG
CCTACGTGAAGCACCCCGCCGACATCCCCGACTACTTGAAGCTGTCCTTCCCCGAGG
GCTTCAAGTGGGAGCGCGTGATGAACTTCGAGGACGGCGGCGTGGTGACCGTGACC
CAGGACTCCTCCCTGCAGGACGGCGAGTTCATCTACAAGGTGAAGCTGCGCGGCACC
AACTTCCCCTCCGACGGCCCCGTAATGCAGAAGAAGACCATGGGCTGGGAGGCCTCC
TCCGAGCGGATGTACCCCGAGGACGGCGCCCTGAAGGGCGAGATCAAGCAGAGGCT
GAAGCTGAAGGACGGCGGCCACTACGACGCTGAGGTCAAGACCACCTACAAGGCCA
AGAAGCCCGTGCAGCTGCCCGGCGCCTACAACGTCAACATCAAGTTGGACATCACCT
CCCACAACGAGGACTACACCATCGTGGAACAGTACGAACGCGCCGAGGGCCGCCAC
TCCACCGGCGGCATGGACGAGCTGTACAAGTAA (EXCLUDED STOP CODON)
Length estimate: 711

Poly-A tail
sV40 polyA (SEQ ID NO: 8)
TACCACATTTGTAGAGGTTTTACTTGCTTTAAAAAACCTCCCACACCTCC
CCCTGAACCTGAAACATAAAATGAATGCAATTGTTGTTGTTAACTTGTTT
ATTGCAGCTTATAATGGTTACAAATAAAGCAATAGCATCACAAATTTCAC
AAATAAAGCATTTTTTTCACTGCC
Length estimate: 174 bp Intervening 2A sequences
P2A(SEQ ID NO: 9)
GCCACGAACTTCTCTCTGTTAAAGCAAGCAGGAGACGTGGAAGAAAACCCCGGTCCC
Length estimate: 57 bp F2A(SEQ ID NO: 10)
GTGAAACAGACTTTGAATTTTGACCTTCTCAAGTTGGCGGGAGACGTGGAGTCCAACCCA
GGGCCC
Length estimate: 66 bp E2A(SEQ ID NO: 11)
CAATGTACTAACTACGCTTTGTTGAAACTCGCTGGCGATGTTGAAAGTAACCCCGGTCCT
Length estimate: 60 bp pT-mSES entire sequence (SEQ ID NO: 12)
TTAACCCTAGAAAGATAGTCTGCGTAAAATTGACGCATGCATTCTTGAAATATTGCTCTC
TCTTTCTAAATAGCGCGAATCCGTCGCTGTGCATTTAGGACATCTCAGTCGCCGCTTGGA
GCTCCCGTGAGGCGTGCTTGTCAATGCGGTAAGTGTCACTGATTTTGAACTATAACGACC
GCGTGAGTCAAAATGACGCATGATTATCTTTTACGTGACTTTTAAGATTTAACTCATACG
ATAATTATATTGTTATTTCATGTTCTACTTACGTGATAACTTATTATATATATTTTCTTG
TTATAGATATCATCAACTTTGTATAGAAAAGTTGGGCTCCGGTGCCCGTCAGTGGGCAGA
GCGCACATCGCCCACAGTCCCCGAGAAGTTGGGGGGAGGGGTCGGCAATTGAACCGGTG
CCTAGAGAAGGTGGCGCGGGGTAAACTGGGAAAGTGATGTCGTGTACTGGCTCCGCTT
TTTCCCGAGGGTGGGGAGAACCGTATATAAGTGCAGTAGTCGCCGTGAACGTTCTTTTT
CGCAACGGGTTTGCCGCCAGAACACAGGTAAGTGCCGTGTGTGGTTCCCGCGGGCCTGG
CCTCTTTACGGGTTATGGCCCTTGCGTGCCTTGAATTACTTCCACCTGGCTGCAGTACGTG
ATTCTTGATCCCGAGCTTCGGGTTGGAAGTGGGTGGGAGAGTTCGAGGCCTTGCGCTTAA
GGAGCCCCTTCGCCTCGTGCTTGAGTTGAGGCCTGGCCTGGGCGCTGGGGCCGCCGCGTG
CGAATCTGGTGGCACCTTCGCGCCTGTCTCGCTGCTTTCGATAAGTCTCTAGCCATTTAAA
ATTTTTTGATGACCTGCTGCGACGCTTTTTTTCTGGCAAGATAGTCTTGTAAATGCGGGCCA
AGATCTGCACACTGGTATTTCGGTTTTTGGGGCCGCGGGCGGCGACGGGCCCGTGCGTC

| NUCLEOTIDE SEQUENCES |
|---|
| CCAGCGCACATGTTCGGCGAGGCGGGGCCTGCGAGCGCGGCCACCGAGAATCGGACGG |
| GGGTAGTCTCAAGCTGGCCGGCCTGCTCTGGTGCCTGGTCTCGCGCCGCCGTGTATCGCC |
| CCGCCCTGGGCGGCAAGGCTGGCCCGGTCGGCACCAGTTGCGTGAGCGGAAAGATGCC |
| GCTTCCCGGCCCTGCTGCAGGGAGCTCAAAATGGAGGACGCGGCGCTCGGGAGAGCGGG |
| CGGGTGAGTCACCCACACAAAGGAAAAGGGCCTTTCCGTCCTCAGCCGTCGCTTCATGTG |
| ACTCCACGGAGTACCGGGCGCCGTCCAGGCACCTCGATTAGTTCTCGAGCTTTTGGAGTA |
| CGTCGTCTTTAGGTTGGGGGGAGGGGTTTTATGCGATGGAGTTTCCCCACACTGAGTGGG |
| TGGAGACTGAAGTTAGGCCAGCTTGGCACTTGATGTAATTCTCCTTGGAATTTGCCCTTTT |
| TGAGTTTGGATCTTGGTTCATTCTCAAGCCTCAGACAGTGGTTCAAAGTTTTTTTCTTCCA |
| TTTCAGGTGTCGTGACAAGTTTGTACAAAAAAGCAGGCTGCCACCATGCCGCGCTCCTTC |
| CTGGTCAAGAAACATTTCAACGCCTCCAAGAAGCCCAACTACAGCGAACTGGACACACA |
| CACAGTTATTATTTCCCCATATCTCTATGAAAGTTACCCCTATACCTGTCATACCAAAACCA |
| GAGATCCTCACCTCGGGAGCATACAGCCCTATTACTGTATGGACATCGTCGGCAGCTCCA |
| CTCCACTCTCCTTTACCCAGTGGCCTTTCTCCTCTTACTGGATACTCCTCATCCTTGGGGC |
| GTGTAAGTCCCCCGCCTTCCTCTGACACTTCATCCAAGGATCACAGTGGTTCAGAAAGTC |
| CCATTAGTGACGAAGAGGAGAGACTGCAGCCCAAGCTTTCAGACCCCCATGCCATCGAA |
| GCTGAGAAGTTTCAGTGCAATTTATGCAATAAGACCTATTCTACGTTCTCTGGGCTGGCC |
| AAACACAAGCAGCTGCACTGTGATGCCCAGTCTAGGAAATCGTTCAGCTGCAAGTACTG |
| TGACAAGGAATATGTGAGCCTGGGTGCCCTGAAGATGCACATTCGAACCCACACATTGC |
| CTTGTGTCTGCAAGATCTGTGGCAAGGCTTTCTCCAGACCCTGGCTGCTTCAAGGACACA |
| TTAGAACTCACACTGGGGAAAAGCCTTTCTCTTGCCCTCACTGCAATAGGGCTTTTGCAG |
| ACAGATCAAACCTGAGGGCACATCTGCAGACCCACTCTGATGTAAAGAAATACCAGTGC |
| AAAAACTGCTCCAAAACCTTCTCCAGAATGTCGCTTCTGCATAAACATGAGGAGTCTGGC |
| TGCTGTGTGGCACACGGAAGCGGAGTGAAACAGACTTTGAATTTTGACCTTCTGAAGTTG |
| GCAGGAGACGTTGAGTCCAACCCTGGGCCCATGGAAATGCAGGATCTAACCAGCCCGCA |
| TAGCCGACTGAGTGGTAGTAGCGAATCCCCCAGTGGTCCCAAACTCGATAGCTCTCATAT |
| AAATAGTACTTCCATGACTCCCAATGGCACCGAAGTTAAAACAGAGCCAATGAGCAGCA |
| GTGAAATAGCTTCAACAGCAGCAGACGGGTCTTTAGACAGTTTCTCAGGTTCAGCTCTCG |
| GAAGCAGCAGCTTTAGTCCAAGACCAGCTCACCCGTTCTCTCCACCACAGATTTATCCTT |
| CCAAATCATACCCACATATTCTCCCTACCCCTTCCTCACAAACTATGGCTGCATATGGGC |
| AAACACAGTTTACCACAGGAATGCAACAAGCCACAGCCTACGCCACGTACCCACAGCCT |
| GGACAGCCCTATGGAATTTCCTCCTATGGTGCATTGTGGGCAGGCATCAAGACGGAAAG |
| TGGATTGTCACAGTCTCAGTCACCTGGACAGACGGGATTTCTTAGCTATGGCACAAGCTT |
| TGGTACCCCTCAACCTGGACAGGCACCGTACAGCTACCAGATGCAAGGTAGCAGCTTTA |
| CCACGTCATCAGGATTATATTCAGGAAATAATTCACTCACCAACTCCTCCGGATTCAACA |
| GTTCACAGCAGGACTATCCGTCTTATCCCGGCTTTGGCCAGGGTCAGTACGCACAGTATT |
| ATAACAGCTCGCCGTATCCAGCACACTACATGACGAGCAGTAACACCAGCCCGACCACA |
| CCGTCCACCAATGCCACTTACCAACTCCAGGAACCACCTCTGGCGTCACAAGTCAGGCG |
| GTCACAGACCCCACAGCAGAGTACAGTACAATCCACAGTCCTTCCACACCCATTAAAGA |
| GACTGACTCCGAGCGGCTGCGTCGAGGTTCAGATGGGAAGTCACGTGGCCGAGGCAGAA |
| GAAACAATAATCCCTCCCCTCCCCCGGATTCTGACCTTGAGGAGTGTTCATCTGGGACC |
| TGGACGAGACCATCATTGTTTTCCACTCCTTGCTCACGGGGTCCTACGCCAACAGATACG |
| GGAGGGATCCACCTACTTCTGTTTCCCTGGGACTACAATGGAAGAGATGATTTTCAACT |
| TGGCAGACACACATCTATTTTTCAATGACCTAGAAGAGTGTGACCAAGTCCATATAGATG |
| ATGTTTCATCGACGACAACGGCCAGGACCTGAGCACATACAACTTTGGAACAGATGGC |
| TTTCCTGCTGCAGCCACCAGTGCTAATTTATGCCTGGCAACTGGTGTCCGAGGTGGTGTG |
| GACTGGATGCGGAAACTGGCCTTCCGCTACAGACGAGTAAAAGAGATCTACAACACCTA |
| CAAAAACAACGTGGGAGGTCTGCTTGGCCCAGCTAAGAGGGAAGCCTGGCTCCAGCTGA |
| GGGCTGAGATTGAGGCACTCACAGACTCCTGGCTGACCCTGGCCCTGAAGGCCCTCTCCC |
| TCATCCACTCCCGGACGAACTGTGTGAATATTTTAGTAACAACTACGCAGCTCATCCCAG |
| CATTGGCAAAGTCCTGCTATATGGATTAGGAATTGTGTTTCCAATAGAAAATATTTACA |
| GTGCAACTAAAATAGGAAAGGAAAGCTGTTTTGAGAGGATAATCCAAAGGTTTGGAAGG |
| AAAGTGGTATACGTTGTCATAGGAGATGGTGTGGAAGAAGAGCAAGGGGCAAAAAAGC |
| ATGCTATGCCCTTCTGGAGGGTCTCCAGTCACTCGGACCTCATGGCACTGCATCATGCCT |
| TGGAATTAGAGTACCTGGGAAGCGGACAGTGTACTAATTATGCTCTCTTGAAATTGGCTG |
| GAGATGTTGAGAGCAACCCAGGTCCCATGTCGATGCTGCCGTCGTTTGGTTTTACGCAAG |
| AGCAAGTGGCGTGCGTGTGCGAAGTTCTGCAGCAAGGAGGGAACCTGGAACGCCTGGGC |
| AGGTTCTTGTGGTCGTTGCCCGCCTGCGATCACCTGCACAAGAACGAGAGCGTGCTCAAG |
| GCCAAGGCGGTGGTCGCCTTCCACCGCGGCAACTTCCGCGAGCTCTACAAGATACTGGA |
| GAGCCACCAGTTCTCGCCTCACAATCACCCCAAACTGCAGCAGCTGTGGCTGAAAGCGC |
| ACTACGTGGAGGCCGAGAAACTTCGCGGCCGACCCCTGGGTGCCGTGGGCAAATATCGG |
| GTGCGCCGAAAATTCCCGTTGCCGCGGACCATCTGGGACGGCGAGGAGACCAGCTACTG |
| CTTTAAGGAGAAGTCTCGGGGCGTGCTGCGGGAGTGGTACGCGCACAACCCCTACCCCT |
| CACCGAGGGAGAAACGGGAGCTGGCCGAGGCCACCGGCCTCACCACCACCCAGGTCAG |
| CAACTGGTTTAAGAACCGGAGGCAAAGAGACCGGGCCGCCGAGGCCAAGGAAAGGGAG |
| AACACCGAAAACAATAACTCCTCCTCAACAAGCAGAATCAACTCTCTCCTCTGGAAGG |
| GGGCAAGCCGCTCATGTCCAGCTCAGAAGAGGAGTTCTCACCCCCCAAAGTCCAGACC |
| AGAACTCGGTCCTTCTGCTCCAGAGCAATATGGGCCACGCCAGGAGCTCAAACTATTCTC |
| TTCCAGGCCTCACAGCCTCCCAGCCCAGCCACGGTCTGCAAGCCCATCAGCACCAGCTCC |
| AGGACTCTCTGCTGGGCCCACTCACCTCCAGTTTGGTGGACTTGGGTTCCTAAACCCAGC |
| TTTCTTGTACAAAGTGGTGATCCTCAGGTGCAGGCTGCCTATCAGAAGGTGGTGGCTGGT |
| GTGGCCAATGCCCTGGCTCACAAATACCACTGAGATCTTTTCCCTCTGCCAAAAATTAT |
| GGGGACATCATGAAGCCCCTTGAGCATCTGACTTCTGGCTAATAAAGGAAATTTATTTTC |
| ATTGCAATAGTGTGTTGGAATTTTTTGTGTCTCTCACTCGGAAGGACATATGGGAGGGCA |
| AATCATTTAAAACATCAGAATGAGTATTTGGTTTAGAGTTTGGCAACATATGCCCATATG |
| CTGGCTGCCATGAACAAAGGTTGGCTATAAAGAGGTCATCAGTATATGAAACAGCCCCC |
| TGCTGTCCATTCCTTATTCCATAGAAAAGCCTTGACTTGAGGTTAGATTTTTTTATATTT |

| NUCLEOTIDE SEQUENCES |
|---|
| TGTTTTGTGTTATTTTTTTCTTTAACATCCCTAAAATTTTCCTTACATGTTTTACTAGCCAG |
| ATTTTTCCTCCTCTCCTGACTACTCCCAGTCATAGCTGTCCCTCTTCTCTTATGGAGATCCC |
| TCGACCTGCAGCCCAAGCTTGGATCCCTCGAGTTAATTAACGAGAGCATAATATTGATAT |
| GTGCCAAAGTTGTTTCTGACTGACTAATAAGTATAATTTGTTTCTATTATGTATAGGTTAA |
| GCTAATTACTTATTTTATAATACAACATGACTGTTTTTAAAGTACAAAATAAGTTTATTTT |
| TGTAAAAGAGAGAATGTTTAAAAGTTTTGTTACTTTATAGAAGAAATTTTGAGTTTTTGT |
| TTTTTTTTAATAAATAAATAAACATAAATAAATTGTTTGTTGAATTTATTATTAGTATGTA |
| AGTGTAAATATAATAAAACTTAATATCTATTCAAATTAATAAATAAACCTCGATATACAG |
| ACCGATAAAACACATGCGTCAATTTTACGCATGATTATCTTTAACGTACGTCACAATATG |
| ATTATCTTTCTAGGGTTAAATAATAGTTTCTAATTTTTTTATTATTCAGCCTGCTGTCGTG |
| AATACCGAGCTCCAATTCGCCCTATAGTGAGTCGTATTACAATTCACTGGCCGTCGTTTT |
| ACAACGTCGTGACTGGGAAAACCCTGGCGTTACCCAACTTAATCGCCTTGCAGCACATCC |
| CCCTTTCGCCAGCTGGCGTAATAGCGAAGAGGCCCGCACCGATCGCCCTTCCCAACAGTT |
| GCGCAGCCTGAATGGCGAATGGGACGCGCCCTGTAGCGGCGCATTAAGCGCGGCGGGTG |
| TGGTGGTTACGCGCAGCGTGACCGCTACACTTGCCAGCGCCCTAGCGCCCGCTCCTTTCG |
| CTTTCTTCCCTTCCTTTCTCGCCACGTTCGCCGGCTTTCCCCGTCAAGCTCTAAATCGGGG |
| GCTCCCTTTAGGGTTCCGATTTAGTGCTTTACGGCACCTCGACCCCAAAAAACTTGATTA |
| GGGTGATGGTTCACGTAGTGGGCCATCGCCCTGATAGACGGTTTTTCGCCCTTTGACGTT |
| GGAGTCCACGTTCTTTAATAGTGGACTCTTGTTCCAAACTGGAACAACACTCAACCCTAT |
| CTCGGTCTATTCTTTTGATTTATAAGGGATTTTGCCGATTTCGGCCTATTGGTTAAAAAT |
| GAGCTGATTTAACAAAAATTTAACGCGAATTTTAACAAAATATTAACGCTTACAATTTAG |
| GTGGCACTTTTCGGGGAAATGTGCGCGGAACCCCTATTTGTTTATTTTTCTAAATACATTC |
| AAATATGTATCCGCTCATGAGACAATAACCCTGATAAATGCTTCAATAATATTGAAAAA |
| GGAAGAGTATGAGTATTCAACATTTCCGTGTCGCCCTTATTCCCTTTTTTGCGGCATTTTG |
| CCTTCCTGTTTTTGCTCACCCAGAAACGCTGGTGAAAGTAAAAGATGCTGAAGATCAGTT |
| GGGTGCACGAGTGGGTTACATCGAACTGGATCTCAACAGCGGTAAGATCCTTGAGAGTT |
| TTCGCCCCGAAGAACGTTTTCCAATGATGAGCACTTTTAAAGTTCTGCTATGTGGCGCGG |
| TATTATCCCGTATTGACGCCGGGCAAGAGCAACTCGGTCGCCGCATACACTATTCTCAGA |
| ATGACTTGGTTGAGTACTCACCAGTCACAGAAAAGCATCTTACGGATGGCATGACAGTA |
| AGAGAATTATGCAGTGCTGCCATAACCATGAGTGATAACACTGCGGCCAACTTACTTCTG |
| ACAACGATCGGAGGACCGAAGGAGCTAACCGCTTTTTTGCACAACATGGGGGATCATGT |
| AACTCGCCTTGATCGTTGGGAACCGGAGCTGAATGAAGCCATACCAAACGACGAGCGTG |
| ACACCACGATGCCTGTAGCAATGGCAACAACGTTGCGCAAACTATTAACTGGCGAACTA |
| CTTACTCTAGCTTCCCGGCAACAATTAATAGACTGGATGGAGGCGGATAAAGTTGCAGG |
| ACCACTTCTGCGCTCGGCCCTTCCGGCTGGCTGGTTTATTGCTGATAAATCTGGAGCCGG |
| TGAGCGTGGGTCTCGCGGTATCATTGCAGCACTGGGGCCAGATGGTAAGCCCTCCCGTAT |
| CGTAGTTATCTACACGACGGGGAGTCAGGCAACTATGGATGAACGAAATAGACAGATCG |
| CTGAGATAGGTGCCTCACTGATTAAGCATTGGTAACTGTCAGACCAAGTTTACTCATATA |
| TACTTTAGATTGATTTAAAACTTCATTTTTAATTTAAAAGGATCTAGGTGAAGATCCTTTT |
| TGATAATCTCATGACCAAAATCCCTTAACGTGAGTTTTCGTTCCACTGAGCGTCAGACCC |
| CGTAGAAAAGATCAAAGGATCTTCTTGAGATCCTTTTTTTCTGCGCGTAATCTGCTGCTTG |
| CAAACAAAAAAACCACCGCTACCAGCGGTGGTTTGTTTGCCGGATCAAGAGCTACCAAC |
| TCTTTTTCCGAAGGTAACTGGCTTCAGCAGAGCGCAGATACCAAATACTGTTCTTCTAGT |
| GTAGCCGTAGTTAGGCCACCACTTCAAGAACTCTGTAGCACCGCCTACATACCTCGCTCT |
| GCTAATCCTGTTACCAGTGGCTGCTGCCAGTGGCGATAAGTCGTGTCTTACCGGGTTGGA |
| CTCAAGACGATAGTTACCGGATAAGGCGCAGCGGTCGGGCTGAACGGGGGGTTCGTGCA |
| CACAGCCCAGCTTGGAGCGAACGACCTACACCGAACTGAGATACCTACAGCGTGAGCTA |
| TGAGAAAGCGCCACGCTTCCCGAAGAGAGAAAGGCGGACAGGTATCCGGTAAGCGGCA |
| GGGTCGGAACAGGAGAGCGCACGAGGGAGCTTCCAGGGGGAAACGCCTGGTATCTTTAT |
| AGTCCTGTCGGGTTTCGCCACCTCTGACTTGAGCGTCGATTTTTGTGATGCTCGTCAGGG |
| GGGCGGAGCCTATGGAAAAACGCCAGCAACGCGGCCTTTTTACGGTTCCTGGCCTTTTGC |
| TGGCCTTTTGCTCACATGTTCTTTCCTGCGTTATCCCCTGATTCTGTGGATAACGTATTA |
| CCGCCTTTGAGTGAGCTGATACCGCTCGCCGCAGCCGAACGACCGAGCGCAGCGAGTCA |
| GTGAGCGAGGAAGCGGAAGAGCGCCCAATACGCAAACCGCCTCTCCCCGCGCGTTGGCC |
| GATTCATTAATGCAGCTGGCACGACAGGTTTCCCGACTGGAAAGCGGGCAGTGAGCGCA |
| ACGCAATTAATGTGAGTTAGCTCACTCATTAGGCACCCCAGGCTTTACACTTTATGCTTC |
| CGGCTCGTATGTTGTGTGGAATTGTGAGCGGATAACAATTTCACACAGGAAACAGCTAT |
| GACCATGATTACGCCAAGCTCGAAATTAACCCTCACTAAAGGGAACAAAAGCTGGTACC |
| TCGCGCGACTTGGTTTGCCATTCTTTAGCGCGCGTCGCGTCACACAGCTTGGCCACAATG |
| TGGTTTTTGTCAAACGAAGATTCTATGACGTGTTTAAAGTTTAGGTCGAGTAAAGCGCAA |
| ATCTTTT |

Human eukaryotic translation elongation factor 1 α1 promoter (SEQ ID NO: 13)
GGCTCCGGTGCCCGTCAGTGGGCAGAGCGCACATCGCCCACAGTCCCCGAGAAGTTGGG
GGGAGGGGTCGGCAATTGAACCGGTGCCTAGAGAAGGTGGCGCGGGGTAAACTGGGAA
AGTGATGTCGTGTACTGGCTCCGCCTTTTTCCCGAGGGTGGGGGAGAACCGTATATAAGT
GCAGTAGTCGCCGTGAACGTTCTTTTTCGCAACGGGTTTGCCGCCAGAACAGGTAAGT
GCCGTGTGTGGTTCCCGCGGGCCTGGCCTCTTTACGGGTTATGGCCCTTGCGTGCCTTGA
ATTACTTCCACCTGGCTGCAGTACGTGATTCTTGATCCCGAGCTTCGGGTTGGAAGTGGG
TGGGAGAGTTCGAGGCCTTGCGCTTAAGGAGCCCCTTCGCCTCGTGCTTGAGTTGAGGCC
TGGCCTGGGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTTTTTTTCT
GGCAAGATAGTCTTGTAAATGCGGGCCAAGATCTGCACACTGGTATTTCGGTTTTTGGGG
CCGCGGGCGGCGACGGGGCCCGTGCGTCCCAGCGCACATGTTCGGCGAGGCGGGGCCTG
CGAGCGCGGCCACCGAGAATCGGACGGGGGTAGTCTCAAGCTGGCCGGCCTGCTCTGGT
GCCTGGTCTCGCGCCGCCGTGTATCGCCCCGCCCTGGGCGGCAAGGCTGGCCCGGTCGGC
ACCAGTTGCGTGAGCGGAAAGATGGCCGCTTCCCGGCCCTGCTGCAGGGAGCTCAAAAT

| NUCLEOTIDE SEQUENCES |
|---|
| GGAGGACGCGGCGCTCGGGAGAGCGGGCGGGTGAGTCACCCACACAAAGGAAAAGGGC<br>CTTTCCGTCCTCAGCCGTCGCTTCATGTGACTCCACGGAGTACCGGGCGCCGTCCAGGCA<br>CCTCGATTAGTTCTCGAGCTTTTGGAGTACGTCGTCTTTAGGTTGGGGGGAGGGGTTTTA<br>TGCGATGGAGTTTCCCCACACTGAGTGGGTGGAGACTGAAGTTAGGCCAGCTTGGCACTT<br>GATGTAATTCTCCTTGGAATTTGCCCTTTTTGAGTTTGGATCTTGGTTCATTCTCAAGCCT<br>CAGACAGTGGTTCAAAGTTTTTTTCTTCCATTTCAGGTGTCGTGA | mEya1[NM_001310459.1](SEQ ID NO: 14)
(Length: 1773 bp)
ATGGAAATGCAGGATCTAACCAGCCCGCATAGCCGACTGAGTGGTAGTAGCGAATCCCC
CAGTGGTCCCAAACTCGATAGCTCTCATATAAATAGTACTTCCATGACTCCCAATGGCAC
CGAAGTTAAAACAGAGCCAATGAGCAGCAGTGAAATAGCTTCAACAGCAGCAGACGGG
TCTTTAGACAGTTTCTCAGGTTCAGCTCTCGGAAGCAGCAGCTTTAGTCCAAGACCAGCT
CACCCGTTCTCTCCACCACAGATTTATCCTTCCAAATCATACCCACATATTCTCCCTACCC
CTTCCTCACAAACTATGGCTGCATATGGGCAAACACAGTTTACCACAGGAATGCAACAA
GCCACAGCCTACGCCACGTACCCACAGCCTGGACAGCCCTATGGAATTTCCTCCTATGGT
GCATTGTGGGCAGGCATCAAGACGGAAAGTGGATTGTCCAGTCTCAGTCACCTGGACA
GACGGGATTTCTTAGCTATGGCACAAGCTTTGGTACCCCTCAACCTGGACAGGCACCGTA
CAGCTACCAGATGCAAGTAGCAGCTTTACCACGTCATCAGGATTATATTCAGGAAATA
ATTCACTCACCAACTCCTCCGGATTCAACAGTTCACAGCAGGACTATCCGTCTTATCCCG
GCTTTGGCCAGGGTCAGTACGCACAGTATTATAACAGCTCGCCGTATCCAGCACACTACA
TGACGAGCAGTAACACCAGCCCGACCACACCGTCCACCAATGCCACTTACCAACTCCAG
GAACCACCTTCTGGCGTCACAAGTCAGGCGGTCACAGACCCCACAGCAGAGTACAGTAC
AATCCACAGTCCTTCCACACCCATTAAAGAGACTGACTCCGAGCGGCTGCGTCGAGGTTC
AGATGGGAAGTCACGTGGCCGAGGCAGAAGAAACAATAATCCCTCCCCTCCCCCGGATT
CTGACCTTGAGAGAGTGTTCATCTGGGACCTGGACGAGACCATCATTGTTTTCCACTCCT
TGCTCACGGGGTCCTACGCCAACAGATCGGGAGGGATCCACCTACTTCTGTTTCCCTGG
GACTACGAATGGAAGAGATGATTTTCAACTTGGCAGACACACATCTATTTTTCAATGACC
TAGAAGAGTGTGACCAAGTCCATATAGATGATGTTTCATCAGACGACAACGGCCAGGAC
CTGAGCACATACAACTTTGGAACAGATGGCTTTCCTGCTGCAGCCACCAGTGCTAATTTA
TGCCTGGCAACTGGTGTCCGAGGTGGTGTGGACTGGATGCGAAACTGGCCTTCCGCTAC
AGACGAGTAAAAGAGATCTACAACACCTACAAAAACAACGTGGGAGGTCTGCTTGGCCC
AGCTAAGAGGGAAGCCTGGCTCCAGCTGAGGGCTGAGATTGAGGCACTCACAGACTCCT
GGCTGACCCTGGCCCTGAAGGCCCTCTCCCTCATCCACTCCCGGACGAACTGTGTGAATA
TTTTAGTAACAACTACGCAGCTCATCCCAGCATTGGCAAAAGTCCTGCTATATGGATTAG
GAATTGTGTTTCCAATAGAAAATATTTACAGTGCAACTAAAATAGGAAAGGAAAGCTGT
TTTGAGAGGATAATCCAAAGGTTTGGAAGGAAAGTGGTATACGTTGTCATAGGAGATGG
TGTGGAAGAAGAGCAAGGGGCAAAAAAGCATGCTATGCCCTTCTGGAGGGTCTCCAGTC
ACTCGGACCTCATGGCACTGCATCATGCCTTGGAATTAGAGTACCTG mSix1[NM_009189.3] (SEQ ID NO: 15)
(Length: 855 bp)
ATGTCGATGCTGCCGTCGTTTGGTTTTACGCAAGAGCAAGTGGCGTGCGTGTGCGAAGTT
CTGCAGCAAGGAGGGAACCTGGAACGCCTGGGCAGGTTCTTGTGGTCGTTGCCCGCCTG
CGATCACCTGCACAAGAACGAGAGCGTGCTCAAGGCCAAGGCGGTGGTCGCCTTCCACC
GCGGCAACTTCCGCGAGCTCTACAAGATACTGGAGAGCCACCAGTTCTCGCCTCACAATC
ACCCCAAACTGCAGCAGCTGTGGCTGAAAGCGCACTACGTGGAGGCCGAGAACTTCGC
GGCCGACCCCTGGGTGCCGTGGGCAAATATCGGGTGCGCCGAAAATTCCCGTTGCCGCG
GACCATCTGGGACGGCGAGGAGACCCAGCTACTGCTTTAAGGAGAAGTCTCGGGGCGTGC
TGCGGGAGTGGTACGCGCACAACCCCTACCCCTCACCGAGGGAGAAACGGGAGCTGGCC
GAGGCCACCGGCCTCACCACCACCCAGGTCAGCAACTGGTTTAAGAACCGGAGGCAAAG
AGACCGGGCCGCCGAGGCCAAGGAAAGGGAGAACACCGAAAACAATAACTCCTCCTCC
AACAAGCAGAATCAACTCTCTCCTCTGGAAGGGGGCAAGCCGCTCATGTCCAGCTCAGA
AGAGGAGTTCTCACCCCCCCAAAGTCCAGACCAGAACTCGGTCCTTCTGCTCCAGAGCA
ATATGGGCCACGCCAGGAGCTCAAACTATTCTTCCAGGCCTCACAGCCTCCCAGCCCA
GCCACGGTCTGCAAGCCCATCAGCACCAGCTCCAGGACTCTCTGCTGGGCCCACTCACCT
CCAGTTTGGTGGACTTGGGTTCCTAA msnai2[NM_011415.2](SEQ ID NO: 16)
(Length: 807 bp)
ATGCCGCGCTCCTTCCTGGTCAAGAAACATTTCAACGCCTCCAAGAAGCCCAACTACAGC
GAACTGGACACACACACAGTTATTATTTCCCCATATCTCTATGAAAGTTACCCTATACCT
GTCATACCAAAACCAGAGATCCTCACCTCGGGAGCATACAGCCCTATTACTGTATGGAC
ATCGTCGGCAGCTCCACTCCACTCTCCTTTACCCAGTGGCCTTTCTCCTCTTACTGGATAC
TCCTCATCCTTGGGGCGTGTAAGTCCCCCGCCTTCCTCTGACACTTCATCCAAGGATCAC
AGTGGTTCAGAAAGTCCCATTAGTGACGAAGAGGAGAGACTGCAGCCCAAGCTTTCAGA
CCCCCATGCCATCGAAGCTGAGAAGTTTCAGTGCAATTTATGCAATAAGACCTATTCTAC
GTTCTCTGGGCTGGCCAAACAAGCAGCTGCACTGTGATGCCCAGTCTAGGAAATCGTT
CAGCTGCAAGTACTGTGACAAGGAATATGTGAGCCTGGGTGCCCTGAAGATGCACATTC
GAACCCACACATTGCCTTGTGTCTGCAAGATCTGTGGCAAGGCTTTCTCCAGACCCTGGC
TGCTTCAAGGACACATTAGAACTCACACTGGGGAAAAGCCTTTCTCTTGCCCTCACTGCA
ATAGGGCTTTTGCAGACAGATCAAACCTGAGGGCACATCTGCAGACCCACTCTGATGTA
AAGAAAATACCAGTGCAAAAACTGCTCCAAAACCTTCTCCAGAATGTCGCTTCTGCATAA
ACATGAGGAGTCTGGCTGCTGTGTGGCACAC -continued

NUCLEOTIDE SEQUENCES

Kozak translation initiation sequence (SEQ ID NO: 17)
(Length: 6 bp)
GCCACC

Self-cleaving 2A peptide from foot-and-mouth disease virus (SEQ ID NO: 18)
(Length: 75 bp)
GGAAGCGGAGTGAAACAGACTTTGAATTTTGACCTTCTGAAGTTGGCAGGAGACGTTGA
GTCCAACCCTGGGCCC Self-cleaving 2A peptide from equine rhinitis A virus (SEQ ID NO: 19)
(Length: 69 bp)
GGAAGCGGACAGTGTACTAATTATGCTCTCTTGAAATTGGCTGGAGATGTTGAGAGCAA
CCCAGGTCCC Rabbit beta-globin polyadenylation signal (SEQ ID NO: 20)
(Length: 522 bp)
TCCTCAGGTGCAGGCTGCCTATCAGAAGGTGGTGGCTGGTGTGGCCAATGCCCTGGCTCA
CAAATACCACTGAGATCTTTTTCCCTCTGCCAAAAATTATGGGGACATCATGAAGCCCCT
TGAGCATCTGACTTCTGGCTAATAAAGGAAATTTATTTTCATTGCAATAGTGTGTTGGAA
TTTTTTGTGTCTCTCACTCGGAAGGACATATGGGAGGGCAAATCATTTAAAACATCAGAA
TGAGTATTTGGTTTAGAGTTTGGCAACATATGCCCATATGCTGGCTGCCATGAACAAAGG
TTGGCTATAAAGAGGTCATCAGTATATGAAACAGCCCCTGCTGTCCATTCCTTATTCCA
TAGAAAAGCCTTGACTTGAGGTTAGATTTTTTTTATATTTTGTTTTGTGTTATTTTTTCTT
TAACATCCCTAAAATTTTCCTTACATGTTTTACTAGCCAGATTTTTCCTCCTCTCCTGACT
ACTCCCAGTCATAGCTGTCCCTCTTCTCTTATGGAGATC

REFERENCES

Al-Awqati, Q. and Oliver, J. A. (2002). Stem cells in the kidney. *Kidney Int*, 61, 387-95.

Barak, H., Huh, S. H., Chen, S., Jeanpierre, C., Martinovic, J., Parisot, M., Bole-Feysot, C., Nitschke, P., Salomon, R., Antignac, C., et al. (2012). FGF9 and FGF20 maintain the stemness of nephron progenitors in mice and man. *Dev Cell*, 22, 1191-207.

Barasch, J., Yang, J., Ware, C. B., Taga, T., Yoshida, K., Erdjument-Bromage, H., Tempst, P., Parravicini, E., Malach, S., Aranoff, T., et al. (1999). Mesenchymal to epithelial conversion in rat metanephros is induced by LIF. *Cell*, 99, 377-86.

Bolger, A. M., Lohse, M. and Usadel, B. (2014). Trimmomatic: a flexible trimmer for Illumina sequence data. *Bioinformatics*, 30, 2114-20.

Briggs, J. A., Sun, J., Shepherd, J., Ovchinnikov, D. A., Chung, T. L., Nayler, S. P., Kao, L. P., Morrow, C. A., Thakar, N. Y., Soo, S. Y., et al. (2013). Integration-free induced pluripotent stem cells model genetic and neural developmental features of down syndrome etiology. *Stem Cells*, 31, 467-78.

Brown, A. C., Muthukrishnan, S. D., Guay, J. A., Adams, D. C., Schafer, D. A., Fetting, J. L. and Oxburgh, L. (2013). Role for compartmentalization in nephron progenitor differentiation. *Proc Natl Acad Sci USA*, 110, 4640-5.

Brown, A. C., Muthukrishnan, S. D. and Oxburgh, L. (2015). A synthetic niche for nephron progenitor cells. *Dev Cell*, 34, 229-41.

Buganim, Y., Itskovich, E., Hu, Y. C., Cheng, A. W., Ganz, K., Sarkar, S., Fu, D., Welstead, G. G., Page, D. C. and Jaenisch, R. (2012). Direct reprogramming of fibroblasts into embryonic Sertoli-like cells by defined factors. *Cell Stem Cell*, 11, 373-86.

Chen, R., Amoui, M., Zhang, Z. and Mardon, G. (1997). Dachshund and eyes absent proteins form a complex and function synergistically to induce ectopic eye development in Drosophila. *Cell*, 91, 893-903.

Da Sacco, S., Thornton, M. E., Petrosyan, A., Lavarreda-Pearce, M., Sedrakyan, S., Grubbs, B. H., De Filippo, R. E. and Perin, L. (2016). Direct Isolation and Characterization of Human Nephron Progenitors. *Stem Cells Transl Med*, 6, 419-433.

Davies, J. A., Unbekandt, M., Meson, J., Lusis, M. and Little, M. H. (2012). Dissociation of embryonic kidney followed by re-aggregation as a method for chimeric analysis. *Methods Mol Biol*, 886, 135-46.

Dobin, A., Davis, C. A., Schlesinger, F., Drenkow, J., Zaleski, C., Jha, S., Batut, P., Chaisson, M. and Gingeras, T. R. (2013). STAR: ultrafast universal RNA-seq aligner. *Bioinformatics*, 29, 15-21.

Doherty, J. E., Huye, L. E., Yusa, K., Zhou, L., Craig, N. L. and Wilson, M. H. (2012). Hyperactive piggyBac gene transfer in human cells and in vivo. *Hum Gene Ther*, 23, 311-20.

Edgar, R., Domrachev, M. and Lash, A. E. (2002). Gene Expression Omnibus: NCBI gene expression and hybridization array data repository. *Nucleic Acids Res*, 30, 207-10.

Elick, T. A., Bauser, C. A. and Fraser, M. J. (1996). Excision of the piggyBac transposable element in vitro is a precise event that is enhanced by the expression of its encoded transposase. *Genetica*, 98, 33-41.

Gentleman, R. C., Carey, V. J., Bates, D. M., Bolstad, B., Dettling, M., Dudoit, S., Ellis, B., Gautier, L., Ge, Y., Gentry, J., et al. (2004). Bioconductor: open software development for computational biology and bioinformatics. *Genome Biol*, 5, R80.

Han, D. W., Tapia, N., Hermann, A., Hemmer, K., Hoing, S., Arauzo-Bravo, M. J., Zaehres, H., Wu, G., Frank, S., Moritz, S., et al. (2012). Direct reprogramming of fibroblasts into neural stem cells by defined factors. *Cell Stem Cell*, 10, 465-72.

Harari-Steinberg, O., Metsuyanim, S., Omer, D., Gnatek, Y., Gershon, R., Pri-Chen, S., Ozdemir, D. D., Lerenthal, Y., Noiman, T., Ben-Hur, H., et al. (2013). Identification of human nephron progenitors capable of generation of kidney structures and functional repair of chronic renal disease. *EMBO Mol Med*, 5, 1556-68.

Hartman, H. A., Lai, H. L. and Patterson, L. T. (2007). Cessation of renal morphogenesis in mice. *Dev Biol*, 310, 379-87.

Hendry, C. E. and Little, M. H. (2012). Reprogramming the kidney: a novel approach for regeneration. *Kidney Int*, 82, 138-46.

Hendry, C. E., Vanslambrouck, J. M., Meson, J., Suhaimi, N., Takasato, M., Rae, F. and Little, M. H. (2013). Direct transcriptional reprogramming of adult cells to embryonic nephron progenitors. *J Am Soc Nephrol*, 24, 1424-34.

Huang, P., He, Z., Ji, S., Sun, H., Xiang, D., Liu, C., Hu, Y., Wang, X. and Hui, L. (2011). Induction of functional hepatocyte-like cells from mouse fibroblasts by defined factors. *Nature*, 475, 386-9.

Huangfu, D., Maehr, R., Guo, W., Eijkelenboom, A., Snitow, M., Chen, A. E. and Melton, D. A. (2008). Induction of pluripotent stem cells by defined factors is greatly improved by small-molecule compounds. *Nat Biotechnol*, 26, 795-7.

Ieda, M., Fu, J. D., Delgado-Olguin, P., Vedantham, V., Hayashi, Y., Bruneau, B. G. and Srivastava, D. (2010). Direct reprogramming of fibroblasts into functional cardiomyocytes by defined factors. *Cell*, 142, 375-86.

Imberti, B., Tomasoni, S., Ciampi, O., Pezzotta, A., Derosas, M., Xinaris, C., Rizzo, P., Papadimou, E., Novelli, R., Benigni, A., et al. (2015). Renal progenitors derived from human iPSCs engraft and restore function in a mouse model of acute kidney injury. *Sci Rep*, 5, 8826.

Jha, V., Garcia-Garcia, G., Iseki, K., Li, Z., Naicker, S., Plattner, B., Saran, R., Wang, A. Y. and Yang, C. W. (2013). Chronic kidney disease: global dimension and perspectives. *Lancet*, 382, 260-72.

Jones, S. G., Ito, T. and Phillips, A. O. (2003). Regulation of proximal tubular epithelial cell CD44-mediated binding and internalisation of hyaluronan. *Int J Biochem Cell Biol*, 35, 1361-77.

Kahlig, K. M., Saridey, S. K., Kaja, A., Daniels, M. A., George, A. L., Jr. and Wilson, M. H. (2010). Multiplexed transposon-mediated stable gene transfer in human cells. *Proc Natl Acad Sci USA*, 107, 1343-8.

Kaminski, M. M., Tosic, J., Kresbach, C., Engel, H., Klockenbusch, J., Muller, A. L., Pichler, R., Grahammer, F., Kretz, O., Huber, T. B., et al. (2016). Direct reprogramming of fibroblasts into renal tubular epithelial cells by defined transcription factors. *Nat Cell Biol*, 18, 1269-1280.

Karner, C. M., Das, A., Ma, Z., Self, M., Chen, C., Lum, L., Oliver, G. and Carroll, T. J. (2011). Canonical Wnt9b signaling balances progenitor cell expansion and differentiation during kidney development. *Development*, 138, 1247-57.

Kobayashi, A., Valerius, M. T., Mugford, J. W., Carroll, T. J., Self, M., Oliver, G. and Mcmahon, A. P. (2008). Six2 defines and regulates a multipotent self-renewing nephron progenitor population throughout mammalian kidney development. *Cell Stem Cell*, 3, 169-81.

Lam, A. Q., Freedman, B. S., Morizane, R., Lerou, P. H., Valerius, M. T. and Bonventre, J. V. (2014). Rapid and efficient differentiation of human pluripotent stem cells into intermediate mesoderm that forms tubules expressing kidney proximal tubular markers. *J Am Soc Nephrol*, 25, 1211-25.

Law, C. W., Chen, Y., Shi, W. and Smyth, G. K. (2014). voom: Precision weights unlock linear model analysis tools for RNA-seq read counts. *Genome Biol*, 15, R29.

Li, J., Ariunbold, U., Suhaimi, N., Sunn, N., Guo, J., Mcmahon, J. A., Mcmahon, A. P. and Little, M. (2015). Collecting duct-derived cells display mesenchymal stem cell properties and retain selective in vitro and in vivo epithelial capacity. *J Am Soc Nephrol*, 26, 81-94.

Li, M. A., Turner, D. J., Ning, Z., Yusa, K., Liang, Q., Eckert, S., Rad, L., Fitzgerald, T. W., Craig, N. L. and Bradley, A. (2011). Mobilization of giant piggyBac transposons in the mouse genome. *Nucleic Acids Res*, 39, e148.

Li, X., Oghi, K. A., Zhang, J., Krones, A., Bush, K. T., Glass, C. K., Nigam, S. K., Aggarwal, A. K., Maas, R., Rose, D. W., et al. (2003). Eya protein phosphatase activity regulates Six1-Dach-Eya transcriptional effects in mammalian organogenesis. *Nature*, 426, 247-54.

Li, Z., Araoka, T., Wu, J., Liao, H. K., Li, M., Lazo, M., Zhou, B., Sui, Y., Wu, M. Z., Tamura, I., et al. (2016). 3D Culture Supports Long-Term Expansion of Mouse and Human Nephrogenic Progenitors. *Cell Stem Cell*, 19, 516-529.

Liao, Y., Smyth, G. K. and Shi, W. (2014). featureCounts: an efficient general purpose program for assigning sequence reads to genomic features. *Bioinformatics*, 30, 923-30.

Lusis, M., Li, J., Meson, J., Christensen, M. E., Rice, A. and Little, M. H. (2010). Isolation of clonogenic, long-term self renewing embryonic renal stem cells. *Stem Cell Res*, 5, 23-39.

Marro, S., Pang, Z. P., Yang, N., Tsai, M. C., Qu, K., Chang, H. Y., Sudhof, T. C. and Wernig, M. (2011). Direct lineage conversion of terminally differentiated hepatocytes to functional neurons. *Cell Stem Cell*, 9, 374-82.

Marschner, J. A., Schafer, H., Holderied, A. and Anders, H. J. (2016). Optimizing Mouse Surgery with Online Rectal Temperature Monitoring and Preoperative Heat Supply. Effects on Post-Ischemic Acute Kidney Injury. *PLoS One*, 11, e0149489.

Mcmahon, A. P., Aronow, B. J., Davidson, D. R., Davies, J. A., Gaido, K. W., Grimmond, S., Lessard, J. L., Little, M. H., Potter, S. S., Wilder, E. L., et al. (2008). GUDMAP: the genitourinary developmental molecular anatomy project. *J Am Soc Nephrol*, 19, 667-71.

Morizane, R. and Bonventre, J. V. (2017). Generation of nephron progenitor cells and kidney organoids from human pluripotent stem cells. *Nat Protoc*, 12, 195-207.

Morizane, R., Lam, A. Q., Freedman, B. S., Kishi, S., Valerius, M. T. and Bonventre, J. V. (2015). Nephron organoids derived from human pluripotent stem cells model kidney development and injury. *Nat Biotechnol*, 33, 1193-200.

O'brien, L. L., Guo, Q., Lee, Y., Tran, T., Benazet, J. D., Whitney, P. H., Valouev, A. and Mcmahon, A. P. (2016). Differential regulation of mouse and human nephron progenitors by the Six family of transcriptional regulators. *Development*, 143, 595-608.

Ohto, H., Kamada, S., Tago, K., Tominaga, S. I., Ozaki, H., Sato, S. and Kawakami, K. (1999). Cooperation of six and eya in activation of their target genes through nuclear translocation of Eya. *Mol Cell Biol*, 19, 6815-24.

Oliveira Arcolino, F., Tort Piella, A., Papadimitriou, E., Bussolati, B., Antonie, D. J., Murray, P., Van Den Heuvel, L. and Levtchenko, E. (2015). Human Urine as a Noninvasive Source of Kidney Cells. *Stem Cells Int*, 2015, 362562.

Park, J. S., Ma, W., O'brien, L. L., Chung, E., Guo, J. J., Cheng, J. G., Valerius, M. T., Mcmahon, J. A., Wong, W. H. and Mcmahon, A. P. (2012). Six2 and Wnt regulate self-renewal and commitment of nephron progenitors through shared gene regulatory networks. *Dev Cell*, 23, 637-51.

Pignoni, F., Hu, B., Zavitz, K. H., Xiao, J., Garrity, P. A. and Zipursky, S. L. (1997). The eye-specification proteins So and Eya form a complex and regulate multiple steps in Drosophila eye development. *Cell*, 91, 881-91.

Plisov, S. Y., Yoshino, K., Dove, L. F., Higinbotham, K. G., Rubin, J. S. and Perantoni, A. O. (2001). TGF beta 2, LIF and FGF2 cooperate to induce nephrogenesis. *Development*, 128, 1045-57.

Pode-Shakked, N., Gershon, R., Tam, G., Omer, D., Gnatek, Y., Kanter, I., Oriel, S., Katz, G., Harari-Steinberg, O., Kalisky, T., et al. (2017). Evidence of In Vitro Preservation of Human Nephrogenesis at the Single-Cell Level. *Stem Cell Reports*, 9, 279-291.

Ritchie, M. E., Phipson, B., Wu, D., Hu, Y., Law, C. W., Shi, W. and Smyth, G. K. (2015). limma powers differential expression analyses for RNA-sequencing and microarray studies. *Nucleic Acids Res*, 43, e47.

Robinson, M. D. and Oshlack, A. (2010). A scaling normalization method for differential expression analysis of RNA-seq data. *Genome Biol*, 11, R25.

Rumballe, B. A., Georgas, K. M., Combes, A. N., Ju, A. L., Gilbert, T. and Little, M. H. (2011). Nephron formation adopts a novel spatial topology at cessation of nephrogenesis. *Dev Biol*, 360, 110-22.

Saridey, S. K., Liu, L., Doherty, J. E., Kaja, A., Galvan, D. L., Fletcher, B. S. and Wilson, M. H. (2009). PiggyBac transposon-based inducible gene expression in vivo after somatic cell gene transfer. *Mol Ther*, 17, 2115-20.

Savagner, P., Yamada, K. M. and Thiery, J. P. (1997). The zinc-finger protein slug causes desmosome dissociation, an initial and necessary step for growth factor-induced epithelial-mesenchymal transition. *J Cell Biol*, 137, 1403-19.

Saxen, L. and Sariola, H. (1987). Early organogenesis of the kidney. *Pediatr Nephrol*, 1, 385-92.

Self, M., Lagutin, O. V., Bowling, B., Hendrix, J., Cai, Y., Dressler, G. R. and Oliver, G. (2006). Six2 is required for suppression of nephrogenesis and progenitor renewal in the developing kidney. *EMBO J*, 25, 5214-28.

Taguchi, A., Kaku, Y., Ohmori, T., Sharmin, S., Ogawa, M., Sasaki, H. and Nishinakamura, R. (2014). Redefining the in vivo origin of metanephric nephron progenitors enables generation of complex kidney structures from pluripotent stem cells. *Cell Stem Cell*, 14, 53-67.

Takasato, M., Er, P. X., Becroft, M., Vanslambrouck, J. M., Stanley, E. G., Elefanty, A. G. and Little, M. H. (2014). Directing human embryonic stem cell differentiation towards a renal lineage generates a self-organizing kidney. *Nat Cell Biol*, 16, 118-26.

Takasato, M., Er, P. X., Chiu, H. S. and Little, M. H. (2016). Generation of kidney organoids from human pluripotent stem cells. *Nat Protoc*, 11, 1681-92.

Tanigawa, S., Sharma, N., Hall, M. D., Nishinakamura, R. and Perantoni, A. O. (2015). Preferential Propagation of Competent SIX2+ Nephronic Progenitors by LIF/ROCKi Treatment of the Metanephric Mesenchyme. *Stem Cell Reports*, 5, 435-47.

Tanigawa, S., Taguchi, A., Sharma, N., Perantoni, A. O. and Nishinakamura, R. (2016). Selective In Vitro Propagation of Nephron Progenitors Derived from Embryos and Pluripotent Stem Cells. *Cell Rep*, 15, 801-813.

Walz, A. L., Ooms, A., Gadd, S., Gerhard, D. S., Smith, M. A., Guidry Auvil, J. M., Meerzaman, D., Chen, Q. R., Hsu, C. H., Yan, C., et al. (2015). Recurrent DGCR8, DROSHA, and SIX homeodomain mutations in favorable histology Wilms tumors. *Cancer Cell*, 27, 286-97.

Weber, S., Taylor, J. C., Winyard, P., Baker, K. F., Sullivan-Brown, J., Schild, R., Knuppel, T., Zurowska, A. M., Caldas-Alfonso, A., Litwin, M., et al. (2008). SIX2 and BMP4 mutations associate with anomalous kidney development. *J Am Soc Nephrol*, 19, 891-903.

Wegert, J., Ishaque, N., Vardapour, R., Georg, C., Gu, Z., Bieg, M., Ziegler, B., Bausenwein, S., Nourkami, N., Ludwig, N., et al. (2015). Mutations in the SIX1/2 pathway and the DROSHA/DGCR8 miRNA microprocessor complex underlie high-risk blastemal type Wilms tumors. *Cancer Cell*, 27, 298-311.

Woltjen, K., Michael, I. P., Mohseni, P., Desai, R., Mileikovsky, M., Hamalainen, R., Cowling, R., Wang, W., Liu, P., Gertsenstein, M., et al. (2009). piggyBac transposition reprograms fibroblasts to induced pluripotent stem cells. *Nature*, 458, 766-70.

Woodard, L. E., Cheng, J., Welch, R. C., Williams, F. M., Luo, W., Gewin, L. S. and Wilson, M. H. (2017). Kidney-specific transposon-mediated gene transfer in vivo. *Sci Rep*, 7, 44904.

Woodard, L. E., Li, X., Malani, N., Kaja, A., Hice, R. H., Atkinson, P. W., Bushman, F. D., Craig, N. L. and Wilson, M. H. (2012). Comparative analysis of the recently discovered hAT transposon TcBuster in human cells. *PLoS One*, 7, e42666.

Woodard, L. E. and Wilson, M. H. (2015). piggyBac-ing models and new therapeutic strategies. *Trends Biotechnol*, 33, 525-33.

Xu, J. and Xu, P. X. (2015). Eya-six are necessary for survival of nephrogenic cord progenitors and inducing nephric duct development before ureteric bud formation. *Dev Dyn*, 244, 866-73.

Xu, P. X., Zheng, W., Huang, L., Maire, P., Laclef, C. and Silvius, D. (2003). Six1 is required for the early organogenesis of mammalian kidney. *Development*, 130, 3085-94.

Yusa, K., Zhou, L., Li, M. A., Bradley, A. and Craig, N. L. (2011). A hyperactive piggyBac transposase for mammalian applications. *Proc Natl Acad Sci USA*, 108, 1531-6.

Zhou, T., Benda, C., Dunzinger, S., Huang, Y., Ho, J. C., Yang, J., Wang, Y., Zhang, Y., Zhuang, Q., Li, Y., et al. (2012). Generation of human induced pluripotent stem cells from urine samples. *Nat Protoc*, 7, 2080-9.

The invention claimed is:

1. An isolated mammalian cell having an ability to differentiate into nephron segments, said isolated cell comprising at least one exogenous nucleic acid that comprises a nucleotide sequence of a SNAI2 gene, an EYA1 gene and a SIX1 gene, or respective fragments thereof, that are expressed at a level that induces said isolated cell to have the ability to differentiate into nephron segments, wherein said isolated cell does not comprise an exogenous nucleic acid comprising a SIX2 gene, a HOXA11 gene, or an OSR1 gene.

2. The isolated cell of claim 1 which does not normally have the ability to differentiate into nephron segments.

3. The isolated cell of claim 1, which is a human cell.

* * * * *

UNITED STATES PATENT AND TRADEMARK OFFICE
CERTIFICATE OF CORRECTION

| | |
|---|---|
| PATENT NO. | : 11,492,644 B2 |
| APPLICATION NO. | : 16/616229 |
| DATED | : November 8, 2022 |
| INVENTOR(S) | : Melissa Little et al. |

It is certified that error appears in the above-identified patent and that said Letters Patent is hereby corrected as shown below:

In the Specification

In Column 1, Line 12, before the "BACKGROUND" section, please insert the following new paragraph:
--STATEMENT OF GOVERNMENT SUPPORT
This invention was made with government support under Grant Nos. DK093660, DK107344, and DK060445, awarded by the National Institutes of Health. The government has certain rights in the invention.--

Signed and Sealed this
Twenty-fifth Day of July, 2023

Katherine Kelly Vidal
*Director of the United States Patent and Trademark Office*

SEQUENCE LISTING

```
<160> NUMBER OF SEQ ID NOS: 40

<210> SEQ ID NO 1
<211> LENGTH: 807
<212> TYPE: DNA
<213> ORGANISM: Artificial Sequence
<220> FEATURE:
```

<223> OTHER INFORMATION: Synthetic construct

<400> SEQUENCE: 1

```
atgccgcgct ccttcctggt caagaagcat ttcaacgcct ccaaaaagcc aaactacagc    60
gaactggaca cacatacagt gattatttcc ccgtatctct atgagagtta ctccatgcct   120
gtcataccac aaccagagat cctcagctca ggagcataca gccccatcac tgtgtggact   180
accgctgctc cattccacgc ccagctaccc aatggcctct ctcctctttc cggatactcc   240
tcatctttgg ggcgagtgag tcccccctcct ccatctgaca cctcctccaa ggaccacagt   300
ggctcagaaa gccccattag tgatgaagag gaaagactac agtccaagct ttcagacccc   360
catgccattg aagctgaaaa gtttcagtgc aatttatgca ataagaccta ttcaactttt   420
tctgggctgg ccaaacataa gcagctgcac tgcgatgccc agtctagaaa atctttcagc   480
tgtaaatact gtgacaagga atatgtgagc ctgggcgccc tgaagatgca tattcggacc   540
cacacattac cttgtgtttg caagatctgc ggcaaggcgt tttccagacc ctggttgctt   600
caaggacaca ttagaactca cacggggggag aagccttttt cttgccctca ctgcaacaga   660
gcatttgcag acaggtcaaa tctgagggct catctgcaga cccattctga tgtaaagaaa   720
taccagtgca aaaactgctc caaaaccttc tccagaatgt ctctcctgca caaacatgag   780
gaatctggct gctgtgtagc acactga                                       807
```

<210> SEQ ID NO 2
<211> LENGTH: 855
<212> TYPE: DNA
<213> ORGANISM: Artificial Sequence
<220> FEATURE:
<223> OTHER INFORMATION: Synthetic construct

<400> SEQUENCE: 2

```
atgtcgatgc tgccgtcgtt tggctttacg caggagcaag tggcgtgcgt gtgcgaggtt    60
ctgcagcaag gcggaaacct ggagcgcctg ggcaggttcc tgtggtcact gccgccctgc   120
gaccacctgc acaagaacga gagcgtactc aaggccaagg cggtggtcgc cttccaccgc   180
ggcaacttcc gtgagctcta caagatcctg gagagccacc agttctcgcc tcacaaccac   240
cccaaactgc agcaactgtg gctgaaggcg cattacgtgg aggccgagaa gctgcgcggc   300
cgaccccctgg gcgccgtggg caaatatcgg gtgcgccgaa aatttccact gccgcgcacc   360
atctgggacg gcgaggagac cagctactgc ttcaaggaga agtcgagggg tgtcctgcgg   420
gagtggtacg cgcacaatcc ctacccatcg ccgcgtgaga agcgggagct ggccgaggcc   480
accggcctca ccaccaccca ggtcagcaac tggtttaaga accggaggca aagagaccgg   540
gccgcggagg ccaaggaaag ggagaacacc gaaaacaata actcctcctc caacaagcag   600
aaccaactct ctcctctgga aggggcaag ccgctcatgt ccagctcaga agaggaattc   660
tcacctcccc aaagtccaga ccagaactcg gtccttctgc tgcagggcaa tatgggccac   720
gccaggagct caaactattc tctcccgggc ttaacagcct cgcagcccag tcacggcctg   780
cagacccacc agcatcagct ccaagactct ctgctcggcc cctcacctc cagtctggtg   840
gacttggggt cctaa                                                    855
```

<210> SEQ ID NO 3
<211> LENGTH: 1779
<212> TYPE: DNA
<213> ORGANISM: Artificial Sequence
<220> FEATURE:
<223> OTHER INFORMATION: Synthetic construct

<400> SEQUENCE: 3

```
atggaaatgc aggatctaac cagcccgcat agccgtctga gtggtagtag tgaatccccc      60
agtggcccca aactcggtaa ctctcatata aatagtaatt ccatgactcc caatggcacc     120
gaagttaaaa cagagccaat gagcagcagt gaaacagctt caacgacagc cgacgggtct     180
ttaaacaatt tctcaggttc agcaattggg agcagtagtt tcagcccacg accaactcac     240
cagttctctc caccacagat ttacccttcc aacagaccat acccacatat tctccctacc     300
ccttcctcac aaactatggc tgcatatggg caaacacagt ttaccacagg aatgcaacaa     360
gctacagcct atgccacgta cccacagcca ggacagccgt acggcatttc ctcatatggt     420
gcattgtggg caggcatcaa gactgaaggt ggattgtcac agtctcagtc acctggacag     480
acaggatttc tcagctatgg cacaagcttc agtacccctc aacctggaca ggcaccatac     540
agctaccaga tgcaaggtag cagttttaca acatcatcag gaatatatac aggaaataat     600
tcactcacaa attcctctgg atttaatagt tcacagcagg actatccgtc ttatcccagt     660
tttggccagg gtcagtacgc acagtattat aacagctcac cgtatccagc acattatatg     720
accagcagca acaccagccc aacgacacca tccaccaatg ccacttacca gcttcaagaa     780
ccgccatctg gcatcaccag ccaagcagtt acagatccca cagcagagta cagcacaatc     840
cacagcccat caacacccat taaagattca gattctgatc gattgcgtcg aggttcagat     900
gggaaatcac gtggacgggg ccgaagaaac aataatcctt cacctccccc agattctgat     960
cttgagagag tgttcatctg ggacttggat gagacaatca ttgttttcca ctccttgctt    1020
actgggtcct acgccaacag atatgggagg gatccaccca cttcagtttc ccttggactg    1080
cgaatggaag aaatgatttt caacttggca gacacacatt tattttttaa tgacttagaa    1140
gaatgtgacc aagtccatat agatgatgtt tcttcagatg ataacggaca ggacctaagc    1200
acatataact ttggaacaga tggctttcct gctgcagcaa ccagtgctaa cttatgtttg    1260
gcaactggtg tacggggcgg tgtggactgg atgagaaagt tggccttccg ctacagacgg    1320
gtaaaagaga tctacaacac ctacaaaaat aatgttggag gtctgcttgg tccagctaag    1380
agggaagcct ggctgcagtt gagggccgaa attgaagccc tgaccgactc ctggttgaca    1440
ctggccctga aagcactctc gctcattcac tcccggacaa actgtgtgaa tattttagta    1500
acaactactc agctcatccc agcattggcg aaagtcctgc tgtatgggtt aggaattgta    1560
tttccaatag aaaatattta cagtgcaact aaaataggaa aagaaagctg ttttgagaga    1620
ataattcaaa ggtttggaag aaaagtggtg tatgttgtta taggagatgg tgtagaagaa    1680
gaacaaggag caaaaaagca cgcgatgccc ttctggagga tctccagcca ctcggacctc    1740
atggccctgc accatgcctt ggaactggag tacctgtaa                           1779
```

<210> SEQ ID NO 4
<211> LENGTH: 236
<212> TYPE: DNA
<213> ORGANISM: Artificial Sequence
<220> FEATURE:
<223> OTHER INFORMATION: Synthetic construct

<400> SEQUENCE: 4

```
ttaaccctag aaagataatc atattgtgac gtacgttaaa gataatcatg cgtaaaattg      60
acgcatgtgt tttatcggtc tgtatatcga ggtttattta ttaatttgaa tagatattaa     120
gttttattat atttacactt acatactaat aataaattca acaaacaatt tatttatgtt     180
```
tatttattta ttaaaaaaaa acaaaaactc aaaatttctt ctataaagta acaaaa 236

<210> SEQ ID NO 5
<211> LENGTH: 311
<212> TYPE: DNA
<213> ORGANISM: Artificial Sequence
<220> FEATURE:
<223> OTHER INFORMATION: Synthetic construct

<400> SEQUENCE: 5
ttaaccctag aaagatagtc tgcgtaaaat tgacgcatgc attcttgaaa tattgctctc     60
tctttctaaa tagcgcgaat ccgtcgctgt gcatttagga catctcagtc gccgcttgga    120
gctcccgtga ggcgtgcttg tcaatgcggt aagtgtcact gattttgaac tataacgacc    180
gcgtgagtca aaatgacgca tgattatctt ttacgtgact tttaagattt aactcatacg    240
ataattatat tgttatttca tgttctactt acgtgataac ttattatata tatattttct    300
tgttatagat a                                                         311

<210> SEQ ID NO 6
<211> LENGTH: 316
<212> TYPE: DNA
<213> ORGANISM: Artificial Sequence
<220> FEATURE:
<223> OTHER INFORMATION: Synthetic construct

<400> SEQUENCE: 6
cgagtttact ccctatcagt gatagagaac gtatgtcgag tttactccct atcagtgata     60
gagaacgatg tcgagtttac tccctatcag tgatagagaa cgtatgtcga gtttactccc    120
tatcagtgat agagaacgta tgtcgagttt actccctatc agtgatagag aacgtatgtc    180
gagtttatcc ctatcagtga tagagaacgt atgtcgagtt tactccctat cagtgataga    240
gaacgtatgt cgaggtaggc gtgtacggtg ggaggcctat ataagcagag ctcgtttagt    300
gaaccgtcag atcgcc                                                    316

<210> SEQ ID NO 7
<211> LENGTH: 711
<212> TYPE: DNA
<213> ORGANISM: Artificial Sequence
<220> FEATURE:
<223> OTHER INFORMATION: Synthetic construct

<400> SEQUENCE: 7
atggtgagca agggcgagga ggataacatg gccatcatca aggagttcat gcgcttcaag     60
gtgcacatgg agggctccgt gaacggccac gagttcgaga tcgagggcga gggcgagggc    120
cgccectacg agggcaccca gaccgccaag ctgaaggtga ccaagggtgg ccccctgccc    180
ttcgcctggg acatcctgtc ccctcagttc atgtacggct ccaaggccta cgtgaagcac    240
cccgccgaca tccccgacta cttgaagctg tccttcccceg agggcttcaa gtgggagcgc    300
gtgatgaact tcgaggacgg cggcgtggtg accgtgaccce aggactcctc cctgcaggac    360
ggcgagttca tctacaaggt gaagctgcgc ggcaccaact cccctccga cggccccgta    420
atgcagaaga gaccatggg ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg gccgccactc caccggcggc atggacgagc tgtacaagta a              711

<210> SEQ ID NO 8
<211> LENGTH: 174
<212> TYPE: DNA
<213> ORGANISM: Artificial Sequence
<220> FEATURE:
<223> OTHER INFORMATION: Synthetic construct

<400> SEQUENCE: 8
taccacattt gtagaggttt tacttgcttt aaaaaacctc ccacacctcc ccctgaacct    60
gaaacataaa atgaatgcaa ttgttgttgt taacttgttt attgcagctt ataatggtta   120
caaataaagc aatagcatca caaatttcac aaataaagca ttttttttcac tgcc         174

<210> SEQ ID NO 9
<211> LENGTH: 57
<212> TYPE: DNA
<213> ORGANISM: Artificial Sequence
<220> FEATURE:
<223> OTHER INFORMATION: Synthetic construct

<400> SEQUENCE: 9
gccacgaact tctctctgtt aaagcaagca ggagacgtgg aagaaaaccc cggtccc       57

<210> SEQ ID NO 10
<211> LENGTH: 66
<212> TYPE: DNA
<213> ORGANISM: Artificial Sequence
<220> FEATURE:
<223> OTHER INFORMATION: Synthetic construct

<400> SEQUENCE: 10
gtgaaacaga ctttgaattt tgaccttctc aagttggcgg gagacgtgga gtccaaccca    60
gggccc                                                               66

<210> SEQ ID NO 11
<211> LENGTH: 60
<212> TYPE: DNA
<213> ORGANISM: Artificial Sequence
<220> FEATURE:
<223> OTHER INFORMATION: Synthetic construct

<400> SEQUENCE: 11
caatgtacta actacgcttt gttgaaactc gctggcgatg ttgaaagtaa ccccggtcct    60

<210> SEQ ID NO 12
<211> LENGTH: 9153
<212> TYPE: DNA
<213> ORGANISM: Artificial Sequence
<220> FEATURE:
<223> OTHER INFORMATION: Synthetic construct

<400> SEQUENCE: 12
ttaaccctag aaagatagtc tgcgtaaaat tgacgcatgc attcttgaaa tattgctctc    60
tctttctaaa tagcgcgaat ccgtcgctgt gcatttagga catctcagtc gccgcttgga   120
gctcccgtga ggcgtgcttg tcaatgcggt aagtgtcact gattttgaac tataacgacc   180
gcgtgagtca aaatgacgca tgattatctt ttacgtgact tttaagattt aactcatacg   240
ataattatat tgttatttca tgttctactt acgtgataac ttattatata tatttttct    300 tgttatagat atcatcaact tgtatagaa aagttgggct ccggtgcccg tcagtgggca    360
gagcgcacat cgcccacagt ccccgagaag ttgggggag gggtcggcaa ttgaaccggt   420

```
gcctagagaa ggtggcgcgg ggtaaactgg gaaagtgatg tcgtgtactg gctccgcctt      480
tttcccgagg gtgggggaga accgtatata agtgcagtag tcgccgtgaa cgttctttt       540 cgcaacgggt tgccgccag aacacaggta agtgccgtgt gtggttcccg cgggcctggc       600
ctctttacgg gttatggccc ttgcgtgcct tgaattactt ccacctggct gcagtacgtg      660
attcttgatc ccgagcttcg ggttggaagt gggtgggaga gttcgaggcc ttgcgcttaa      720 ggagccccctt cgcctcgtgc ttgagttgag gcctggcctg ggcgctgggg ccgccgcgtg     780
cgaatctggt ggcaccttcg cgcctgtctc gctgctttcg ataagtctct agccatttaa     840 aattttttgat gacctgctgc gacgcttttt ttctggcaag atagtcttgt aaatgcgggc    900
caagatctgc acactggtat ttcggttttt ggggccgcgg gcggcgacgg ggcccgtgcg    960
tcccagcgca catgttcggc gaggcggggc ctgcgagcgc ggccaccgag aatcggacgg    1020
gggtagtctc aagctggccg gcctgctctg gtgcctggtc tcgcgccgcc gtgtatcgcc    1080
ccgccctggg cggcaaggct ggcccggtcg gcaccagttg cgtgagcgga aagatggccg    1140
cttcccggcc ctgctgcagg gagctcaaaa tggaggacgc ggcgctcggg agagcgggcg    1200
ggtgagtcac ccacacaaag gaaaagggcc tttccgtcct cagccgtcgc ttcatgtgac    1260 tccacgagt accgggcgcc gtccaggcac ctcgattagt tctcgagctt ttggagtacg     1320
tcgtctttag gttgggggga ggggttttat gcgatggagt ttccccacac tgagtgggtg    1380
gagactgaag ttaggccagc ttggcacttg atgtaattct ccttggaatt tgccctttt     1440 gagtttggat cttggttcat tctcaagcct cagacagtgg ttcaaagttt ttttcttcca    1500
tttcaggtgt cgtgacaagt ttgtacaaaa agcaggctg ccaccatgcc gcgctccttc     1560
ctggtcaaga aacatttcaa cgcctccaag aagcccaact acagcgaact ggacacacac    1620
acagttatta tttcccccata tctctatgaa agttaccca tacctgtcat accaaaacca    1680
gagatcctca cctcgggagc atacagccct attactgtat ggacatcgtc ggcagctcca    1740
ctccactctc ctttacccag tggcctttct cctcttactg gatactcctc atccttgggg    1800
cgtgtaagtc ccccgccttc ctctgacact tcatccaagg atcacagtgg ttcagaaagt    1860
cccattagtg acgaagagga gagactgcag cccaagcttt cagacccca tgccatcgaa     1920 gctgagaagt ttcagtgcaa tttatgcaat aagaccatt ctacgttctc tgggctggcc     1980
aaacacaagc agctgcactg tgatgccag tctaggaaat cgttcagctg caagtactgt    2040
gacaaggaat atgtgagcct gggtgccctg aagatgcaca ttcgaaccca cattgcct     2100 tgtgtctgca agatcgtgtg caaggctttc tccagaccct ggctgcttca aggacacatt    2160
agaactcaca ctggggaaaa gcctttctct tgccctcact gcaatagggc ttttgcagac    2220
agatcaaacc tgagggcaca tctgcagacc cactctgatg taaagaaata ccagtgcaaa    2280
aactgctcca aaaccttctc cagaatgtcg cttctgcata acatgagga gtctggctgc    2340 tgtgtggcac acggaagcgg agtgaaacag actttgaatt ttgaccttct gaagttggca    2400
ggagacgttg agtccaaccc tgggcccatg gaaatgcaga atctaaccag cccgcatagc    2460
cgactgagtg gtagtagcga atcccccagt ggtcccaaac tcgatagctc tcatataaat    2520
agtacttcca tgactcccaa tggcaccgaa gttaaaacag agcaatgag cagcagtgaa    2580 atagcttcaa cagcagcaga cgggtcttta gacagtttct caggttcagc tctcggaagc    2640
agcagcttta gtccaagacc agctcaccccg ttctctccac cacagattta tccttccaaa   2700 tcataccac atattctccc tacccccttcc tcacaaaacta tggctgcata tgggcaaaca    2760
cagtttacca caggaatgca acaagccaca gcctacgcca cgtacccaca gcctggacag    2820
```

| | |
|---|---|
| ccctatggaa tttcctccta tggtgcattg tgggcaggca tcaagacgga aagtggattg | 2880 |
| tcacagtctc agtcacctgg acagacggga tttcttagct atggcacaag ctttggtacc | 2940 |
| cctcaacctg gacaggcacc gtacagctac cagatgcaag gtagcagctt taccacgtca | 3000 |
| tcaggattat attcaggaaa taattcactc accaactcct ccggattcaa cagttcacag | 3060 |
| caggactatc cgtcttatcc cggctttggc cagggtcagt acgcacagta ttataacagc | 3120 |
| tcgccgtatc cagcacacta catgacgagc agtaacacca gcccgaccac accgtccacc | 3180 |
| aatgccactt accaactcca ggaaccacct tctggcgtca caagtcaggc ggtcacagac | 3240 |
| cccacagcag agtacagtac aatccacagt ccttccacac ccattaaaga gactgactcc | 3300 |
| gagcggctgc gtcgaggttc agatgggaag tcacgtggcc gaggcagaag aaacaataat | 3360 |
| ccctcccctc ccccggattc tgaccttgag agagtgttca tctgggacct ggacgagacc | 3420 |
| atcattgttt tccactcctt gctcacgggg tcctacgcca acagatacgg gagggatcca | 3480 |
| cctacttctg tttccctggg actacgaatg gaagagatga ttttcaactt ggcagacaca | 3540 |
| catctatttt tcaatgacct agaagagtgt gaccaagtcc atatagatga tgtttcatca | 3600 |
| gacgacaacg gccaggacct gagcacatac aactttggaa cagatggctt tcctgctgca | 3660 |
| gccaccagtg ctaatttatg cctggcaact ggtgtccgag gtggtgtgga ctggatgcgg | 3720 |
| aaactggcct tccgctacag acgagtaaaa gagatctaca cacctacaa aaacaacgtg | 3780 |
| ggaggtctgc ttggcccagc taagagggaa gcctggctcc agctgagggc tgagattgag | 3840 |
| gcactcacag actcctggct gaccctggcc ctgaaggccc tctccctcat ccactcccgg | 3900 |
| acgaactgtg tgaatatttt agtaacaact acgcagctca tcccagcatt ggcaaaagtc | 3960 |
| ctgctatatg gattaggaat tgtgtttcca atagaaaata tttacagtgc aactaaaata | 4020 |
| ggaaaggaaa gctgttttga gaggataatc caaaggtttg aaggaaagt ggtatacgtt | 4080 |
| gtcataggag atggtgtgga agaagagcaa ggggcaaaaa agcatgctat gcccttctgg | 4140 |
| agggtctcca gtcactcgga cctcatggca ctgcatcatg ccttggaatt agagtacctg | 4200 |
| ggaagcggac agtgtactaa ttatgctctc ttgaaattgg ctggagatgt tgagagcaac | 4260 |
| ccaggtccca tgtcgatgct gccgtcgttt ggttttacgc aagagcaagt ggcgtgcgtg | 4320 |
| tgcgaagttc tgcagcaagg agggaacctg gaacgcctgg gcaggttctt gtggtcgttg | 4380 |
| cccgcctgcg atcacctgca caagaacgag agcgtgctca aggccaaggc ggtggtcgcc | 4440 |
| ttccaccgcg gcaacttccg cgagctctac aagatactgg agagccacca gttctcgcct | 4500 |
| cacaatcacc ccaaactgca gcagctgtgg ctgaaagcgc actacgtgga ggccgagaaa | 4560 |
| cttcgcggcc gaccctgggt gccgtgggc aaatatcggg tgcgccgaaa attcccgttg | 4620 |
| ccgcggacca tctgggacgg cgaggagacc agctactgct ttaaggagaa gtctcggggc | 4680 |
| gtgctgcggg agtggtacgc gcacaacccc taccctcac cgagggagaa acgggagctg | 4740 |
| gccgaggcca ccgcctcac caccacccag gtcagcaact ggtttaagaa ccggaggcaa | 4800 |
| agagaccggg ccgccgaggc caaggaaagg gagaacaccg aaaacaataa ctcctcctcc | 4860 |
| aacaagcaga atcaactctc tcctctggaa ggggcaagc cgctcatgtc cagctcagaa | 4920 |
| gaggagttct cacccccca agtccagac cagaactcgg tccttctgct ccagagcaat | 4980 |
| atgggccacg ccaggagctc aaactattct cttccaggcc tcacagcctc ccagcccagc | 5040 |
| cacggtctgc aagcccatca gcaccagctc caggactctc tgctgggccc actcacctcc | 5100 |
| agtttggtgg acttgggttc ctaaacccag cttcttgta caaagtggtg atcctcaggt | 5160 |

```
gcaggctgcc tatcagaagg tggtggctgg tgtggccaat gccctggctc acaaatacca    5220
ctgagatctt ttttccctctg ccaaaaatta tggggacatc atgaagcccc ttgagcatct    5280
gacttctggc taataaagga aatttatttt cattgcaata gtgtgttgga attttttgtg    5340
tctctcactc ggaaggacat atgggagggc aaatcattta aaacatcaga atgagtattt    5400
ggtttagagt ttggcaacat atgcccatat gctggctgcc atgaacaaag gttggctata    5460
aagaggtcat cagtatatga aacagccccc tgctgtccat tccttattcc atagaaaagc    5520
cttgacttga ggttagattt ttttttatatt ttgttttgtg ttattttttt ctttaacatc    5580
cctaaaattt tccttacatg ttttactagc cagattttc ctcctctcct gactactccc     5640
agtcatagct gtccctcttc tcttatggag atccctcgac ctgcagccca gcttggatc     5700
cctcgagtta attaacgaga gcataatatt gatatgtgcc aaagttgttt ctgactgact    5760
aataagtata atttgtttct attatgtata ggttaagcta attacttatt ttataataca    5820
acatgactgt ttttaaagta caaaataagt ttattttttgt aaaagagaga atgtttaaaa    5880
gttttgttac tttatagaag aaattttgag ttttttgtttt tttttaataa ataaataaac    5940
ataaataaat tgtttgttga atttattatt agtatgtaag tgtaaatata ataaaactta    6000
atatctattc aaattaataa ataaacctcg atatacagac cgataaaaca catgcgtcaa    6060
ttttacgcat gattatcttt aacgtacgtc acaatatgat tatctttcta gggttaaata    6120
atagtttcta atttttttat tattcagcct gctgtcgtga ataccgagct ccaattcgcc    6180
ctatagtgag tcgtattaca attcactggc cgtcgtttta caacgtcgtg actgggaaaa    6240
ccctggcgtt acccaactta atcgccttgc agcacatccc ctttcgcca gctggcgtaa     6300
tagcgaagag gcccgcaccg atcgcccttc ccaacagttg cgcagcctga atggcgaatg    6360
ggacgcgccc tgtagcggcg cattaagcgc ggcgggtgtg tggttacgc gcagcgtgac     6420
cgctacactt gccagcgccc tagcgcccgc tcctttcgct ttcttccctt cctttctcgc    6480
cacgttcgcc ggctttcccc gtcaagctct aaatcggggg ctcccttag ggttccgatt     6540
tagtgcttta cggcacctcg accccaaaaa acttgattag ggtgatggtt cacgtagtgg    6600
gccatcgccc tgatagacgg tttttcgccc tttgacgttg gagtccacgt tctttaatag    6660
tggactcttg ttccaaactg gaacaacact caaccctatc tcggtctatt cttttgattt    6720
ataagggatt ttgccgattt cggcctattg gttaaaaaat gagctgattt aacaaaaatt    6780
taacgcgaat tttaacaaaa tattaacgct tacaatttag gtggcacttt tcggggaaat    6840
gtgcgcggaa cccctatttg tttatttttc taaatacatt caaatatgta tccgctcatg    6900
agacaataac cctgataaat gcttcaataa tattgaaaaa ggaagagtat gagtattcaa    6960
catttccgtg tcgcccttat tcccttttt gcggcatttt gccttcctgt ttttgctcac    7020
ccagaaacgc tggtgaaagt aaaagatgct gaagatcagt tgggtgcacg agtgggttac    7080
atcgaactgg atctcaacag cggtaagatc cttgagagtt ttcgccccga agaacgtttt    7140
ccaatgatga gcactttaa agttctgcta tgtggcgcgg tattatcccg tattgacgcc    7200
gggcaagagc aactcggtcg ccgcatacac tattctcaga atgacttggt tgagtactca    7260
ccagtcacag aaaagcatct tacgatggc atgacagtaa gagaattatg cagtgctgcc    7320
ataaccatga gtgataacac tgcggccaac ttacttctga caacgatcgg aggaccgaag    7380
gagctaaccg cttttttgca caacatgggg gatcatgtaa ctcgccttga tcgttgggaa    7440
ccggagctga atgaagccat accaaacgac gagcgtgaca ccacgatgcc tgtagcaatg    7500
gcaacaacgt tgcgcaaact attaactggc gaactactta ctctagcttc ccggcaacaa    7560
```

| | | |
|---|---|---|
| ttaatagact ggatggaggc ggataaagtt gcaggaccac ttctgcgctc ggcccttccg | 7620 |
| gctggctggt ttattgctga taaatctgga gccggtgagc gtgggtctcg cggtatcatt | 7680 |
| gcagcactgg ggccagatgg taagccctcc cgtatcgtag ttatctacac gacggggagt | 7740 |
| caggcaacta tggatgaacg aaatagacag atcgctgaga taggtgcctc actgattaag | 7800 |
| cattggtaac tgtcagacca agtttactca tatatacttt agattgattt aaaacttcat | 7860 |
| ttttaattta aaaggatcta ggtgaagatc cttttgata atctcatgac caaatccct | 7920 |
| taacgtgagt tttcgttcca ctgagcgtca gaccccgtag aaaagatcaa aggatcttct | 7980 |
| tgagatcctt ttttctgcg cgtaatctgc tgcttgcaaa caaaaaaacc accgctacca | 8040 |
| gcggtggttt gtttgccgga tcaagagcta ccaactcttt ttccgaaggt aactggcttc | 8100 |
| agcagagcgc agataccaaa tactgttctt ctagtgtagc cgtagttagg ccaccacttc | 8160 |
| aagaactctg tagcaccgcc tacatacctc gctctgctaa tcctgttacc agtggctgct | 8220 |
| gccagtggcg ataagtcgtg tcttaccggg ttggactcaa gacgatagtt accggataag | 8280 |
| gcgcagcggt cgggctgaac ggggggttcg tgcacacagc ccagcttgga gcgaacgacc | 8340 |
| tacaccgaac tgagatacct acagcgtgag ctatgagaaa gcgccacgct tcccgaagag | 8400 |
| agaaaggcgg acaggtatcc ggtaagcggc agggtcggaa caggagagcg cacgagggag | 8460 |
| cttccagggg gaaacgcctg gtatctttat agtcctgtcg ggtttcgcca cctctgactt | 8520 |
| gagcgtcgat ttttgtgatg ctcgtcaggg gggcggagcc tatggaaaaa cgccagcaac | 8580 |
| gcggcctttt tacggttcct ggccttttgc tggccttttg ctcacatgtt ctttcctgcg | 8640 |
| ttatcccctg attctgtgga taaccgtatt accgcctttg agtgagctga taccgctcgc | 8700 |
| cgcagccgaa cgaccgagcg cagcgagtca gtgagcgagg aagcggaaga gcgcccaata | 8760 |
| cgcaaaccgc ctctccccgc gcgttggccg attcattaat gcagctggca cgacaggttt | 8820 |
| cccgactgga aagcgggcag tgagcgcaac gcaattaatg tgagttagct cactcattag | 8880 |
| gcaccccagg ctttacactt tatgcttccg gctcgtatgt tgtgtggaat tgtgagcgga | 8940 |
| taacaatttc acacaggaaa cagctatgac catgattacg ccaagctcga aattaaccct | 9000 |
| cactaaaggg aacaaaagct ggtacctcgc gcgacttggt ttgccattct ttagcgcgcg | 9060 |
| tcgcgtcaca cagcttggcc acaatgtggt ttttgtcaaa cgaagattct atgacgtgtt | 9120 |
| taaagtttag gtcgagtaaa gcgcaaatct ttt | 9153 |

<210> SEQ ID NO 13
<211> LENGTH: 1179
<212> TYPE: DNA
<213> ORGANISM: Artificial Sequence
<220> FEATURE:
<223> OTHER INFORMATION: Synthetic construct

<400> SEQUENCE: 13

| | | |
|---|---|---|
| ggctccggtg cccgtcagtg ggcagagcgc acatcgccca cagtccccga gaagttgggg | 60 |
| ggaggggtcg gcaattgaac cggtgcctag agaaggtggc gcggggtaaa ctgggaaagt | 120 |
| gatgtcgtgt actggctccg ccttttttccc gagggtgggg gagaaccgta tataagtgca | 180 |
| gtagtcgccg tgaacgttct ttttcgcaac gggtttgccg ccagaacaca ggtaagtgcc | 240 |
| gtgtgtggtt cccgcgggcc tggcctcttt acgggttatg gcccttgcgt gccttgaatt | 300 |
| acttccacct ggctgcagta cgtgattctt gatcccgagc ttcggggtgg aagtgggtgg | 360 |
| gagagttcga ggccttgcgc ttaaggagcc ccttcgcctc gtgcttgagt tgaggcctgg | 420 |

-continued

| | |
|---|---|
| cctgggcgct ggggccgccg cgtgcgaatc tggtggcacc ttcgcgcctg tctcgctgct | 480 |
| ttcgataagt ctctagccat ttaaaatttt tgatgacctg ctgcgacgct ttttttctgg | 540 |
| caagatagtc ttgtaaatgc gggccaagat ctgcacactg gtatttcggt ttttggggcc | 600 |
| gcgggcggcg acggggcccg tgcgtcccag cgcacatgtt cggcgaggcg gggcctgcga | 660 |
| gcgcggccac cgagaatcgg acgggggtag tctcaagctg gccggcctgc tctggtgcct | 720 |
| ggtctcgcgc cgccgtgtat cgccccgccc tgggcggcaa ggctggcccg gtcggcacca | 780 |
| gttgcgtgag cggaaagatg gccgcttccc ggccctgctg cagggagctc aaaatggagg | 840 |
| acgcggcgct cgggagagcg ggcgggtgag tcacccacac aaaggaaaag ggcctttccg | 900 |
| tcctcagccg tcgcttcatg tgactccacg gagtaccggg cgccgtccag gcacctcgat | 960 |
| tagttctcga cttttggag tacgtcgtct ttaggttggg gggaggggtt ttatgcgatg | 1020 |
| gagtttcccc acactgagtg ggtggagact gaagttaggc cagcttggca cttgatgtaa | 1080 |
| ttctccttgg aatttgccct ttttgagttt ggatcttggt tcattctcaa gcctcagaca | 1140 |
| gtggttcaaa gttttttctct tccatttcag gtgtcgtga | 1179 |

<210> SEQ ID NO 14
<211> LENGTH: 1773
<212> TYPE: DNA
<213> ORGANISM: Artificial Sequence
<220> FEATURE:
<223> OTHER INFORMATION: Synthetic construct

<400> SEQUENCE: 14

| | |
|---|---|
| atggaaatgc aggatctaac cagcccgcat agccgactga gtggtagtag cgaatccccc | 60 |
| agtggtccca aactcgatag ctctcatata aatagtactt ccatgactcc caatggcacc | 120 |
| gaagttaaaa cagagccaat gagcagcagt gaaatagctt caacagcagc agacgggtct | 180 |
| ttagacagtt tctcaggttc agctctcgga agcagcagct ttagtccaag accagctcac | 240 |
| ccgttctctc caccacagat ttatccttcc aaatcatacc cacatattct ccctaccct | 300 |
| tcctcacaaa ctatggctgc atatgggcaa acacagttta ccacaggaat gcaacaagcc | 360 |
| acagcctacg ccacgtaccc acagcctgga cagccctatg gaatttcctc ctatggtgca | 420 |
| tgtgggcag gcatcaagac ggaaagtgga ttgtcacagt ctcagtcacc tggacagacg | 480 |
| ggatttctta gctatggcac aagctttggt acccctcaac ctggacaggc accgtacagc | 540 |
| taccagatgc aaggtagcag ctttaccacg tcatcaggat tatattcagg aaataattca | 600 |
| ctcaccaact cctccggatt caacagttca cagcaggact atccgtctta tcccggcttt | 660 |
| ggccagggtc agtacgcaca gtattataac agctcgccgt atccagcaca ctacatgacg | 720 |
| agcagtaaca ccagcccgac cacaccgtcc accaatgcca cttaccaact ccaggaacca | 780 |
| ccttctggcg tcacaagtca ggcggtcaca gaccccacag cagagtacag tacaatccac | 840 |
| agtccttcca cacccattaa agagactgac tccgagcggc tgcgtcgagg ttcagatggg | 900 |
| aagtcacgtg gccgaggcag aagaaacaat aatccctccc ctccccgga ttctgacctt | 960 |
| gagagagtgt tcatctggga cctggacgag accatcattg ttttccactc cttgctcacg | 1020 |
| gggtcctacg ccaacagata cgggaggat ccacctactt ctgtttccct gggactacga | 1080 |
| atggaagaga tgattttcaa cttggcagac acacatctat ttttcaatga cctagaagag | 1140 |
| tgtgaccaag tccatataga tgatgtttca tcagacgaca acggccagga cctgagcaca | 1200 |
| tacaactttg gaacagatgg ctttcctgct gcagccacca tgctaatttt atgcctggca | 1260 |
| actggtgtcc gaggtggtgt ggactggatg cggaaactgg ccttccgcta cagacgagta | 1320 |

```
aaagagatct acaacaccta caaaaacaac gtgggaggtc tgcttggccc agctaagagg    1380
gaagcctggc tccagctgag ggctgagatt gaggcactca cagactcctg gctgaccctg    1440
gccctgaagg ccctctccct catccactcc cggacgaact gtgtgaatat tttagtaaca    1500
actacgcagc tcatcccagc attggcaaaa gtcctgctat atggattagg aattgtgttt    1560
ccaatagaaa atatttacag tgcaactaaa ataggaaagg aaagctgttt tgagaggata    1620
atccaaaggt ttggaaggaa agtggtatac gttgtcatag agatggtgt ggaagaagag     1680 caagggcaa aaaagcatgc tatgcccttc tggagggtct ccagtcactc ggacctcatg     1740
gcactgcatc atgccttgga attagagtac ctg                                 1773

<210> SEQ ID NO 15
<211> LENGTH: 855
<212> TYPE: DNA
<213> ORGANISM: Artificial Sequence
<220> FEATURE:
<223> OTHER INFORMATION: Synthetic construct

<400> SEQUENCE: 15
atgtcgatgc tgccgtcgtt tggttttacg caagagcaag tggcgtgcgt gtgcgaagtt      60
ctgcagcaag gagggaacct ggaacgcctg gcaggttct  tgtggtcgtt gcccgcctgc    120
gatcacctgc acaagaacga gagcgtgctc aaggccaagg cggtggtcgc cttccaccgc    180
ggcaacttcc gcgagctcta caagatactg gagagccacc agttctcgcc tcacaatcac    240
cccaaactgc agcagctgtg gctgaaagcg cactacgtgg aggccgagaa acttcgcggc    300
cgacccctgg gtgccgtggg caaatatcgg gtgcgccgaa aattcccgtt gccgcggacc    360
atctgggacg gcgaggagac cagctactgc tttaaggaga gtctcggggg cgtgctgcgg    420
gagtggtacg cgcacaaccc ctaccctca ccgagggaga acgggagct ggccgaggcc      480 accggcctca ccaccaccca ggtcagcaac tggtttaaga accggaggca aagagaccgg    540
gccgccgagg ccaaggaaag ggagaacacc gaaaacaata actcctcctc caacaagcag    600
aatcaactct ctcctctgga aggggggcaag ccgctcatgt ccagctcaga agaggagttc    660
tcaccccccc aaagtccaga ccagaactcg gtccttctgc tccagagcaa tatgggccac    720
gccaggagct caaactattc tcttccaggc ctcacagcct cccagcccag ccacggtctg    780
caagcccatc agcaccagct ccaggactct ctgctgggcc cactcacctc cagtttggtg    840
gacttgggtt cctaa                                                     855

<210> SEQ ID NO 16
<211> LENGTH: 807
<212> TYPE: DNA
<213> ORGANISM: Artificial Sequence
<220> FEATURE:
<223> OTHER INFORMATION: Synthetic construct

<400> SEQUENCE: 16
atgccgcgct ccttcctggt caagaaacat ttcaacgcct ccaagaagcc caactacagc      60
gaactggaca cacacacagt tattatttcc ccatatctct atgaaagtta ccctataccct    120 gtcataccaa aaccagagat cctcacctcg ggagcataca gccctattac tgtatgggaca    180 tcgtcggcag ctccactcca ctctcctttta cccagtggcc tttctcctct tactggatac    240
tcctcatcct tggggcgtgt aagtcccccg ccttcctctg acacttcatc caaggatcac    300
agtggttcag aaagtcccat tagtgacgaa gaggagagac tgcagcccaa gctttcagac    360
```

```
ccccatgcca tcgaagctga gaagtttcag tgcaatttat gcaataagac ctattctacg    420
ttctctgggc tggccaaaca caagcagctg cactgtgatg cccagtctag gaaatcgttc    480
agctgcaagt actgtgacaa ggaatatgtg agcctgggtg ccctgaagat gcacattcga    540
acccacacat tgccttgtgt ctgcaagatc tgtggcaagg cttctctcca gaccctggctg   600 cttcaaggac acattagaac tcacactggg gaaaagcctt tctcttgccc tcactgcaat    660
agggcttttg cagacagatc aaacctgagg gcacatctgc agaccccactc tgatgtaaag  720 aaataccagt gcaaaaactg ctccaaaacc ttctccagaa tgtcgcttct gcataaacat    780
gaggagtctg gctgctgtgt ggcacac                                       807

<210> SEQ ID NO 17
<211> LENGTH: 6
<212> TYPE: DNA
<213> ORGANISM: Artificial Sequence
<220> FEATURE:
<223> OTHER INFORMATION: Synthetic construct

<400> SEQUENCE: 17 gccacc                                                                6

<210> SEQ ID NO 18
<211> LENGTH: 75
<212> TYPE: DNA
<213> ORGANISM: Artificial Sequence
<220> FEATURE:
<223> OTHER INFORMATION: Synthetic construct

<400> SEQUENCE: 18
ggaagcggag tgaaacagac tttgaatttt gaccttctga agttggcagg agacgttgag    60
tccaaccctg ggccc                                                     75

<210> SEQ ID NO 19
<211> LENGTH: 69
<212> TYPE: DNA
<213> ORGANISM: Artificial Sequence
<220> FEATURE:
<223> OTHER INFORMATION: Synthetic construct

<400> SEQUENCE: 19
ggaagcggac agtgtactaa ttatgctctc ttgaaattgg ctggagatgt tgagagcaac    60
ccaggtccc                                                            69

<210> SEQ ID NO 20
<211> LENGTH: 522
<212> TYPE: DNA
<213> ORGANISM: Artificial Sequence
<220> FEATURE:
<223> OTHER INFORMATION: Synthetic construct

<400> SEQUENCE: 20
tcctcaggtg caggctgcct atcagaaggt ggtggctggt gtggccaatg ccctggctca    60
caaataccac tgagatcttt ttccctctgc caaaaattat ggggacatca tgaagcccct   120
tgagcatctg acttctggct aataaaggaa atttattttc attgcaatag tgtgttggaa   180
ttttttgtgt ctctcactcg gaaggacata tgggagggca aatcatttaa acatcagaa    240 tgagtatttg gtttagagtt tggcaacata tgcccatatg ctggctgcca tgaacaaagg   300
ttggctataa agaggtcatc agtatatgaa acagccccct gctgtccatt ccttattcca   360
tagaaaagcc ttgacttgag gttagatttt ttttatattt tgttttgtgt tatttttttc   420
```

```
tttaacatcc ctaaaatttt ccttacatgt tttactagcc agatttttcc tcctctcctg    480
actactccca gtcatagctg tccctcttct cttatggaga tc                      522
```

<210> SEQ ID NO 21
<211> LENGTH: 66
<212> TYPE: DNA
<213> ORGANISM: Artificial Sequence
<220> FEATURE:
<223> OTHER INFORMATION: Synthetic construct

<400> SEQUENCE: 21

```
ggatccggag ccacgaactt ctctctgtta aagcaagcag agacgtgga agaaaacccc    60 ggtccc                                                              66
```

<210> SEQ ID NO 22
<211> LENGTH: 69
<212> TYPE: DNA
<213> ORGANISM: Artificial Sequence
<220> FEATURE:
<223> OTHER INFORMATION: Synthetic construct

<400> SEQUENCE: 22

```
ggctccggat ccggagaggg cagaggaagt ctgctaacat gcggtgacgt cgaggagaat   60
cctggccca                                                           69
```

<210> SEQ ID NO 23
<211> LENGTH: 57
<212> TYPE: DNA
<213> ORGANISM: Artificial Sequence
<220> FEATURE:
<223> OTHER INFORMATION: Synthetic construct

<400> SEQUENCE: 23

```
gctaccaatt ttagcttgct caaacaggcc ggggatgttg aggaaaatcc aggaccg      57
```

<210> SEQ ID NO 24
<211> LENGTH: 54
<212> TYPE: DNA
<213> ORGANISM: Artificial Sequence
<220> FEATURE:
<223> OTHER INFORMATION: Synthetic construct

<400> SEQUENCE: 24

```
gaaggtcgtg gctccttgtt gacctgtggc gatgtggaag aaaacccagg ccct         54
```

<210> SEQ ID NO 25
<211> LENGTH: 22
<212> TYPE: PRT
<213> ORGANISM: Artificial Sequence
<220> FEATURE:
<223> OTHER INFORMATION: Synthetic construct

<400> SEQUENCE: 25

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 26
<211> LENGTH: 23
<212> TYPE: PRT
<213> ORGANISM: Artificial Sequence
<220> FEATURE:

<223> OTHER INFORMATION: Synthetic construct

<400> SEQUENCE: 26

Gly Ser Gly Ser Gly Glu Gly Arg Gly Ser Leu Leu Thr Cys Gly Asp
1               5                   10                  15

Val Glu Glu Asn Pro Gly Pro
            20

<210> SEQ ID NO 27
<211> LENGTH: 19
<212> TYPE: PRT
<213> ORGANISM: Artificial Sequence
<220> FEATURE:
<223> OTHER INFORMATION: Synthetic construct

<400> SEQUENCE: 27

Ala Thr Asn Phe Ser Leu Leu Lys Gln Ala Gly Asp Val Glu Glu Asn
1               5                   10                  15

Pro Gly Pro

<210> SEQ ID NO 28
<211> LENGTH: 18
<212> TYPE: PRT
<213> ORGANISM: Artificial Sequence
<220> FEATURE:
<223> OTHER INFORMATION: Synthetic construct

<400> SEQUENCE: 28

Glu Gly Arg Gly Ser Leu Leu Thr Cys Gly Asp Val Glu Glu Asn Pro
1               5                   10                  15

Gly Pro

<210> SEQ ID NO 29
<211> LENGTH: 22
<212> TYPE: PRT
<213> ORGANISM: Artificial Sequence
<220> FEATURE:
<223> OTHER INFORMATION: Synthetic construct

<400> SEQUENCE: 29

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic construct

<400> SEQUENCE: 30

Gln Cys Thr Asn Tyr Ala Leu Leu Lys Leu Ala Gly Asp Val Glu Ser
1               5                   10                  15

Asn Pro Gly Pro
            20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

```
<400> SEQUENCE: 31
gagcaaagtc ataaacggcg                                           20

<210> SEQ ID NO 32
<211> LENGTH: 22
<212> TYPE: DNA
<213> ORGANISM: Artificial Sequence
<220> FEATURE:
<223> OTHER INFORMATION: Synthetic construct

<400> SEQUENCE: 32
cttttgagcg agtttccttg tc                                        22

<210> SEQ ID NO 33
<211> LENGTH: 23
<212> TYPE: DNA
<213> ORGANISM: Artificial Sequence
<220> FEATURE:
<223> OTHER INFORMATION: Synthetic construct

<400> SEQUENCE: 33
tcagaacagg agaatgaagg aaa                                       23

<210> SEQ ID NO 34
<211> LENGTH: 18
<212> TYPE: DNA
<213> ORGANISM: Artificial Sequence
<220> FEATURE:
<223> OTHER INFORMATION: Synthetic construct

<400> SEQUENCE: 34
acatcgccac aggtcaac                                             18

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
ctttgttgaa actcgctggc                                           20

<210> SEQ ID NO 36
<211> LENGTH: 22
<212> TYPE: DNA
<213> ORGANISM: Artificial Sequence
<220> FEATURE:
<223> OTHER INFORMATION: Synthetic construct

<400> SEQUENCE: 36
ggcagcatcg acatcaattt aa                                        22

<210> SEQ ID NO 37
<211> LENGTH: 20
<212> TYPE: DNA
<213> ORGANISM: Artificial Sequence
<220> FEATURE:
<223> OTHER INFORMATION: Synthetic construct

<400> SEQUENCE: 37
ggcgattaag ttgggtaacg                                           20

<210> SEQ ID NO 38
```

```
<211> LENGTH: 20
<212> TYPE: DNA
<213> ORGANISM: Artificial Sequence
<220> FEATURE:
<223> OTHER INFORMATION: Synthetic construct

<400> SEQUENCE: 38
actggaaagc gggcagtgag                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic construct

<400> SEQUENCE: 39
cgacggccag tgaattcgag                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic construct

<400> SEQUENCE: 40
cttccggctc gtatgttgtg                                          20
```